United States Patent
Qi et al.

(10) Patent No.: US 11,702,402 B2
(45) Date of Patent: Jul. 18, 2023

(54) SMALL MOLECULES THAT BLOCK PROTEASOME-ASSOCIATED UBIQUITIN RECEPTOR RPN13 FUNCTION AND USES THEREOF

(71) Applicant: DANA-FARBER CANCER INSTITUTE, INC., Boston, MA (US)

(72) Inventors: Jun Qi, Sharon, MA (US); Kenneth C. Anderson, Wellesley, MA (US); Lei Wu, Shanghai (CN); Yan Song, Brookline, MA (US); Dharminder Chauhan, Natick, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 302 days.

(21) Appl. No.: 16/969,458

(22) PCT Filed: Feb. 22, 2019

(86) PCT No.: PCT/US2019/019162
§ 371 (c)(1),
(2) Date: Aug. 12, 2020

(87) PCT Pub. No.: WO2019/165216
PCT Pub. Date: Aug. 29, 2019

(65) Prior Publication Data
US 2021/0130324 A1 May 6, 2021

Related U.S. Application Data

(60) Provisional application No. 62/634,632, filed on Feb. 23, 2018.

(51) Int. Cl.
*C07D 401/14* (2006.01)
*A61P 35/04* (2006.01)
*C07D 495/04* (2006.01)

(52) U.S. Cl.
CPC .......... *C07D 401/14* (2013.01); *A61P 35/04* (2018.01); *C07D 495/04* (2013.01)

(58) Field of Classification Search
CPC .................................................. C07D 401/14
See application file for complete search history.

(56) References Cited

U.S. PATENT DOCUMENTS

2015/0291562 A1* 10/2015 Crew ..................... A61P 31/12
435/375
2016/0106725 A1 4/2016 Roden et al.

OTHER PUBLICATIONS

Bondeson, et al., "Lessons in PROTAC design from selective degradation with a promiscuous warhead", Cell Chem Biol. Jan. 18, 2018; 25(1): 78-87.
Huang, et al., "A Chemoproteomic Approach to Query the Degradable Kinome Using a Multi-kinase Degrader", Cell Chem Biol Jan. 18, 2018; 25(1): 88-99.
Lai, et al., "Modular PROTAC Design for the Degradation of Oncogenic BCR-ABL", Angew. Chem. Int. Ed. ☐☐☐☐, 55, 807-810.
Nowak, et al., "Plasticity in binding confers selectivity in ligand induced protein degradation", Nat Chem Biol. Jul. 2018; 14(7): 706-714.
Pettersson, et al., "PROteolysis TArgeting Chimeras (PROTACs)—Past, present and future", 2019, Drug Discovery Today: Technologies, vol. 31, pp. 15-27.

* cited by examiner

*Primary Examiner* — Rei Tsang Shiao
(74) *Attorney, Agent, or Firm* — Burns & Levinson, LLP; Daniel W. Clarke; Shawn P. Foley

(57) ABSTRACT

Provided herein are bifunctional compounds with a moiety (e.g., lenalidomide, thalidomide) that is a binder of an E3 ubiquitin ligase (e.g., Cereblon) and another moiety (e.g., RA190) that is a binder of the ubiquitin receptor RPN13 to induce degradation of RPN13 and thereby inhibit proteasome function. Also provided are pharmaceutical compositions comprising the bifunctional compounds, and methods of treating and/or preventing diseases (e.g., proliferative diseases, cancers, benign neoplasms, pathological angiogenesis, inflammatory diseases, and autoimmune diseases). Provided also are methods of inducing the degradation of ubiquitin receptor RPN13 by administering a bifunctional compound or composition described herein, wherein one component of the bifunctional compound is a binder of an E3 ubiquitin ligase (e.g., lenalidomide, thalidomide) and another component of the compound is a binder of ubiquitin receptor RPN13 (e.g., RA190) in a subject.

20 Claims, 38 Drawing Sheets

Specification includes a Sequence Listing.

JQRA

| | WL40(nM) | Pom(µM) | FE | CI |
|---|---|---|---|---|
| 1 | 25 | 0.625 | 0.1050 | 0.993 |
| 2 | 25 | 1.25 | 0.2193 | 0.939 |
| 3 | 25 | 2.5 | 0.6037 | 0.786 |
| 4 | 50 | 0.625 | 0.2912 | 0.765 |
| 5 | 50 | 1.25 | 0.4331 | 0.762 |
| 6 | 50 | 2.5 | 0.7370 | 0.688 |
| 7 | 100 | 0.625 | 0.7790 | 0.362 |
| 8 | 100 | 1.25 | 0.8910 | 0.323 |
| 9 | 100 | 2.5 | 0.9821 | 0.23 |

| | WL40(nM) | Len(μM) | FE | CI |
|---|---|---|---|---|
| 1 | 25 | 0.625 | 0.1624 | 0.888 |
| 2 | 25 | 1.25 | 0.2722 | 0.938 |
| 3 | 25 | 2.5 | 0.4848 | 0.963 |
| 4 | 50 | 0.625 | 0.2939 | 0.81 |
| 5 | 50 | 1.25 | 0.4029 | 0.847 |
| 6 | 50 | 2.5 | 0.6299 | 0.788 |
| 7 | 100 | 0.625 | 0.5686 | 0.629 |
| 8 | 100 | 1.25 | 0.6997 | 0.565 |
| 9 | 100 | 2.5 | 0.8009 | 0.593 |

| | WL40(nM) | BTZ (nM) | FE | CI |
|---|---|---|---|---|
| 1 | 25 | 0.3125 | 0.1121 | 0.792 |
| 2 | 25 | 0.625 | 0.1718 | 0.799 |
| 3 | 25 | 1.25 | 0.3470 | 0.767 |
| 4 | 50 | 0.3125 | 0.1979 | 0.889 |
| 5 | 50 | 0.625 | 0.2294 | 0.97 |
| 6 | 50 | 1.25 | 0.5545 | 0.635 |
| 7 | 100 | 0.3125 | 0.4627 | 0.729 |
| 8 | 100 | 0.625 | 0.6248 | 0.574 |
| 9 | 100 | 1.25 | 0.9463 | 0.219 |

SMALL MOLECULES THAT BLOCK PROTEASOME-ASSOCIATED UBIQUITIN RECEPTOR RPN13 FUNCTION AND USES THEREOF

RELATED APPLICATIONS

This application is a national stage application, filed under 35 U.S.C. § 371, of International Application No. PCT/US2019/019162, filed Feb. 22, 2019, which claims priority under 35 U.S.C. § 119(e) to U.S. Provisional Application, U.S. Ser. No. 62/634,632, filed Feb. 23, 2018, the entire contents of each of which are incorporated herein by reference.

GOVERNMENT SUPPORT

This invention was made with government support under grant numbers P50100707, R01CA207237, and R01CA050947 awarded by the National Institutes of Health (NIH). The government has certain rights in the invention.

SEQUENCE LISTING

This application contains a Sequence Listing which has been submitted in ASCII format via EFS-Web and is hereby incorporated by reference in its entirety. The ASCII copy of the Sequence Listing, created on Oct. 5, 2020, is named "52095-693N01US_ST25.txt" and is 29 KB in size.

BACKGROUND OF THE INVENTION

E3 ubiquitin ligases are proteins that, in combination with an E2 ubiquitin-conjugating enzyme, promote the attachment of ubiquitin to a lysine on a target protein via an isopeptide bond (e.g., an amide bond that is not present on the main chain of a protein). The ubiquitination of the target protein results in degradation of the target protein by the proteasome.

RA190 covalently binds to the ubiquitin receptor RPN13 (ADRM1) of the regulatory particle 19S, which in turn inhibits proteasome function. See US Appl. Pub. No. 2016/0106725. The subsequent accumulation of polyubiquitinated proteins induces apoptosis in cells (e.g., cancer cells).

Multiple myeloma (MM) accounts for 10% of all hematologic malignancies and affects 30,200 new individuals annually in United States, highlighting the need for development of novel therapeutic approaches. Proteasome inhibitors ("PIs") bortezomib, carfilzomib, and ixazomib are FDA approved drugs for the treatment of relapsed/refractory and newly diagnosed MM.[1-4] Although PI therapies have contributed to major advances, their clinical use has been associated with adverse effects and the emergence of drug-resistance, underlying relapse of disease.[2-5] Importantly, the ability of PIs to overcome resistance to conventional therapies has validated the Ubiquitin Proteasome System (UPS) as a therapeutic target in MM. Other than the 20S proteasome holoenzyme which is targeted by PI,[6-9] there are several other potential therapeutic targets within the UPS including deubiquitinating enzymes and ubiquitin receptors (UbRs) which represent targets to enhance or even overcome PI resistance.

Other studies have focused on validating and targeting the UbR Rpn13/ADRM1 upstream of the 20S proteasome in cancers and in MM in particular.[10-14] Rpn13 is associated with the 19S regulatory component of the proteasome and plays a key role in directing ubiquitinated substrates for degradation via the 20S proteasome.[15-17] Specifically, Rpn13 captures the ubiquitinated proteins as substrate, followed by removal of ubiquitin moieties from the substrate by deubiquitinating enzymes UCH37 at the 19S proteasome; the target protein is then unfolded by the AAA-ATPases for 20S proteasome-mediated degradation. To date, strategies to delineate the functionality of Rpn13 used genetic modulation and small molecule inhibitors.[10, 12, 14, 18, 19] For example, it was shown that Rpn13 expression level is higher in MM cells than in normal plasma cells and that Rpn13 mediates MM cell growth and survival;[10] both RNA interference and a proof-of-concept Rpn13 inhibitor RA190[11] confirmed that inhibiting Rpn13 induces MM cell growth inhibition.[10]. Another study used a peptoid Rpn13 inhibitor to show anti-tumor responses.[13] Currently, however, there are no clinical grade agents targeting Rpn13.

Small molecule inhibitors have shown clinical efficacy in many cancers, but their utility may be limited since: 1) high systemic concentrations are required to inhibit disease-related target proteins to achieve clinical benefits, which triggers off-target binding activities; and 2) inhibitors usually block the activity of one domain of multidomain proteins, leaving the functional properties of other domains intact. For example, Rpn13 inhibitor RA190 covalently reacts with cysteine residue 88 (Cys88) of Rpn13 Pru domain, but its interaction with the DEUBAD domain of Rpn13 is more labile due to lack of a favorable binding pocket;[11, 20, 21] and 3) inhibition of target proteins may trigger compensatory feedback mechanisms including protein overexpression/accumulation, resulting in inadequate inhibition of the protein.[22, 23] Inspired by the recent strategy utilizing small molecules to induce targeted protein degradation, this alternative strategy was explored by designing a small molecule-based degrader to eliminate Rpn13 at the protein level.

Therefore, there is a need to identify bifunctional compounds that can effectively induce the degradation of RPN13 in order to inhibit proteasome function, which may be useful in treating certain pathological states, including proliferative diseases, cancers, benign neoplasms, and inflammatory diseases. A bifunctional compound that also simultaneously binds E3 ubiquitin ligases with this RPN13 degradation-inducing compound is a way to induce the degradation of RPN13. In particular, compounds that can take advantage of cellular machinery involved in protein homeostasis (e.g., ubiquitination and proteasome degradation) to target the degradation of RPN13 may be useful as therapeutic agents.

SUMMARY OF THE INVENTION

Recent work has led to the discovery of a mechanism-based chemical for endogenous target protein degradation by using heterobifunctional small-molecule ligands to recruit E3 ubiquitin ligases to induce target protein degradation.[22-28] Degronimids, also known as proteolysis-targeting chimeras (PROTACs), are designed by conjugating a small-molecule binder of the target protein to an E3 ubiquitin ligase binding scaffold, such as analogues of thalidomide for binding to Cereblon (CRBN) or ligands that bind to von Hippel-Lindau (VHL). Mechanistically, the degraders engage the target protein and recruit them to the E3 Ubiquitin ligase, thereby promoting its ubiquitination and subsequent degradation by the proteasome.[29] This strategy has been applied to several proteins including the bromodomain and extra terminal (BET) family (BRD2, BRD3, BRD4), BCR-ABL, FKBP12, ERRα, and RIPK2[25-29-31]

Studies herein also encompass on validating and targeting the UbR Rpn13/ADRM1 upstream of the 20S proteasome in cancers and in MM in particular. With both the inhibitor and degrader, it is evaluated herein whether protein degradation may overcome these above-noted limitations of small molecule inhibitors (1) high systemic concentrations that are required to inhibit disease-related target proteins to achieve clinical benefits, which triggers off-target binding activities; and 2) inhibitors usually block the activity of one domain of multidomain proteins, leaving the functional properties of other domains intact).

The present disclosure stems from the recognition that a bifunctional molecule that includes an E3 ubiquitin ligase binding moiety that is based on an immunomodulatory imide drug (e.g., lenalidomide, thalidomide) and also includes a binder of the ubiquitin receptor RPN13 (e.g., RA190) may induce proteasome degradation of ubiquitin receptor RPN13, thereby inhibiting proteasome function. This discovery provides a new mode of inhibiting proteasome function. The disclosure therefore provides new compounds, compositions, and methods for the treatment of various diseases (e.g., proliferative diseases, cancers, benign neoplasms, and inflammatory diseases) based on this discovery.

Described herein are bifunctional compounds of Formulae (I) and (I'). The compounds described herein include a component that binds to the ubiquitin receptor RPN13 and a component that binds an E3 ubiquitin ligase (e.g., lenalidomide, thalidomide) and therefore may be useful in promoting the degradation of the ubiquitin receptor RPN13. For example, described herein is an exemplary inducer of RPN13 degradation, WL40 (See FIG. 2 and Brief Description of FIG. 2 below for structure of WL40), where the Rpn13 inhibitor, RA190, is linked to an immunomodulatory drug (IMiD) (thalidomide) as a ligand for CRBN E3 ligase. Exemplary compound WL40 promotes ligand-induced degradation of Rpn13 by the proteasome, which utilizes a covalent inhibitor as the target protein binder. Using both in vitro and in vivo preclinical models and MM patient cells, it is confirmed that WL40 triggers potent anti-MM activity, overcoming PI resistance. WL-40 demonstrates promising anti-MM activity. FIGS. 1A and 1B show the design principle behind the bifunctional compounds described herein. The compounds may be useful in treating and/or preventing disease and conditions, such as a proliferative disease (e.g., cancers, benign neoplasms, pathological angiogenesis, inflammatory diseases, and autoimmune diseases) in a subject in need thereof. Also provided are pharmaceutical compositions and kits including a compound described herein.

In one aspect, the present disclosure provides compounds of Formulae (I) and (I'):

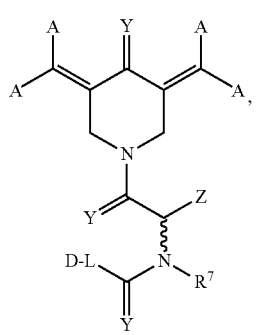
(I)

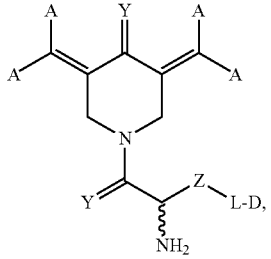
(I')

and pharmaceutically acceptable salts, solvates, hydrates, polymorphs, co-crystals, tautomers, stereoisomers, isotopically labeled derivatives, and prodrugs thereof, wherein A, Y, $R^7$, Z, L, and D are as defined herein. The moieties

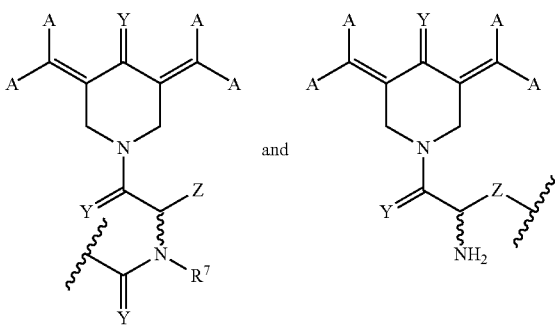

are derived from RA190, a binder of the ubiquitin receptor RPN13.

In Formulae (I) and (I'), D is a E3 ubiquitin ligase binding moiety. In certain embodiments, D is derived from an immunomodulatory imide drug. In certain embodiments, D is derived from lenalidomide. In certain embodiments, D is derived from thalidomide. In certain embodiments, D is an E3 ubiquitin ligase binding moiety, wherein D is of Formulae (IA) or (IB).

In certain embodiments, D is of Formula (IA):

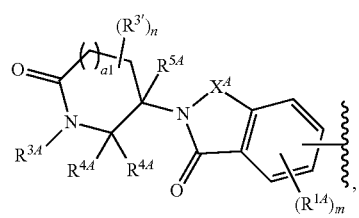
(IA)

wherein $R^{1A}$, $R^{3A}$, $R^{4A}$, $R^{5A}$, $R^3$, $X^A$, a1, m, and n are as defined herein.

In certain embodiments, D is of Formula (IB):
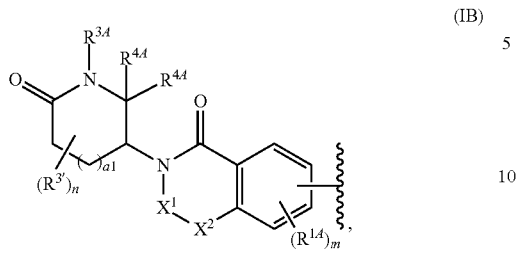
(IB)
wherein $R^{1A}$, $R^{3A}$, $R^{4A}$, $R^3$, $X^1$, $X^2$, a1, m, and n are as defined herein.
Exemplary compounds of Formulae (I) and (I') include, but are not limited to:
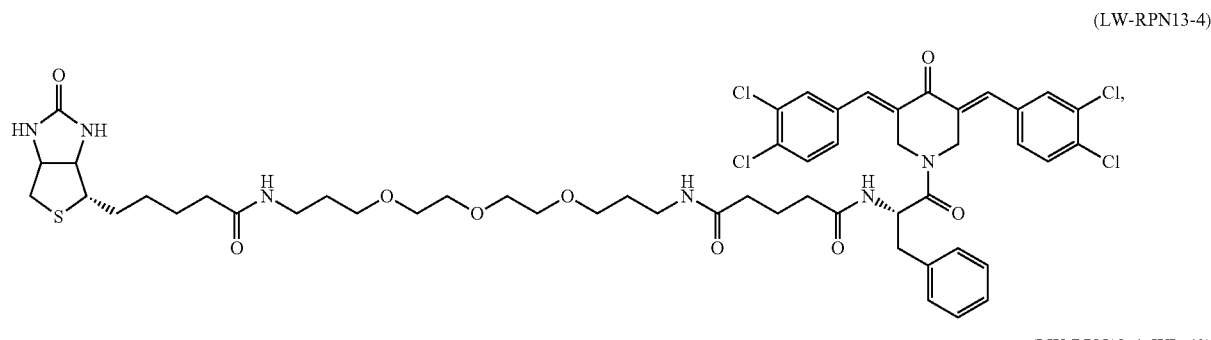
(LW-RPN13-4)
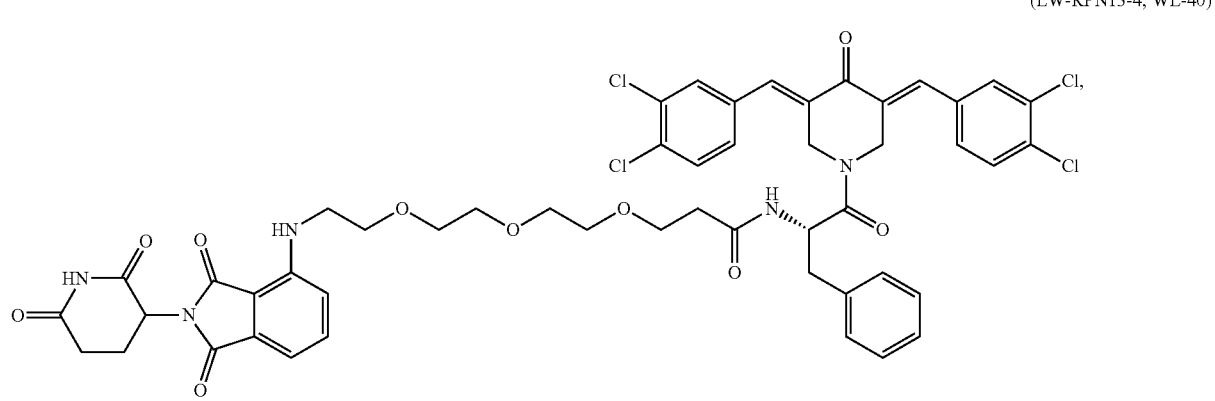
(LW-RPN13-4; WL-40)
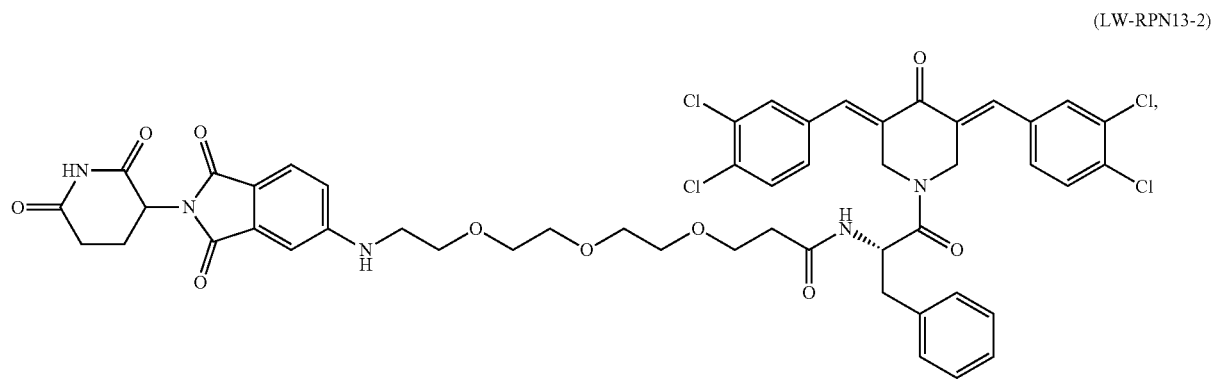
(LW-RPN13-2)

-continued
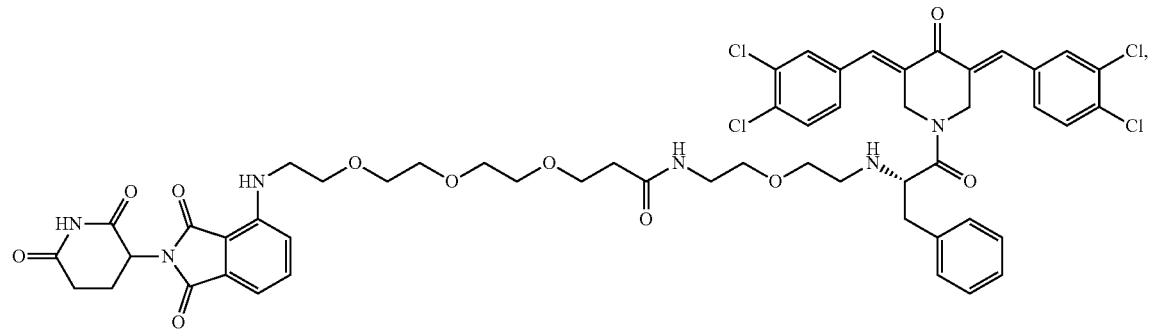
(dRPN13-3)
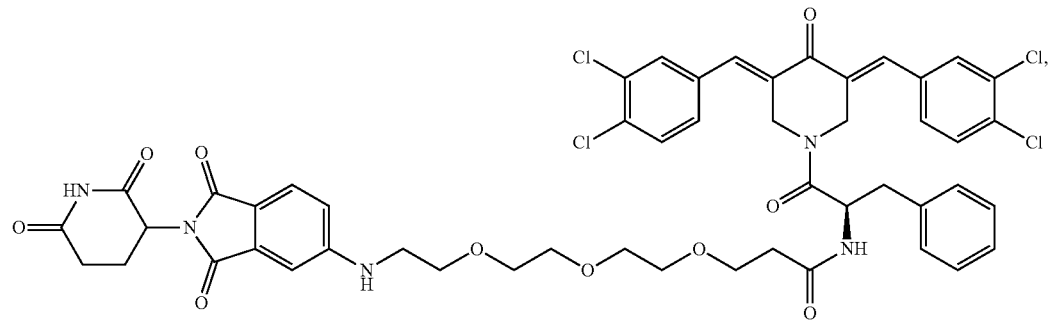
(WL44)
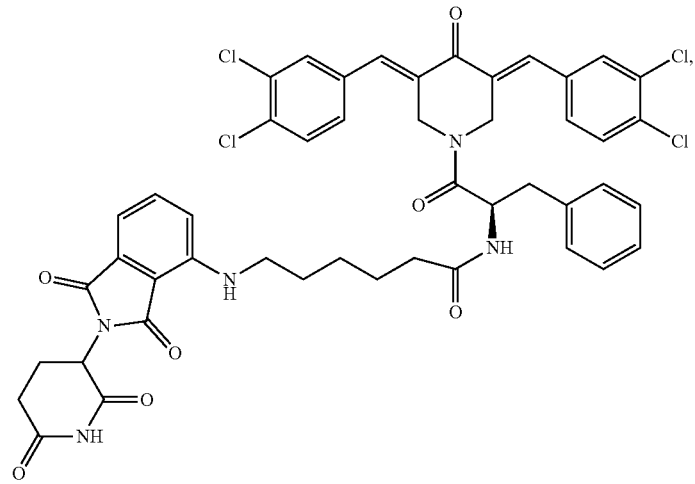
(WL4)
JQRA
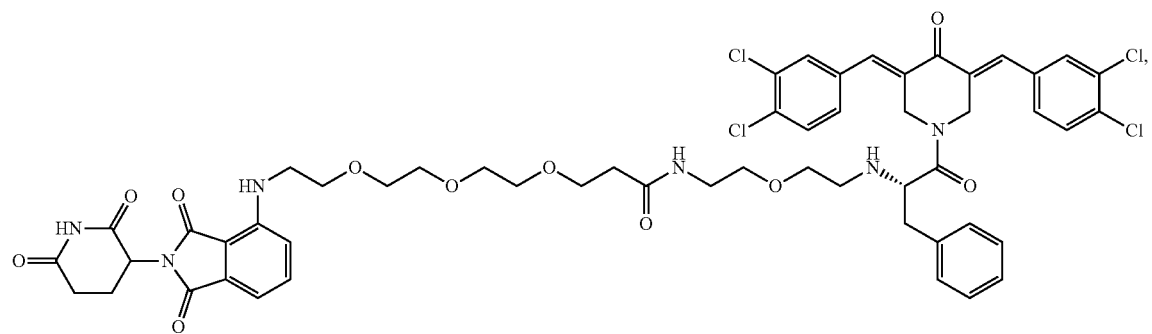

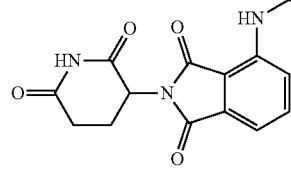
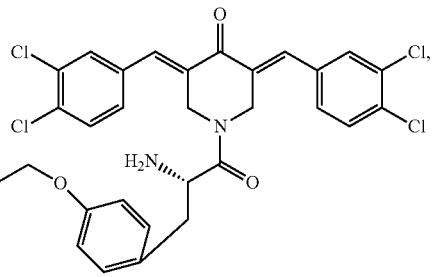
and pharmaceutically acceptable salts, solvates, hydrates, polymorphs, co-crystals, tautomers, stereoisomers, isotopically labeled derivatives, and prodrugs thereof
Exemplary compounds of Formulae (I) and (I') include, but are not limited to:
(LW-RPN13-4)
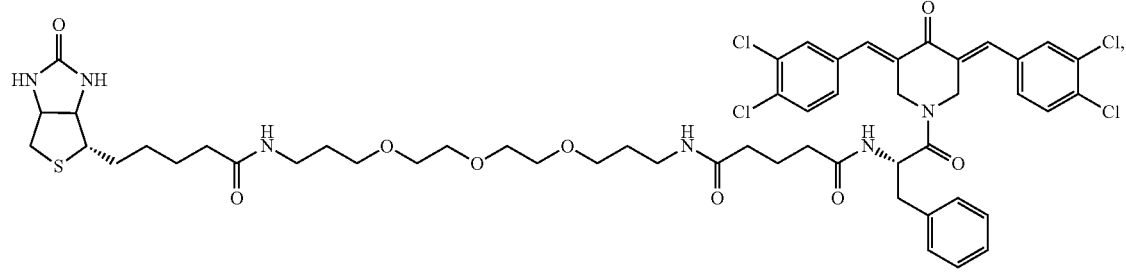
(LW-RPN13-1; WL-40)
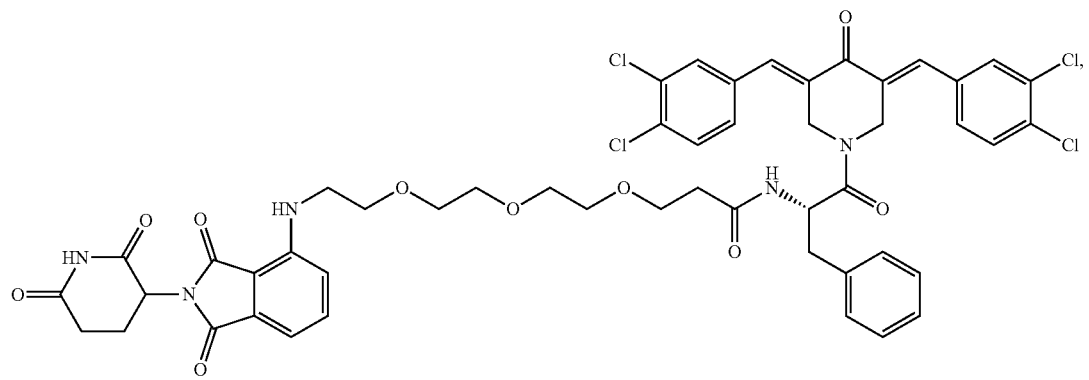
(LW-RPN13-2)
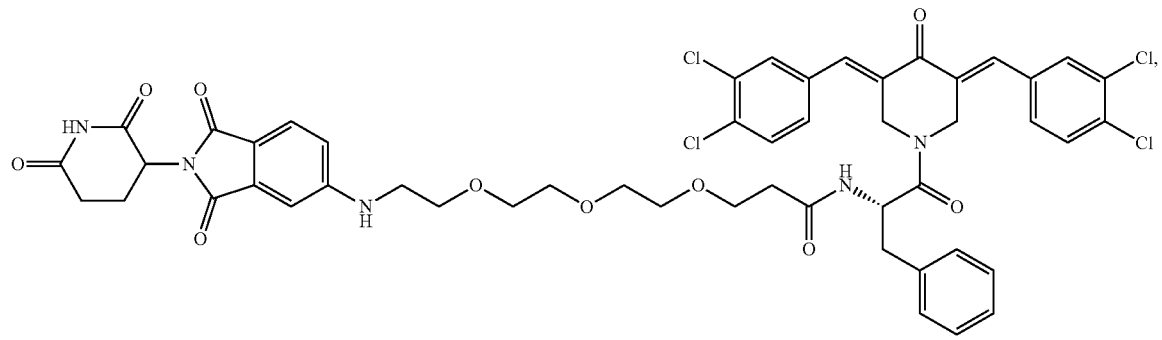

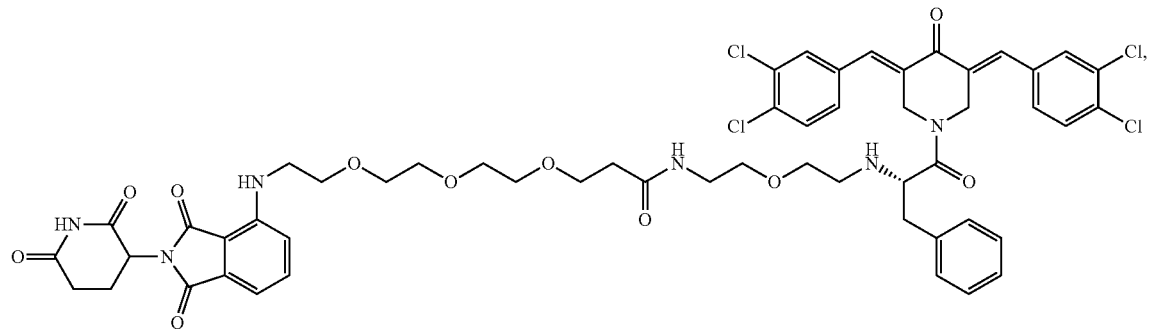
(dRPN13-3)
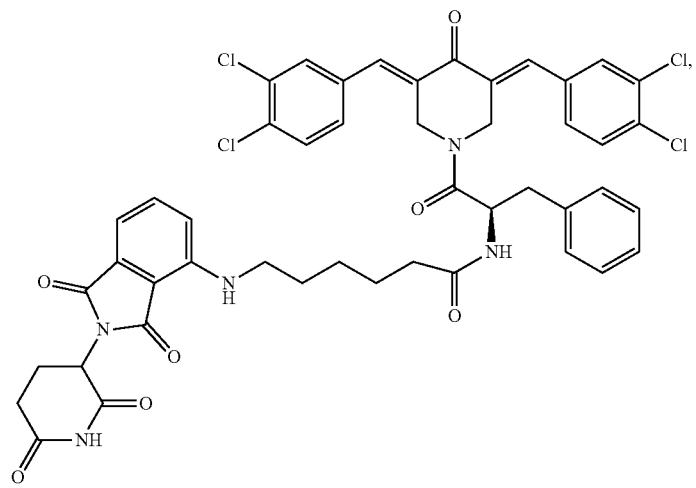
(WL4)
JQRA
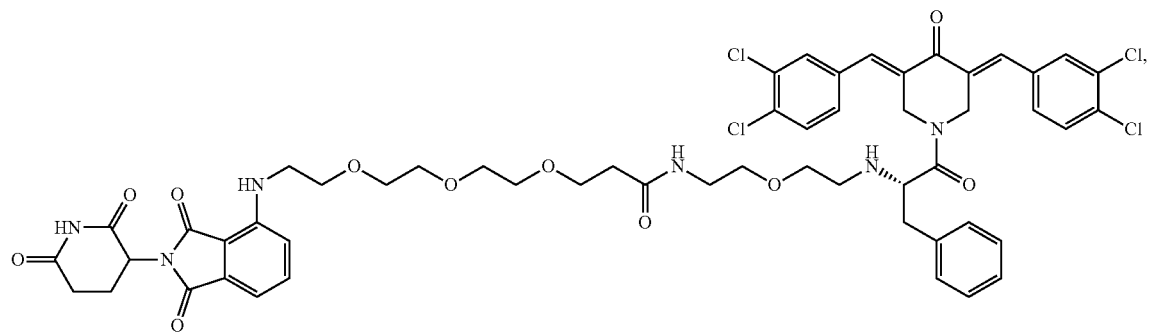
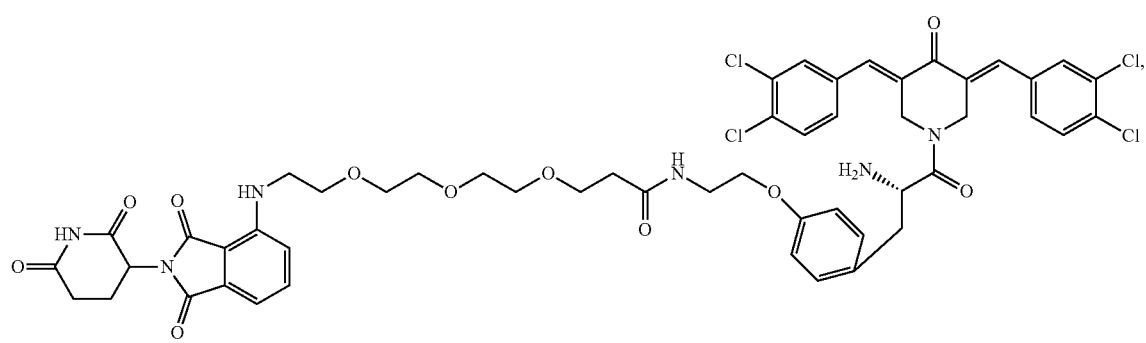

and pharmaceutically acceptable salts, solvates, hydrates, polymorphs, co-crystals, tautomers, stereoisomers, isotopically labeled derivatives, and prodrugs thereof In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in inducing the degradation of RPN13 in a subject or cell, in treating a disease (e.g., a proliferative disease) in a subject in need thereof, or in preventing a disease in a subject in need thereof. In certain embodiments, the compound being administered or used induces the degradation of RPN13 in a subject or cell, in treating a disease (e.g., a proliferative disease) in a subject in need thereof, or in preventing a disease in a subject in need thereof.

In still another aspect, described herein are kits including a container with a compound or pharmaceutical composition described herein. A kit described herein may include a single dose or multiple doses of the compound or pharmaceutical composition. The described kits may be useful in inducing the degradation of the ubiquitin receptor RPN13. In certain embodiments, a kit described herein further includes instructions for using the compound or pharmaceutical composition included in the kit.

In certain embodiments, the compound being administered or used induces the degradation of the ubiquitin receptor RPN13. In certain embodiments, the compound being administered or used inhibits protasome function in a cell (e.g., in a cell of a subject). In another aspect, the present disclosure provides methods of killing cells (e.g. killing a cancer cell or tumor cell), the methods comprising contacting the cell with an effective amount of a compound or pharmaceutical composition described herein. In another aspect, the present disclosure provides methods of inducing apoptosis of a cell. In another aspect, the present disclosure provides methods of inducing the accumulation of ubiquitinated proteins in a cell.

Another aspect of the present disclosure relates to methods of treating a disease in a subject in need thereof, the methods comprising administering to the subject a therapeutically effective amount of a compound or pharmaceutical composition described herein. In another aspect, the present disclosure provides methods of preventing a disease in a subject in need thereof, the methods comprises administering to the subject a prophylactically effective amount of a compound or pharmaceutical composition described herein.

In yet another aspect, the present disclosure provides compounds and pharmaceutical compositions described herein for use in a method of the disclosure (e.g., a method of inducing the degradation of the ubiquitin receptor RPN13, a method of inhibiting proteasome function, a method of killing cells (e.g. cancer cells or tumor cells), a method of treating a disease (e.g., a proliferative disease), or a method of preventing a disease (e.g., a proliferative disease)).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-5}$, $C_{3-4}$, $C_{4-6}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Hetero aralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix-ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_2^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

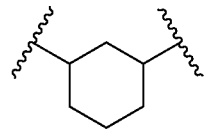 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

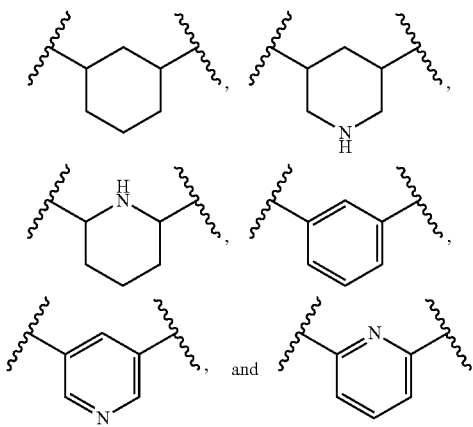

are all examples of a hydrocarbon chain. In contrast, in certain embodiments,

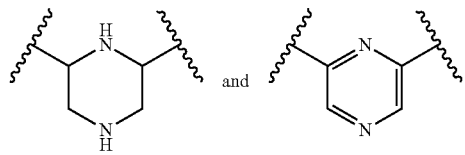 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

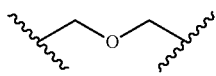 [SMILES: *COC*]

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

As used herein the term "inhibit" or "inhibition" in the context of enzymes, for example, in the context of an enzyme, refers to a reduction in the level of protein by promoting degradation of the protein. The reduction in the level of protein thus reduces the level of the activity of the protein. As used herein the term "inhibit" or "inhibition" in the context of the proteasome, for example, refers to a reduction in the level of activity by the proteasome, for example, reducing the level of proteasome degradation. In some embodiments, the term refers to a reduction of the level of proteasome activity to a level that is statistically significantly lower than an initial level, which may, for example, be a baseline level of proteasome activity. In some embodiments, the term refers to a reduction of the level of proteasome activity to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of proteasome activity.

When a compound, pharmaceutical composition, method, use, or kit is referred to as "selectively," "specifically," or "competitively" inhibiting a target (e.g., enzyme, E3 ligase or RPN13), the compound, pharmaceutical composition, method, use, or kit inhibits the target enzyme, to a greater extent (e.g., not less than 2-fold, not less than 5-fold, not less than 10-fold, not less than 30-fold, not less than 100-fold, not less than 1,000-fold, or not less than 10.000-fold; and/or: not more than 2-fold, not more than 5-fold, not more than 10-fold, not more than 30-fold, not more than 100-fold, not more than 1,000-fold, or not more than 10.000-fold) than inhibiting a different target (e.g., enzyme, E3 ligase or RPN13).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for binding a target (e.g., a protein (e.g., E3 ligase or RPN13) (and/or inducing the degradation of the target (e.g., a protein (e.g., E3 ligase or RPN13)).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for binding a target (e.g., a protein (e.g., E3 ligase or RPN13). In certain embodiments, a prophylactically effective amount is an amount sufficient for treating a proliferative disease (e.g., cancer). In certain embodiments, a prophylactically effective amount is an amount sufficient for binding a target (e.g., a protein (e.g., E3 ligase or RPN13) and/or inducing the degradation of the target (e.g., a protein (e.g., E3 ligase or RPN13) and treating a proliferative disease (e.g., cancer).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis vims or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism. In certain embodiments, a hematological disease is a hematological malignancy. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis *nodosa*, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts;

arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other poly glutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Lisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The term "small molecule" refers to molecules, whether naturally-occurring or artificially created (e.g., via chemical synthesis) that have a relatively low molecular weight.

Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologies or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate. For E3 ubiquitin ligase, exemplary sequences for GenBank: ACH72645.1 (*Homo sapiens*) include: MESGGRPSLC QFILLGTTSV VTAALYSVYR QKARVSQELK GAKKVHLGED LKSILSEAPG KCVPYAVIEG AVRSVKETLN SQFVENCKGV IQRLTLQEHK MVWNRTTHLW NDCSKIIHQR TNTVPFDLVP HEDGVDVAVR VLKPLDSVDL GLETVYEKFH PSIQSFTDVI GHYISGERPK GIQETEEMLK VGATLTGVGE LVLDNNSVRL QPPKQGMQYY LSSQDFDSLL QRQESSVRLW KVLALVFGFA TCATLFFILR KQYLQRQERL RLKQMQEEFQ EHEAQLLSRA KPEDRESLKS ACVVCLSSFK SCVFLECGHV CSCTECYRAL PEPKKCPICR QAITRVIPPY NS (SEQ ID NO: 1). For E3 ubiquitin ligase, exemplary sequences for GenBank: AAP47175.1 (*Homo sapiens*) include: MEEGNNNEEV IHLNNFHCHR GQEWINLRDG PITISDSSDE ERIPMLVTPA PQQHEEEDLD DDVILTETNK PQRSRPNLIK PAAQWQDLKR LGEERPKKSR AAFESDKSSY FSVCNNPLFD SGAQDDSEDD YGEFLDLGPP GISEFTKPSG QTEREPKPGP SHNQAANDIV NPRSEQKVII LEEGSLLYTE SDPLETQNQS SEDSETELLS NLGESAALAD DQAIEEDCWL DHPYFQSLNQ QPREITNQVV PQERQPEAEL GRLLFQHEFP GPAFPRPEPQ QGGISGPSSP QPAHPLGEFE DQQLASDDEE PGPAFPMQES QEPNLENIWG QEAAEVDQEL VELLVKETEA RFPDVANGFI EEIIHFKNYY DLNVLCNFLL ENPDYPKRED RIIINPSSSL LASQDETKLP KIDFFDYSKL TPLDQRCFIQ AADLLMADFK VLSSQDIKWA LHELKGHYAI TRKALSDAIK KWQELSPETS GKRKKRKQMN QYSYIDFKFE QGDIKIEKRM FFLENKRRHC RSYDRRALLP AVQQEQEFYE QKIKEMAEHE DFLLALQMNE EQYQKDGQLI ECRCCYGEFP FEELTQCADA HLFCKECLIR YAQEAVFGSG KLELSCMEGS CTCSFPTSEL EKVLPQTILY KYYERKAEEE VAAAYADELV RCPSCSFPAL LDSDVKRFSC PNPHCRKETC RKCQGLWKEH NGLTCEELAE KDDIKYRTSI EEKMTAARIR KCHKCGTGLI KSEGCNRMSC RCGAQMCYLC RVSINGYDHF CQHPRSPGAP CQECSRCSLW TDPTEDDEKL IEEIQKEAEE EQKRKNGENT FKRIGPPLEK PVEKVQRVEA LPRPVPQNLP QPQMPPYAFA HPPFPLPPVR PVFNNFPLNM GPIPAPYVPP LPNVRVNYDF GPIHMPLEHN LPMHFGPQPR HRF (SEQ ID NO: 2). For E3 ubiquitin ligase, exemplary sequences for GenBank: AAP47174.1 (*Homo sapiens*) include: MEEGNNNEEV IHLNNFHCHR GQEWINLRDG PITISDSSDE ERIPMLVTPA PQQHEEEDLD DDVILTEDDS EDDYGEFLDL GPPGISEFTK PSGQTEREPK PGPSHNQAAN DIVNPRSEQK VIILEEGSLL YTESDPLETQ NQSSEDSETE LLSNLGESAA LADDQAIEED CWLDHPYFQS LNQQPREITN QVVPQERQPE AELGRLLFQH EFPGPAFPRP EPQQGGISGP SSPQPAHPLG EFEDQQLASD DEEPGPAFPM QESQEPNLEN IWGQEAAEVD QELVELLVKE TEARFPDVAN GFIEEIIHFK NYYDLNVLCN FLLENPDYPK REDRIIINPS SSLLASQDET KLPKIDFFDY SKLTPLDQRC FIQAADLLMA DFKVLSSQDI KWALHELKGH YAITRKALSD AIKKWQELSP ETSGKRKKRK QMNQYSYIDF KFEQGDIKIE KRMFFLENKR RHCRSYDRRA LLPAVQQEQE FYEQKIKEMA EHEDFLLALQ MNEEQYQKDG QLIECRCCYG EFPFEELTQC ADAHLFCKEC LIRYAQEAVF GSGKLELSCM EGSCTCSFPT SELEKVLPQT ILYKYYERKA EEEVAAAYAD ELVRCPSCSF PALLDSDVKR FSCPNPHCRK ETCRKCQGLW KEHNGLTCEE LAEKDDIKYR TSIEEKMTAA RIRKCHKCGT GLIKSEGCNR MSCRCGAQMC YLCRVSINGY DHFCQHPRSP GAPCQECSRC SLWTDPTEDD EKLIEE- IQKE AEEEQKRKNG ENTFKRIGPP LEKPVEKVQR VEALPRPVPQ NLPQPQMPPY AFAHPPFPLP PVRPVFNNFP LNMGPIPAPY VPPLPNVRVN YDFG- PIHMPL EHNLPMHFGP QPRHRF (SEQ ID NO: 3).

The term "ubiquitin RPN13 receptor," "26S Proteasome regulatory subunit Rpn13," or "Proteasomal ubiquitin receptor ADRM1" refers to a protein encoded by the ADRM1 gene. For ubiquitin RPN13 receptor, exemplary sequences for GenBank: NP_783163.1 (*Homo sapiens* proteasomal ubiquitin receptor ADRM1 isoform 1) include: MTTSGALFPS LVPGSRGASN KYLVEFRAGK MSLKGTTVTP DKRKGLVYIQ QTDDSLIHFC WKDRTSGNVE DDLIIFPDDC EFKRVPQCPS GRVYVLKFKA GSKRLFFWMQ EPKTDQDEEH CRKVNEYLNN PPMPGALGAS GSSGHELSAL GGEG- GLQSLL GNMSHSQLMQ LIGPAGLGGL GGL- GALTGPG LASLLGSSGP PGSSSSSSSR SQSAAVTPSS TTSSTRATPA PSAPAAASAT SPSPAPSSGN GASTAASPTQ PIQLSDLQSI LATMNVPAGP AGGQQVDLAS VLTPEIMAPI LANADVQERL LPYLPSGESL PQTADEIQNT LTSPQFQQAL GMFSAALASG QLGPLMCQFG LPAEAVEAAN KGD- VEAFAKA MQNNAKPEQK EGDTKDKKDE EEDMSLD (SEQ ID NO: 4). For ubiquitin RPN13 receptor, exemplary sequences for GenBank: NP_001268367.1 (*Homo sapiens* proteasomal ubiquitin receptor ADRM1 isoform 2) include: MTTSGALFPS LVPGSRGASN KYLVEFRAGK MSLKGTTVTP DKRKGLVYIQ QTDDSLIHFC WKDRTSGNVE DEPKTDQDEE HCRKVNEYLN NPPMPGALGA SGSSGHELSA LGGEGGLQSL LGNMSHSQLM QLIGPAGLGG LGGLGALTGP GLASLLGSSG PPGSSSSSSS RSQSAAVTPS STTSSTRATP APSAPAAASA TSPSPAPSSGN- GASTAASPT QPIQLSDLQS ILATMNVPAG PAGGQQVDLA SVLTPEIMAP ILANADVQER LLPYLPSGES LPQTADEIQN TLTSPQFQQA LGMFSAALAS GQLGPLMCQF GLPAEAVEAA NKGD- VEAFAK AMQNNAKPEQ KEGDTKDKKD EEEDMSLD (SEQ ID NO: 5). The ubiquitin RPN13 receptor is a subunit of the 19S proteasome complex. The 19S regulatory particle is one of two distinct sub-complexes of the 26S proteasome, the other one being a 20S core particle. Exemplary sequences for GenBank: AAB61616.1 (*Homo sapiens* 26S proteasome regulatory subunit) include: MADPRDKALQ DYRKKLLEHK EIDGRLKELR EQLKELTKQY EKSENDLKAL QSVGQIVGEV LKQLTEEKFI VKATNGPRYV VGCRRQLDKS KLKPGTRVAL DMT- TLTIMRY LPREVDPLVY NMSHEDPGNV SYSEIG- GLSE QIRELREVIE LPLTNPELFQ RVGIIPPKGC LLY- GPPGTGK TLLARAVASQ LDCNFLKVVS SSIVDKYIGE SARLIREMFN YARDHQPCII FMDEID- AIGG RRFSEGTSAD REIQRTLMEL LNQMDGFDTL HRVKMIMATN RPDTLDPALL RPGRLDRKIH IDLP- NEQARL DILKIHAGPI TKHGEIDYEA IVKLSDGFNG ADLRNVCTEA GMFAIRADHD FVVQEDFMKA VRK- VADSKKL ESKLDYKPV (SEQ ID NO: 6).

The term "binder" refers to a compound that binds to a protein. The binder binds to a protein with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

The term "proteasome" refers to a multisubunit enzyme complex that plays a key role regulating proteins that control cell-cycle progression and apoptosis. The proteasome conducts proteolysis of selected proteins.

BRIEF DESCRIPTION OF THE DRAWINGS

FIG. 1A shows the use of a RPN13 small molecule inhibitor (RA190) design in conjunction with a moiety based on an immunomodulatory imide drug (iMiD), which is an ImiD-based degrader, to induce RPN13 degradation. FIG. 1B shows the use of RA190 as a covalent inhibitor of RPN13, and an ImiD-based degrader for binding an E3 ligase (e.g., cereblon (CRBN)).

FIG. 2 also shows the structures of exemplary bifunctional compounds

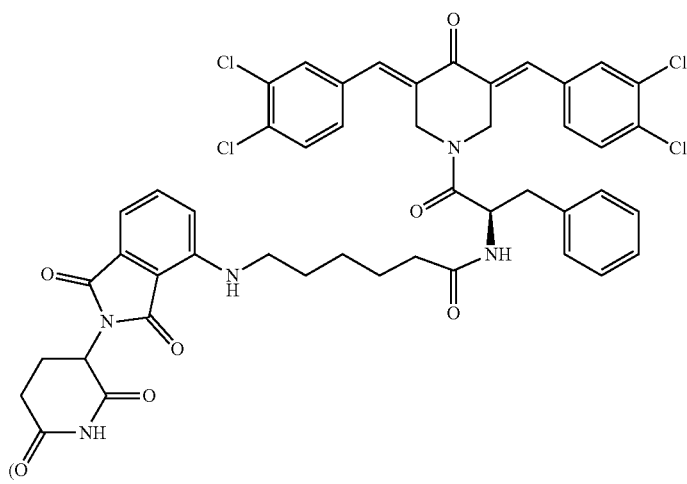

WL4 or WL-4 or JQRA

),

-continued

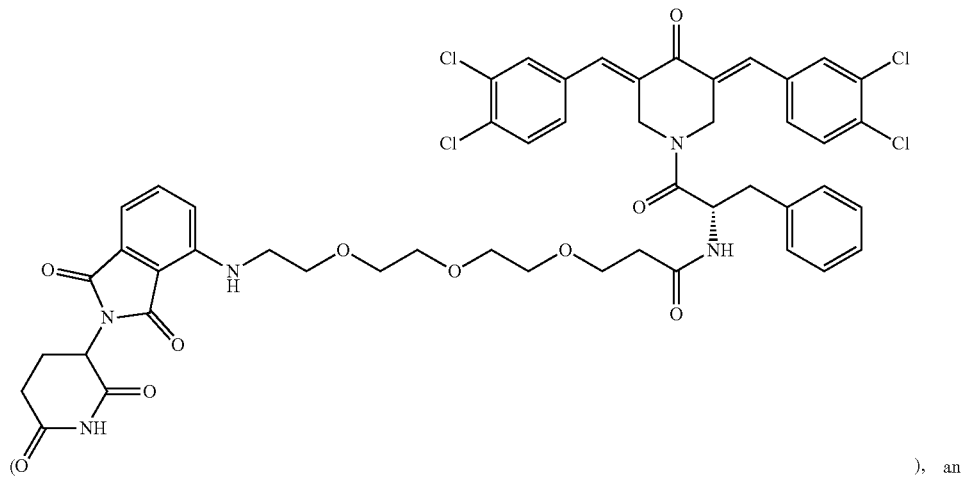

WL40 or WL-40

), and

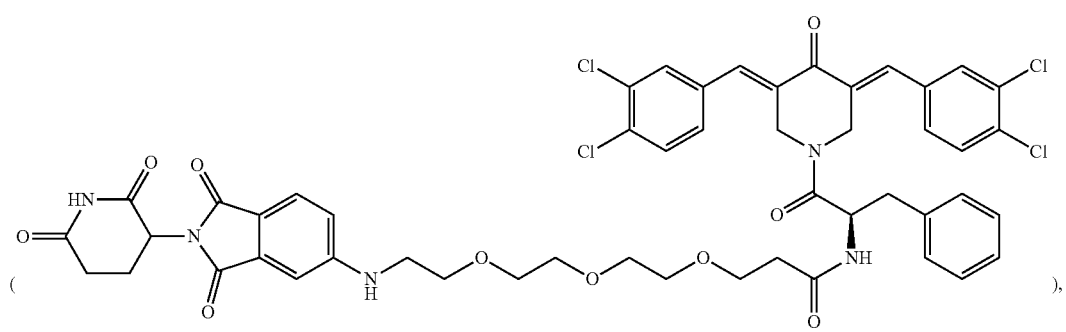

WL44

Figure 1A:
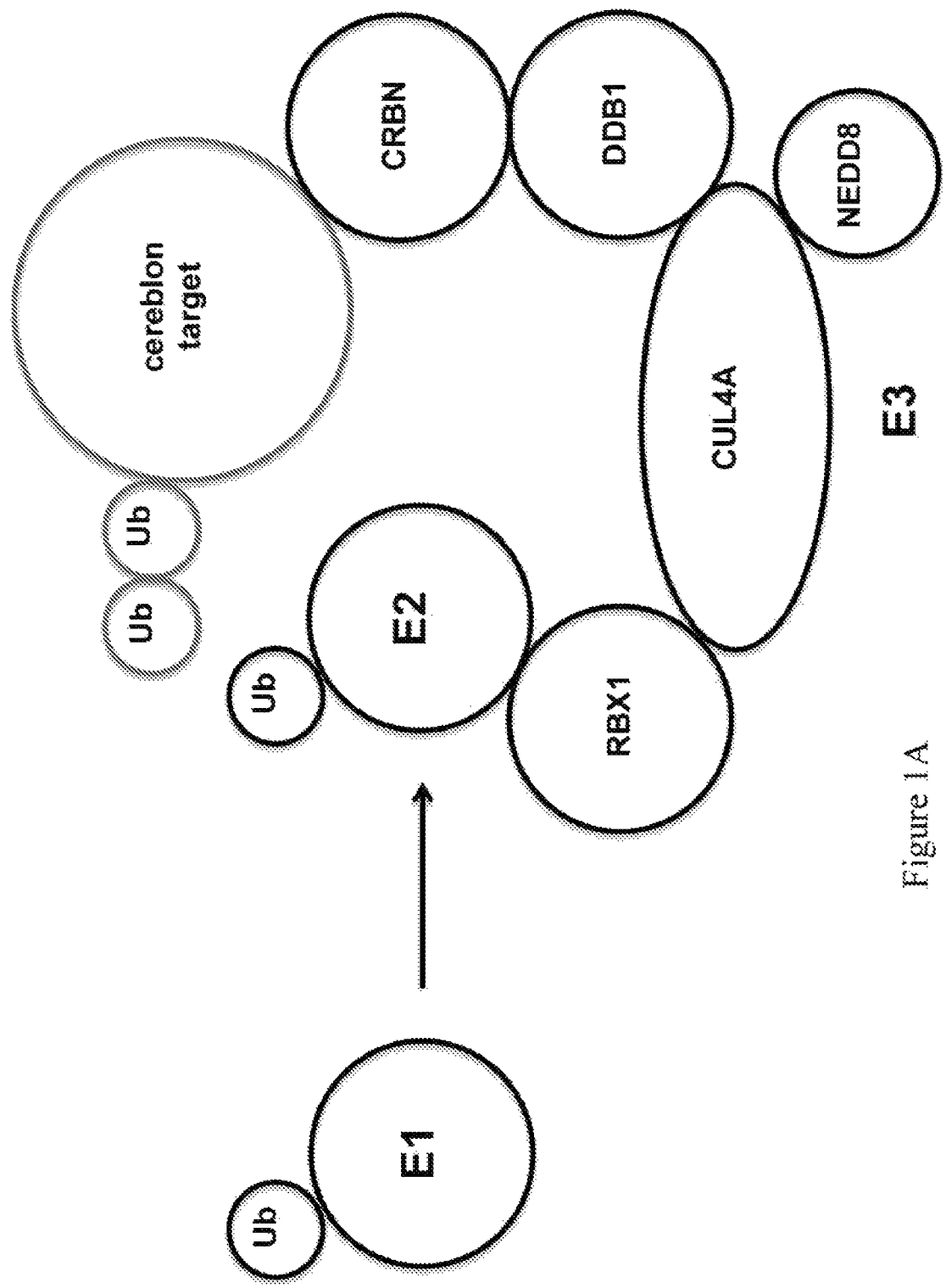
FIGS. 1A and 1B show the design principle behind the bifunctional compounds described herein.
Figure 1B:
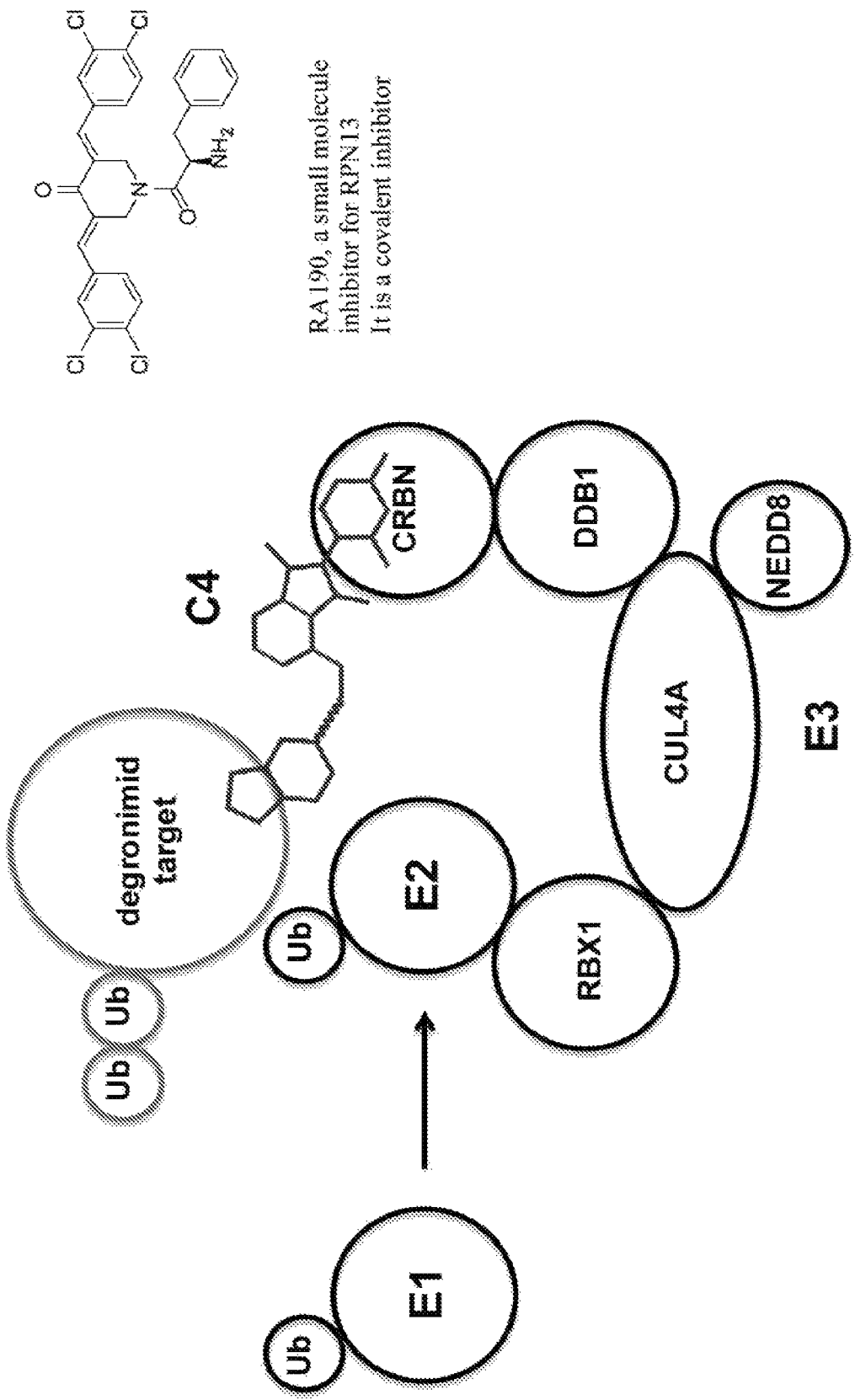
Figure 2:
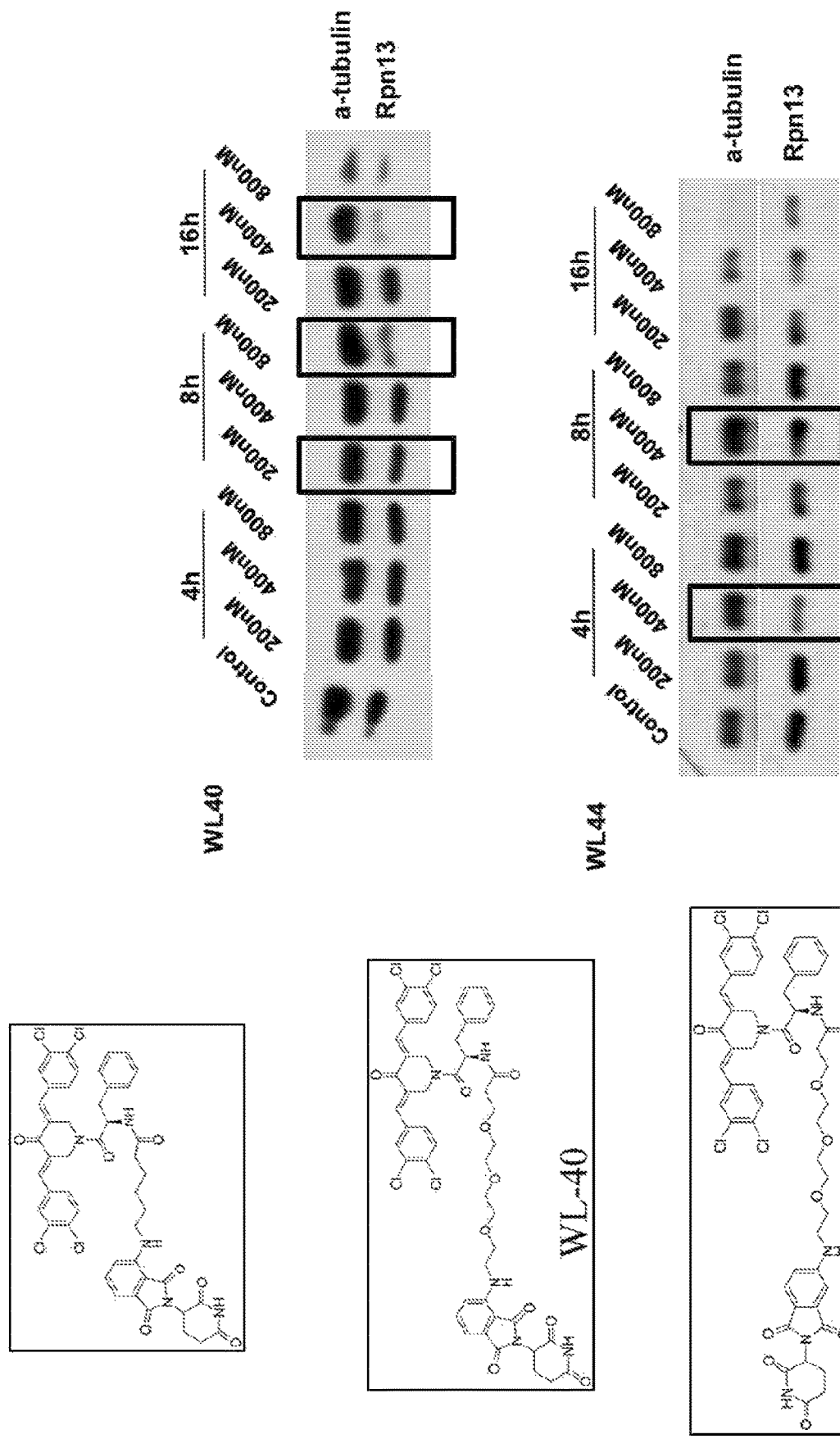
FIG. 2 shows MM.1S cells treated with WL40 or WL44 at 200 nM and 400 nM for 4 hours; treated with WL40 or WL44 at 200 nM, 400 nM, and 800 nM for 8 hours; and treated with WL40 or WL44 at 200 nM, 400 nM, and 800 nM for 16 hours. Protein lysates were loaded on SDS-PAGE and transferred to PVDF membrane, and then immunoblotted with anti-alpha tubulin and Rpn13 antibodies. Western blots show that exemplary bifunctional compounds WL40 and WL44 degrade Rpn13.
Figure 3:
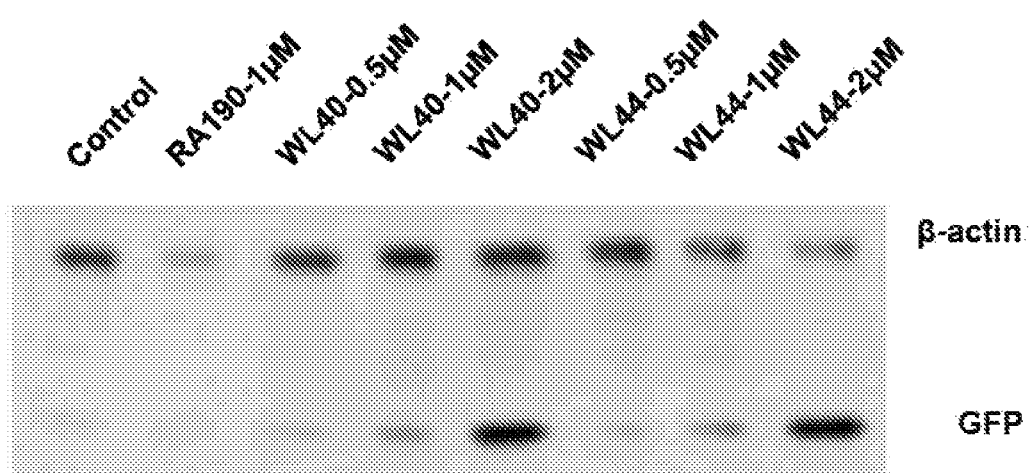

),

FIG. 3 shows a reporter cell line expressing Ub-tagged GFP that is constitutively targeted for proteasomal degradation treated with RA190 (1 μM); WL40 (0.5 μM, 1.0 μM, and 2.0 μM); and WL44 (0.5 μM, 1.0 μM, and 2.0 μM) for 16 hours. Cell lysates were loaded on SDS-PAGE, transferred to PVDF membrane, then immunoblotted with anti-GFP, and anti beta-actin antibodies. The blots show that exemplary bifunctional compounds WL40 and WL44 block proteasome function.

Figure 4A:
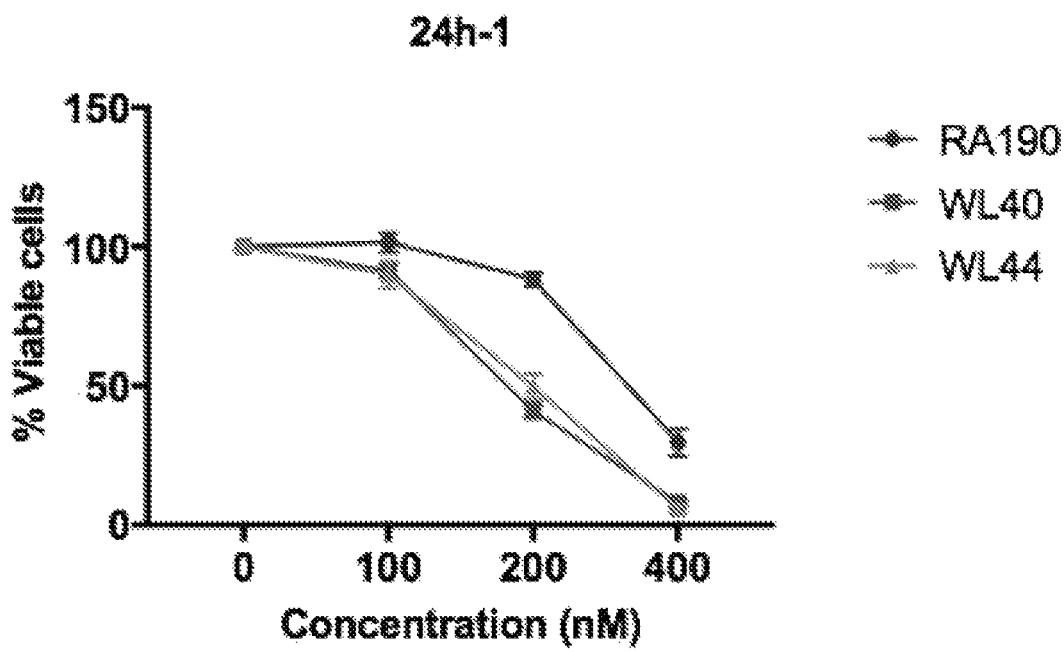
Figure 4B:
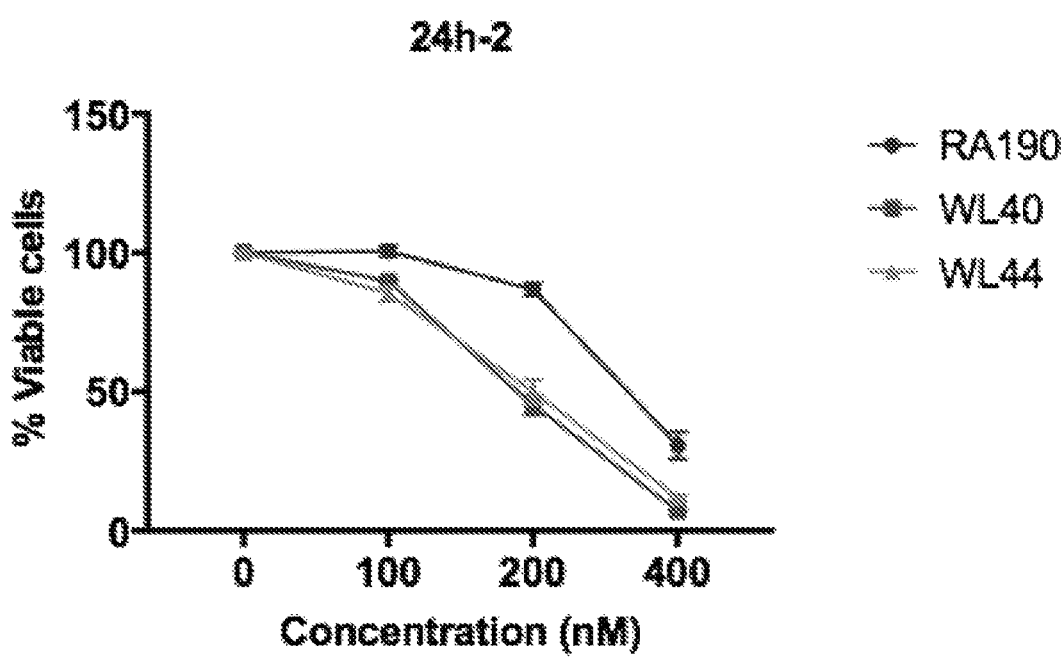

FIGS. 4A and 4B show multiple myeloma 1S (MM.1S) cells treated with RA190, WL40, and WL44 at the indicated concentrations for 24 hours. Wst-1 assay was used to test cell viability. FIGS. 4A and 4B show that exemplary bifunctional compounds WL40 and WL44 decrease multiple myeloma 1S cell viability with lower $IC_{50}$ compared to compound RA190.

Figure 5A:
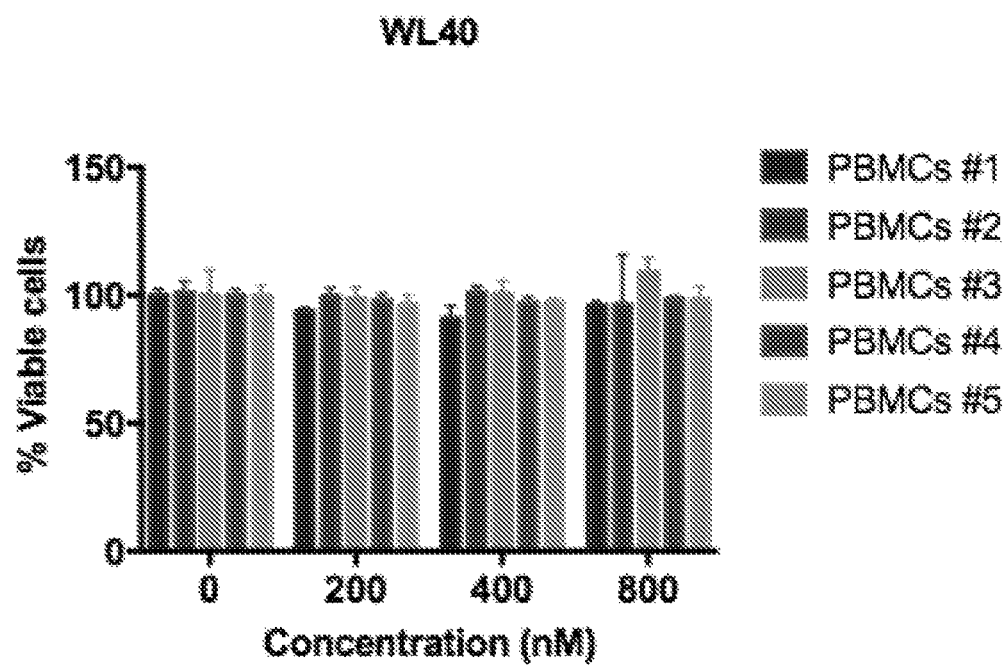
Figure 5B:
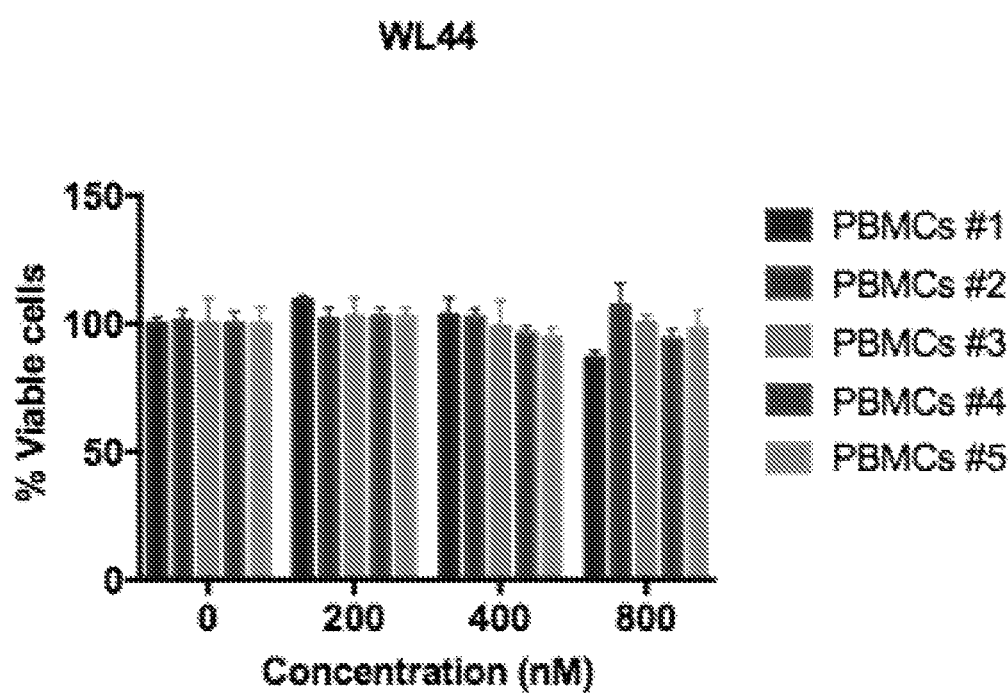

FIGS. 5A and 5B show PBMCs from normal healthy donor treated with WL40 and WL44 at the indicated concentrations for 48 hours. Wst-1 assay was used to test cell viability. FIGS. 5A and 5B show that exemplary bifunctional compounds WL40 (FIG. 5A) and WL44 (FIG. 5B) at the $IC_{50}$ do not significantly affect the viability of normal peripheral blood mononuclear cells (PBMC's).

Figure 6A:
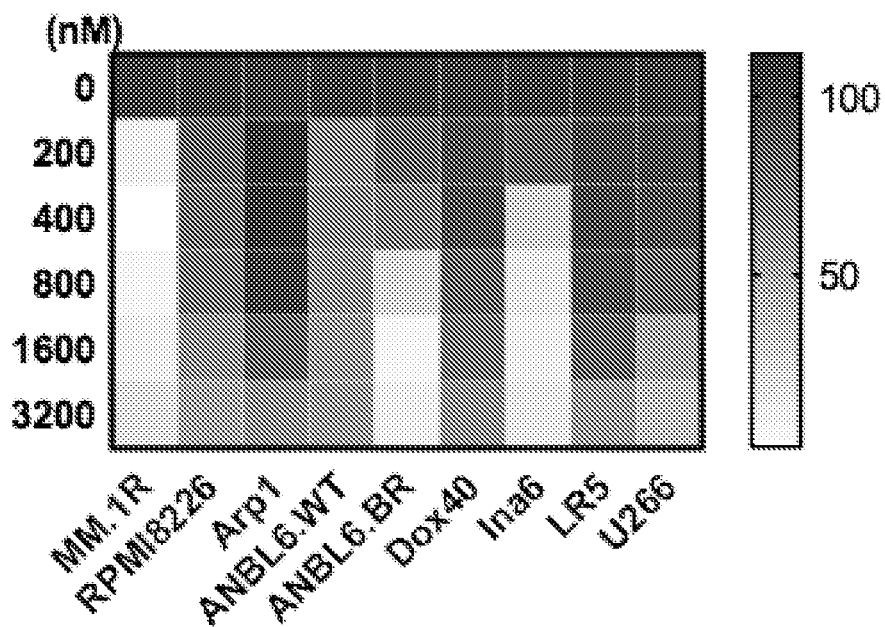
Figure 6B:
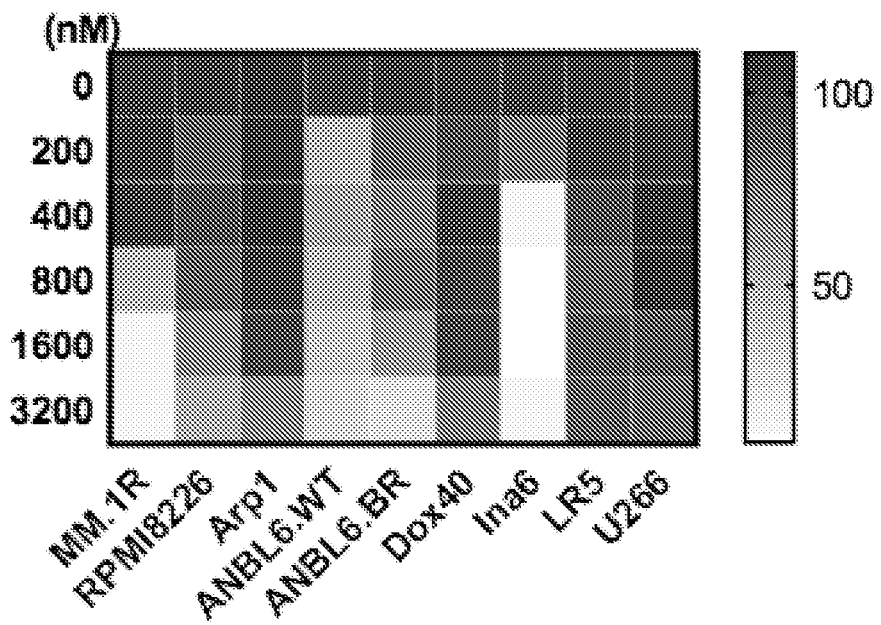

FIGS. 6A and 6B show multiple myeloma cell lines treated with WL40 or WL44 at the indicated concentrations for 48 hours. Wst-1 assay was used to test cell viability. FIGS. 6A and 6B show the effect of exemplary bifunctional compounds WL40 and WL44 on multiple myeloma cell lines. Exemplary bifunctional compounds WL40 (FIG. 6A) and WL44 (FIG. 6B) have a high $IC_{50}$ in several cell lines.

Figure 7A:
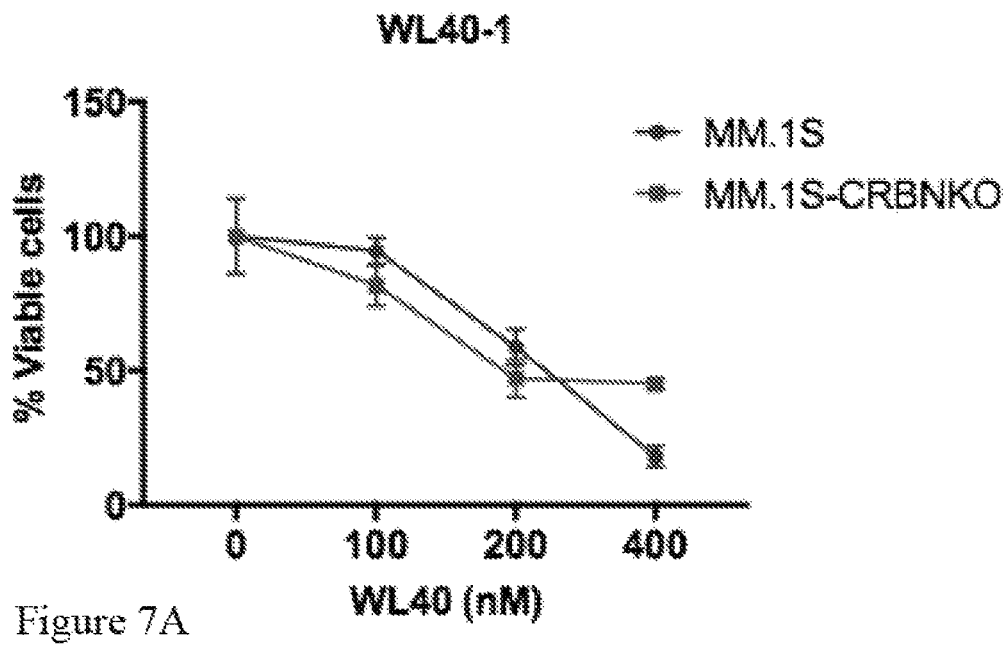
Figure 7B:
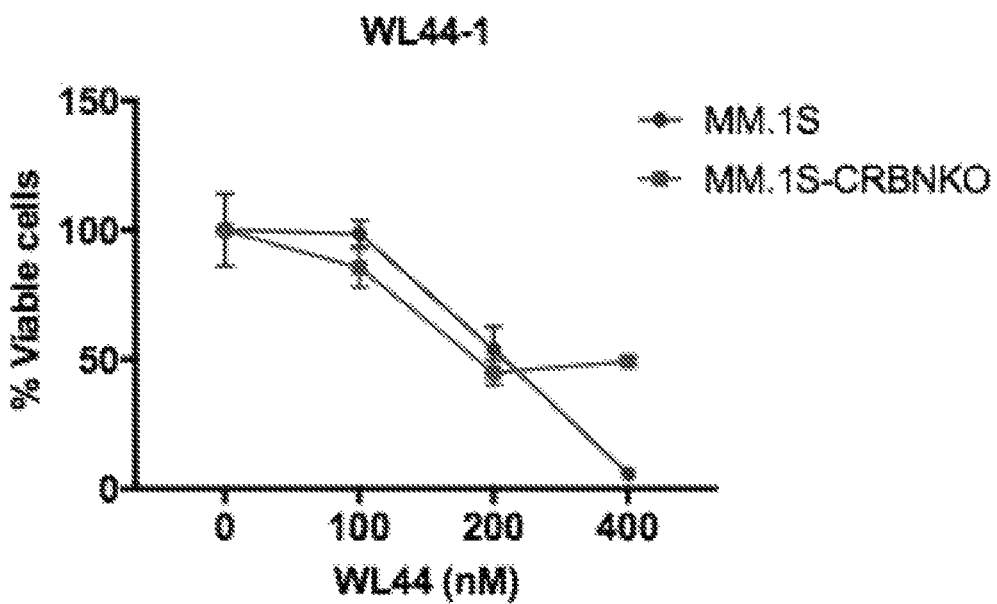

FIGS. 7A and 7B show MM.1S and MM.1S CRBN KO (multiple myeloma 1S-cereblon knockout) cell lines were treated with WL40 or WL44 at the indicated concentrations for 24 hours. Wst-1 assay was used to test cell viability. FIGS. 7A and 7B show that exemplary bifunctional compounds WL40 (FIG. 7A) and WL44 (FIG. 7B) decrease cell viability in the multiple myleoma cell line 1S-cereblon knockout (MM.1S-CRBN KO).

Figure 8A:
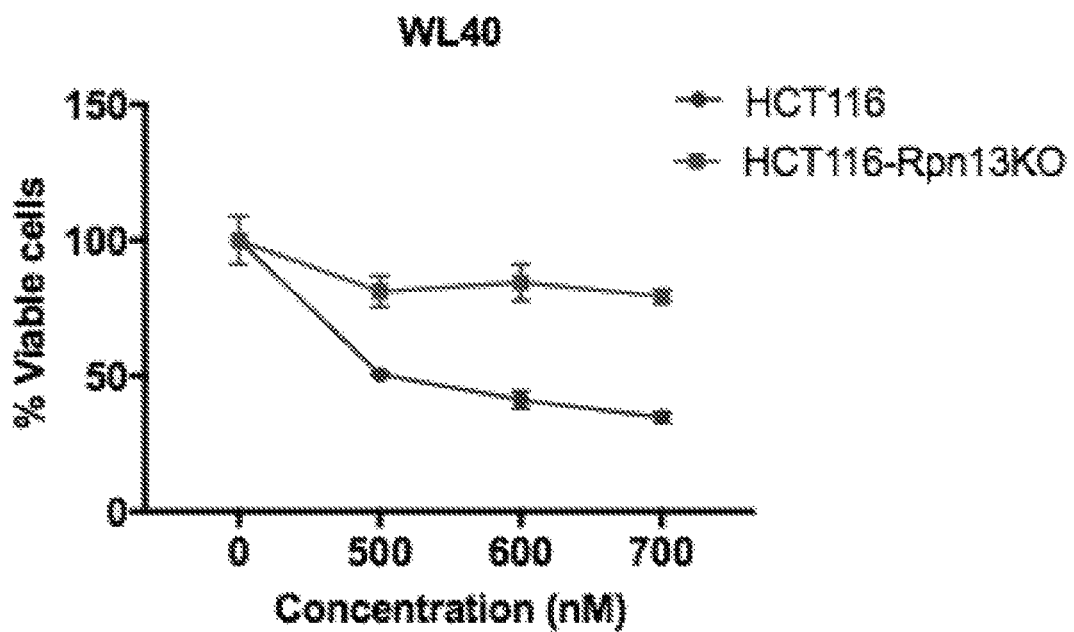
Figure 8B:
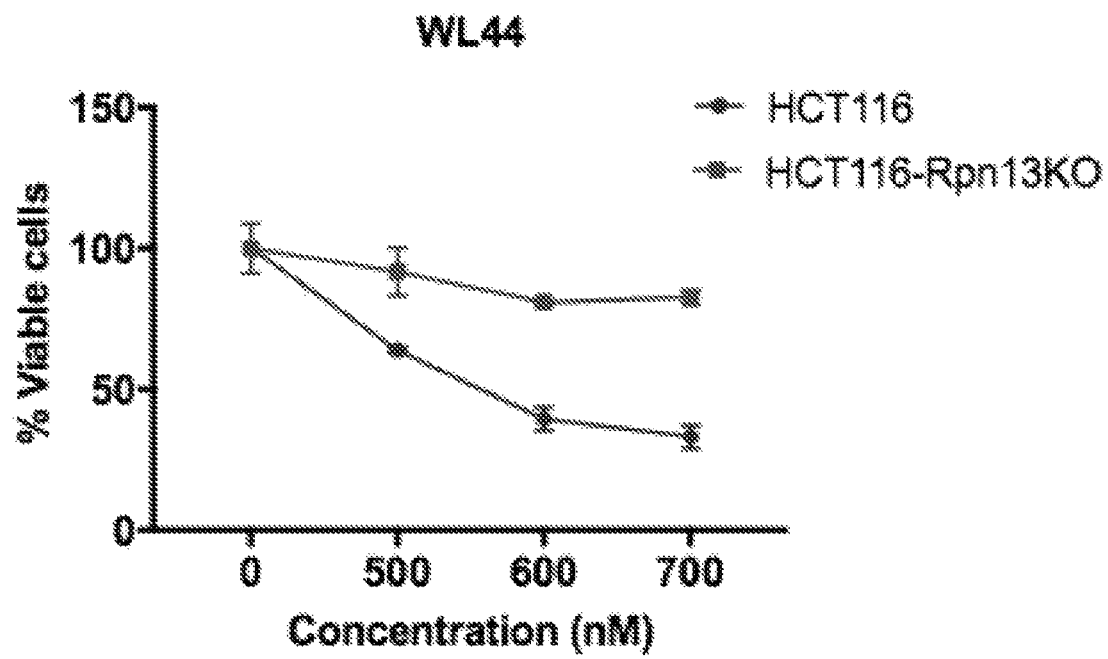

FIGS. 8A and 8B show HCT116 and HCT116-Rpn13KO cell lines that were treated with WL40 or WL44 at the indicated concentrations for 48 hours. Wst-1 assay was used to test cell viability. FIGS. 8A and 8B show that the cytotoxicity of exemplary bifunctional compounds WL40 (FIG. 8A) and WL44 (FIG. 8B) is RPN13-dependent.

Figure 9A:
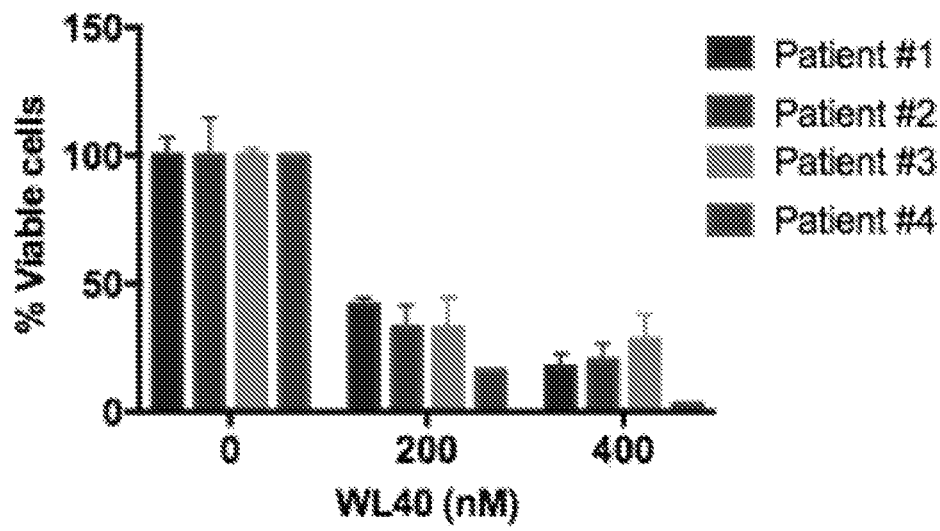
Figure 9B:
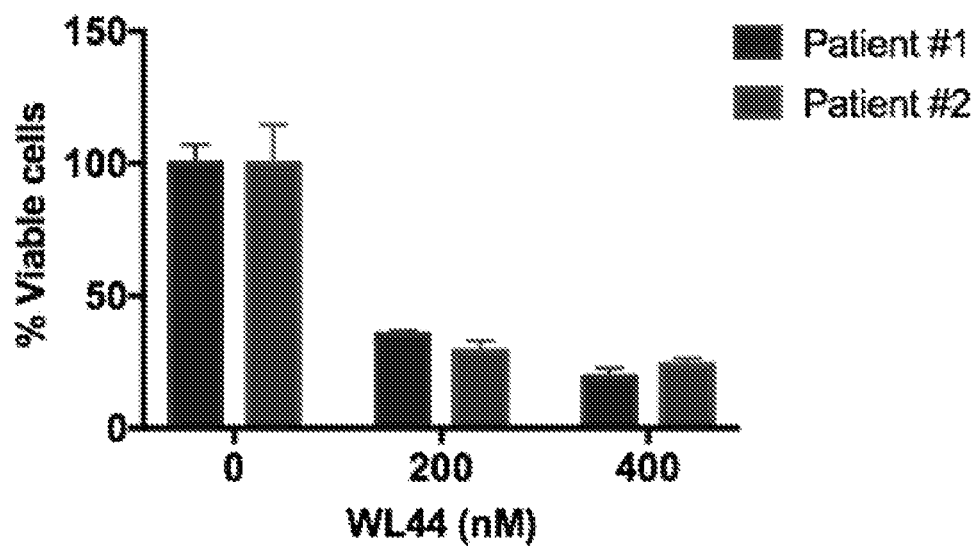

FIGS. 9A and 9B show CD138+MM cells from patients that were treated with WL40 or WL44 at the indicated concentrations for 48 hours. CTG assay was used to test cell viability. FIGS. 9A and 9B show the effect of exemplary bifunctional compounds WL40 (FIG. 8A) and WL44 (FIG. 8B) at certain concentrations (nM) on the viability of cells in patients.

Figure 10:
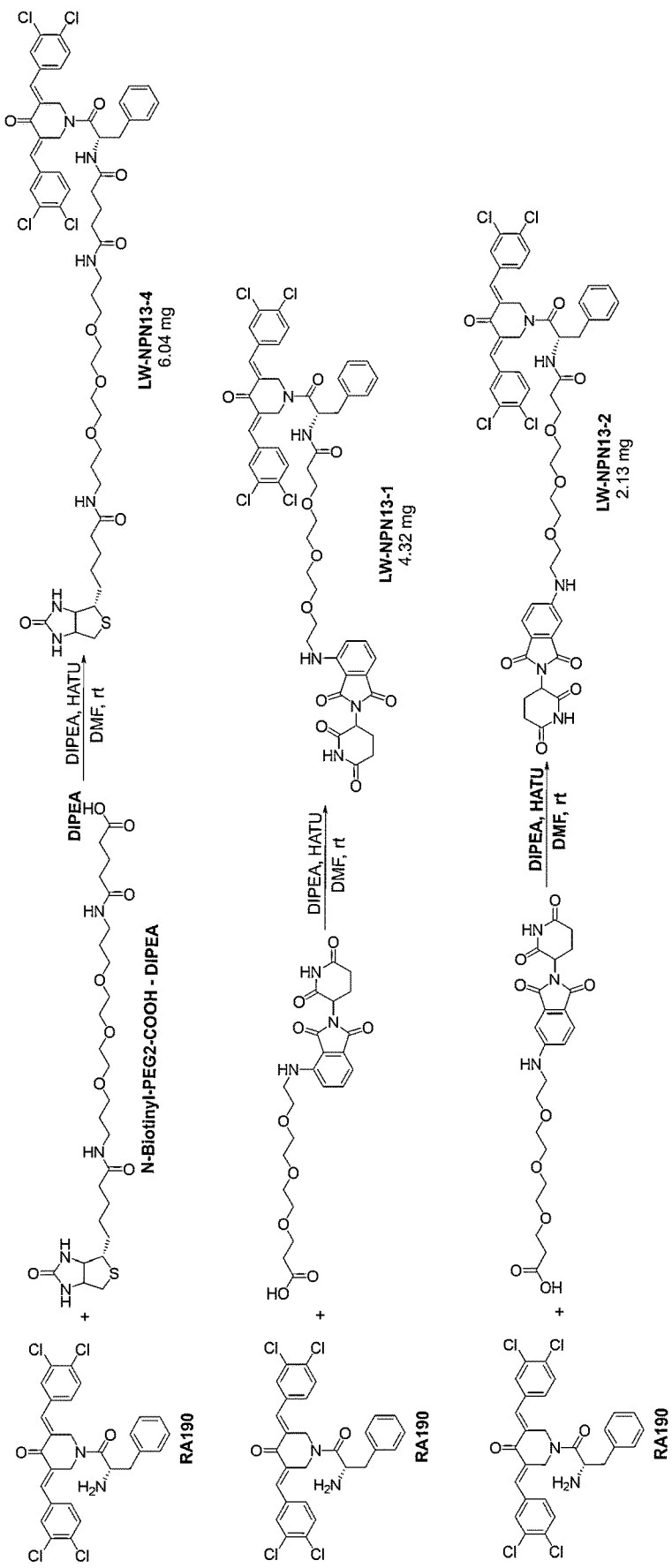

FIG. 10 shows the development of other exemplary bifunctional compounds which include degraders of RPN13.

Figure 11:
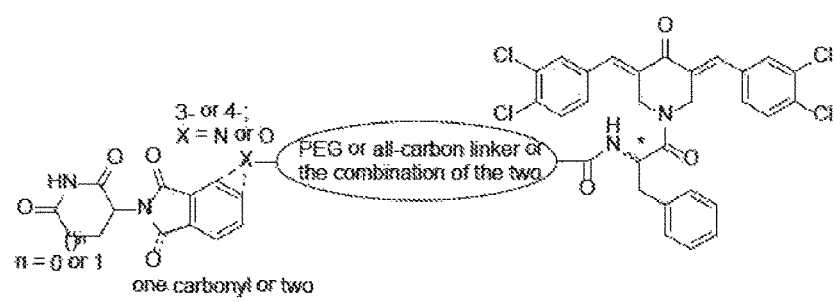

FIG. 11 shows a scheme of the development of the exemplary bifunctional compounds with the RPN13 probe molecule and degraders, including synthetic schemes.

Figure 12:
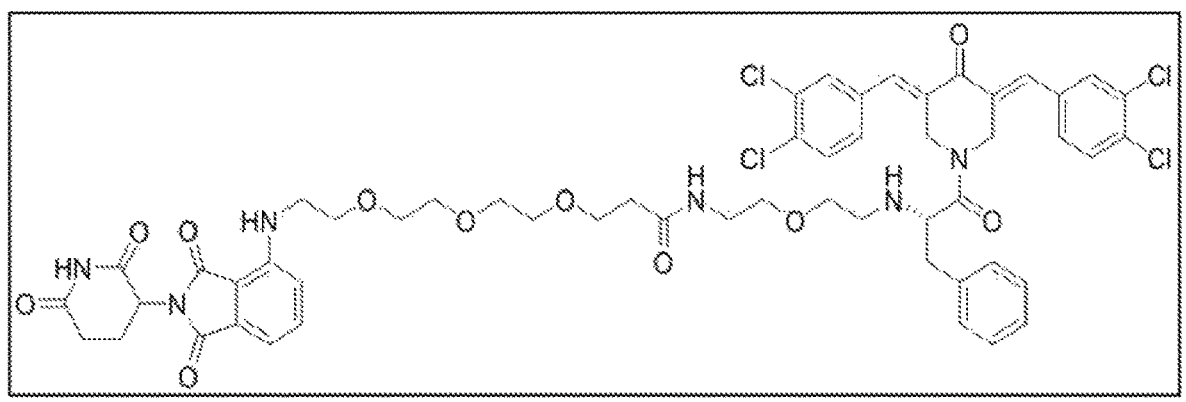

FIG. 12 shows the structure of exemplary compound dRPN13-3.

Figure 13A:
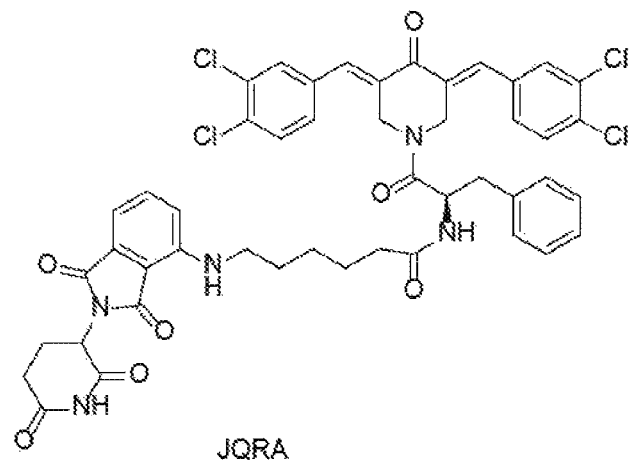
Figure 13B:
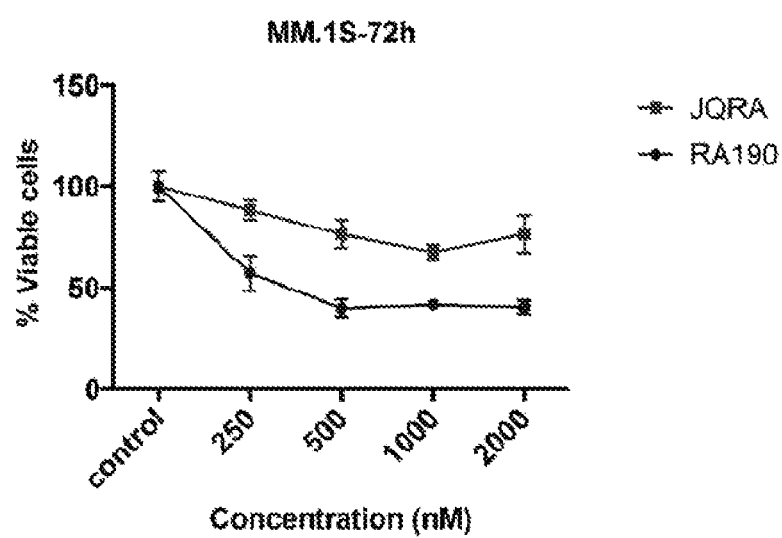

FIG. 13A and FIG. 13B show that RA190 induces stronger MM cytotoxicity compared to exemplary compound JQRA, and depict the structure of exemplary compound JQRA. FIG. 13A depicts the structure of exemplary compound JQRA. In FIG. 13B, multiple myeloma cells (MM.1S) were treated with RA190 or compound JQRA at the indicated concentrations for 72 hours, and the percentage of viable cells was measured.

Figure 14:
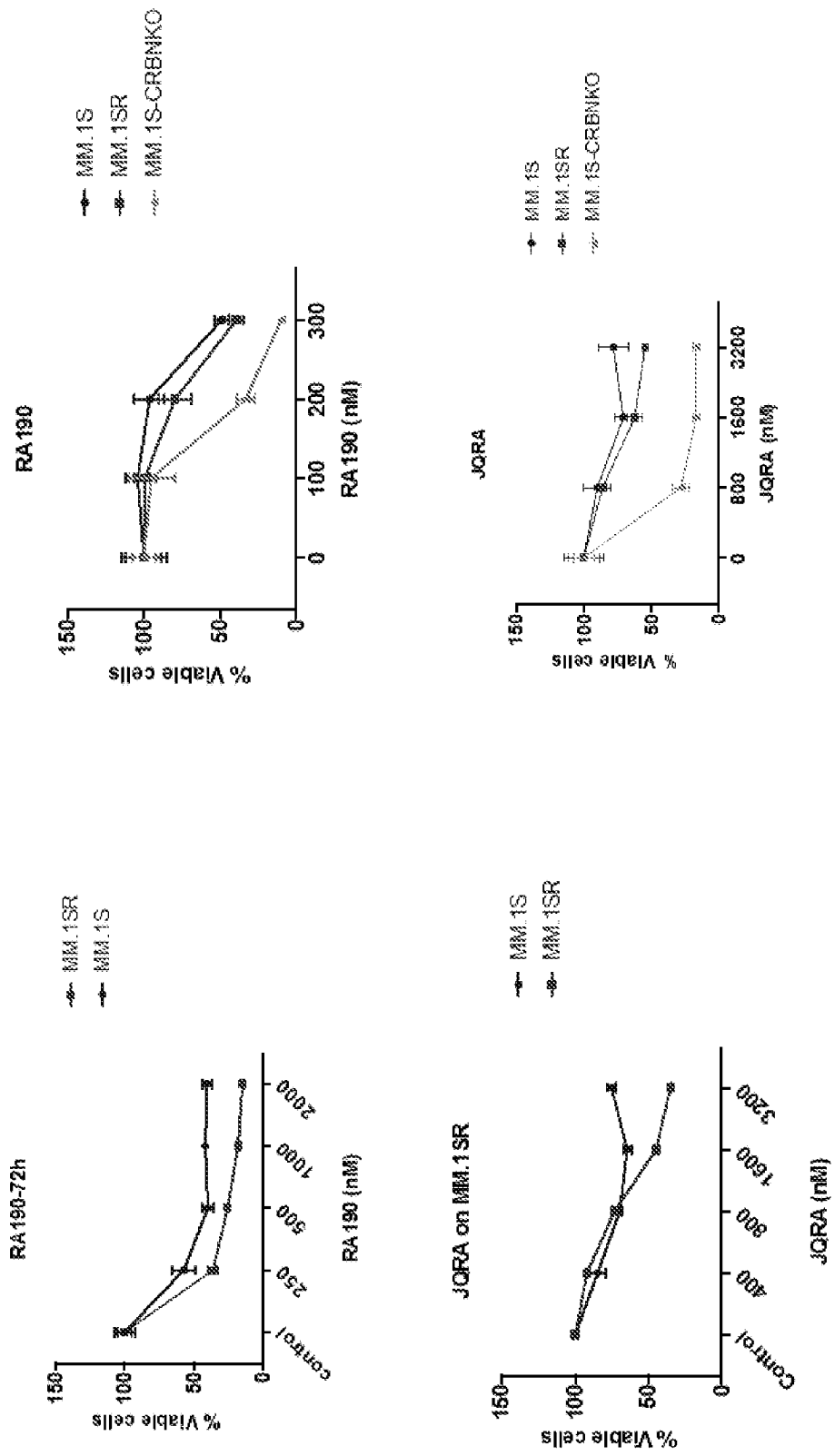

FIG. 14 shows that RA190 induced more robust MM cytotoxicity in MM.1S, MM.1S-len resistant, and CRBN-KO cells compared with exemplary compound JQRA. The experiment was repeated twice and JQRA concentration was increased (as indicated) at the second time. MM.1S Len-resistant (MM.1S lenalidomide resistant) cells are more sensitive to exemplary compound JQRA compared to wild type MM.1S. In FIG. 14, multiple myeloma cells (MM.1SRor MM.1S) were treated with RA190 or compound JQRA at the indicated concentrations for 72 hours, and the percentage of viable cells was measured.

Figure 15:
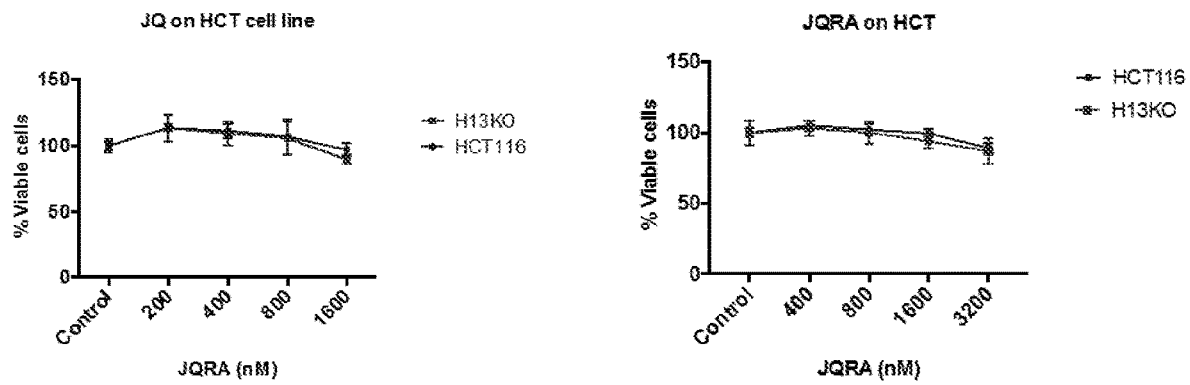

FIG. 15 shows that treatment with JQRA does not affect the percentage of viability of HCT116 and HCT-Rpn13KO cells. In FIG. 15, HCT116 and HCT-Rpn13KO cells were treated with JQRA for 72 hours, and the percentage of viable cells was measured.

Figure 16:
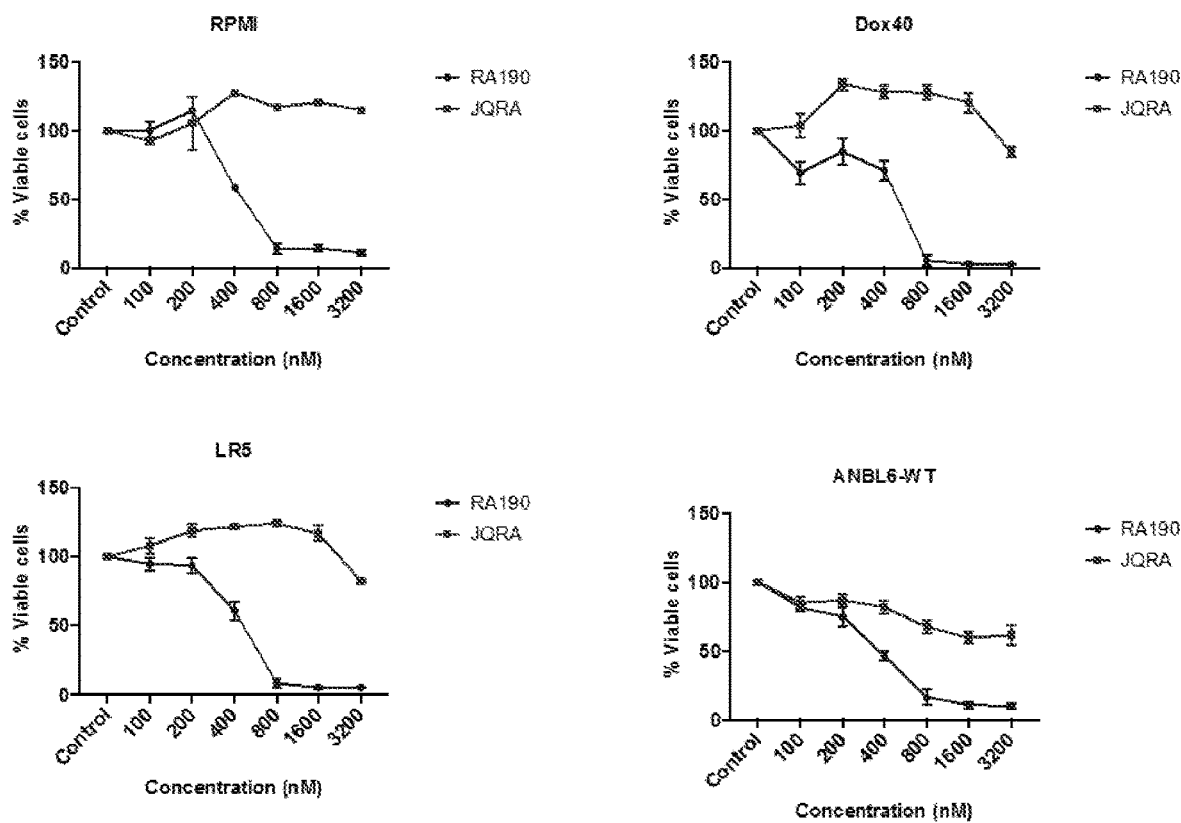

FIG. 16 shows that in the different indicated multiple myeloma cell lines, RA190 induces stronger cytotoxicity than JQRA. In FIG. 16, the MM.1S cell lines were treated with JQRA or RA190 for 72 hours, and the percentage of viable cells was measured at 72 hours.

Figure 17:
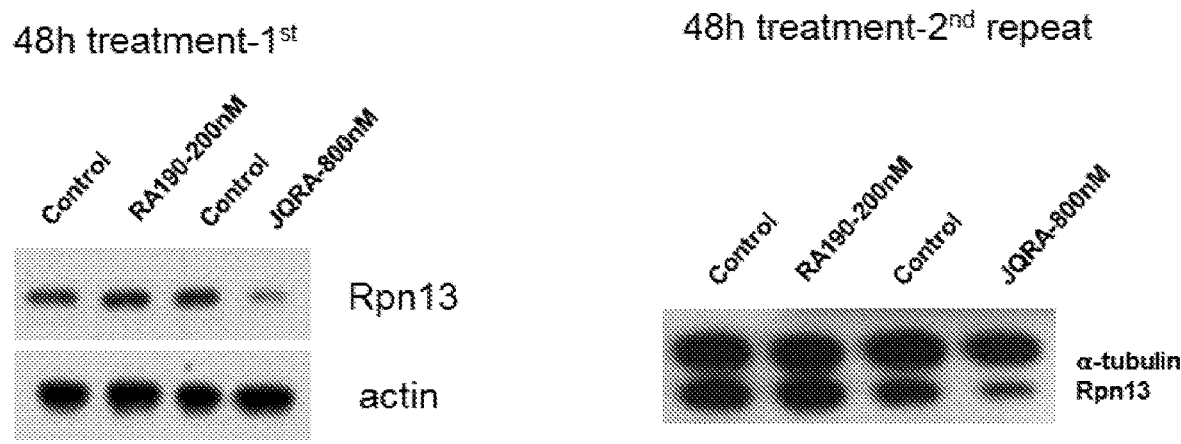

FIG. 17 shows that JQRA degrades RPN13 at a certain time point. In FIG. 17, MM.1S cells were treated with RA190 or JQRA at 200 nM and 400 nM, respectively, for 48 hours; and treated with RA190 or JQRA at 200 nM and 800 nM, respectively, for 48 hours. Protein lysates were loaded on SDS-PAGE and transferred to PVDF membrane, and then immunoblotted with anti-alpha tubulin and Rpn13 antibodies. Western blots show that exemplary bifunctional compound JQRA degrades RPN13.

Figure 18:
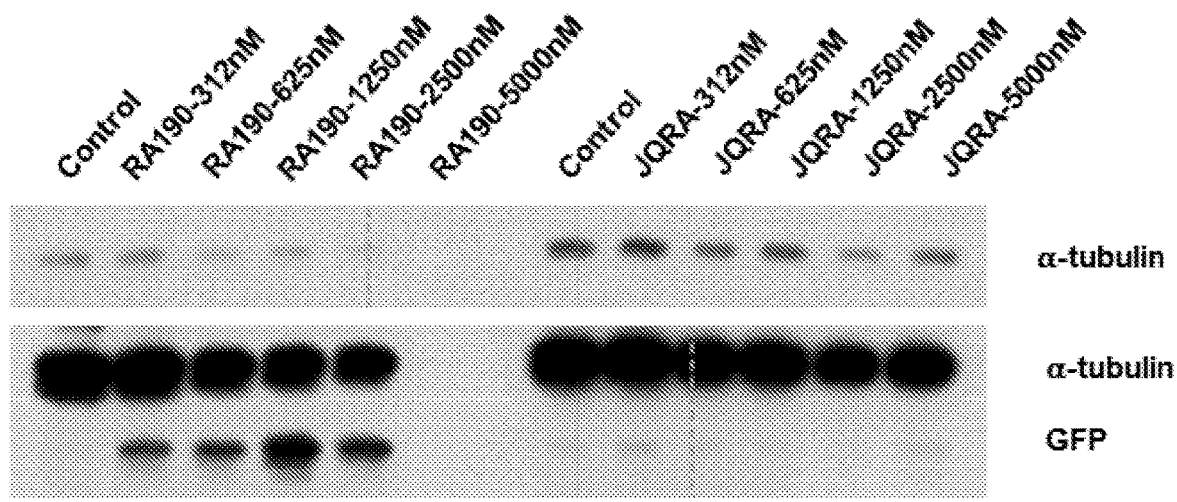

FIG. 18 shows that JQRA does not block proteasome function as RA190 does. In FIG. 18, a reporter cell line expressing Ub-tagged GFP that is constitutively targeted for proteasomal degradation was treated with RA190 (312 µM, 625 µM, 1250 µM, 2500 µM, 5000 µM); and JQRA (312 µM, 625 µM, 1250 µM, 2500 µM, 5000 µM) for 16 hours. Cell lysates were loaded on SDS-PAGE, transferred to PVDF membrane, then immunoblotted with anti-GFP, and anti-alpha tubulin antibodies. The blots show that exemplary bifunctional compound JQRA does not block proteasome function as RA190 blocks proteasome function.

Figure 19A:
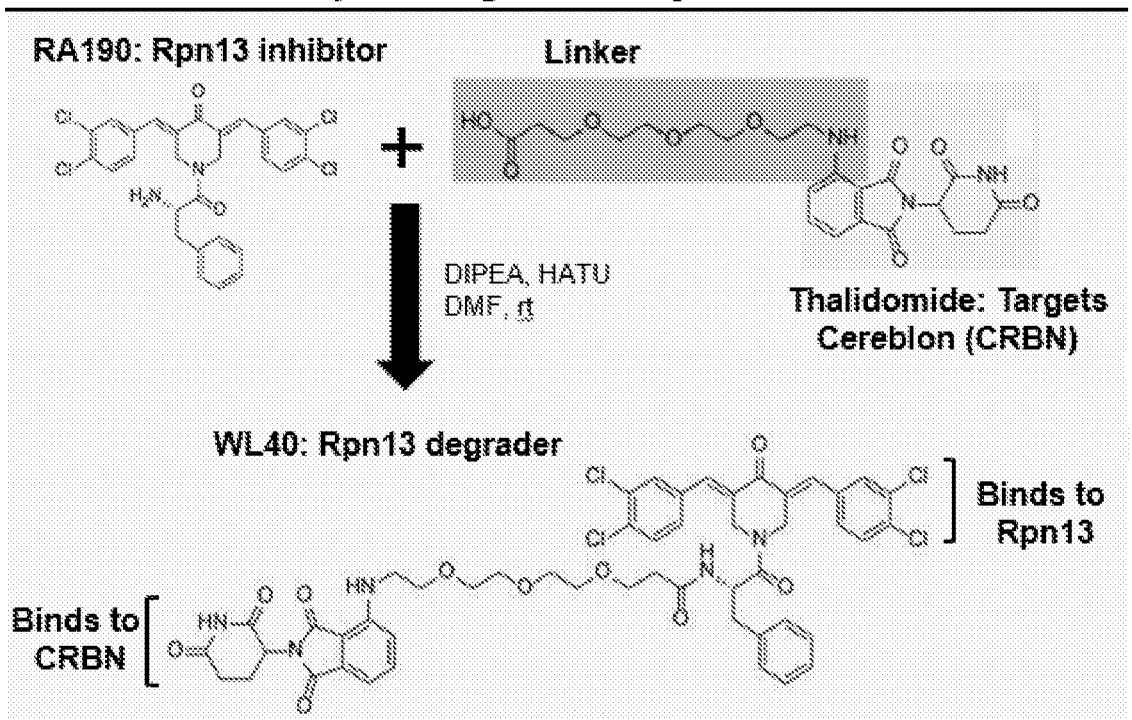
Figure 19B:
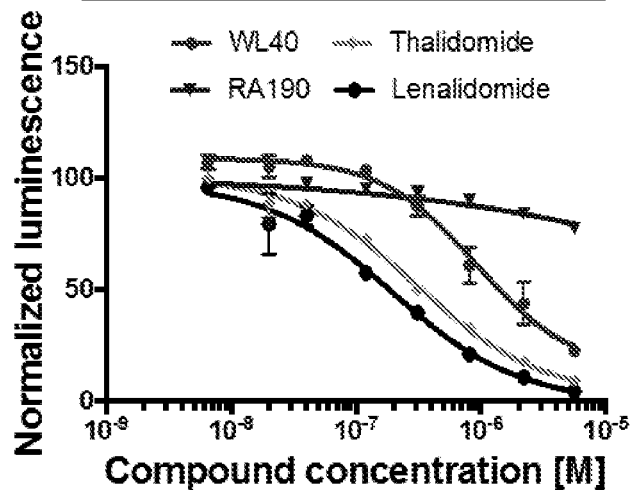
Figure 19C:
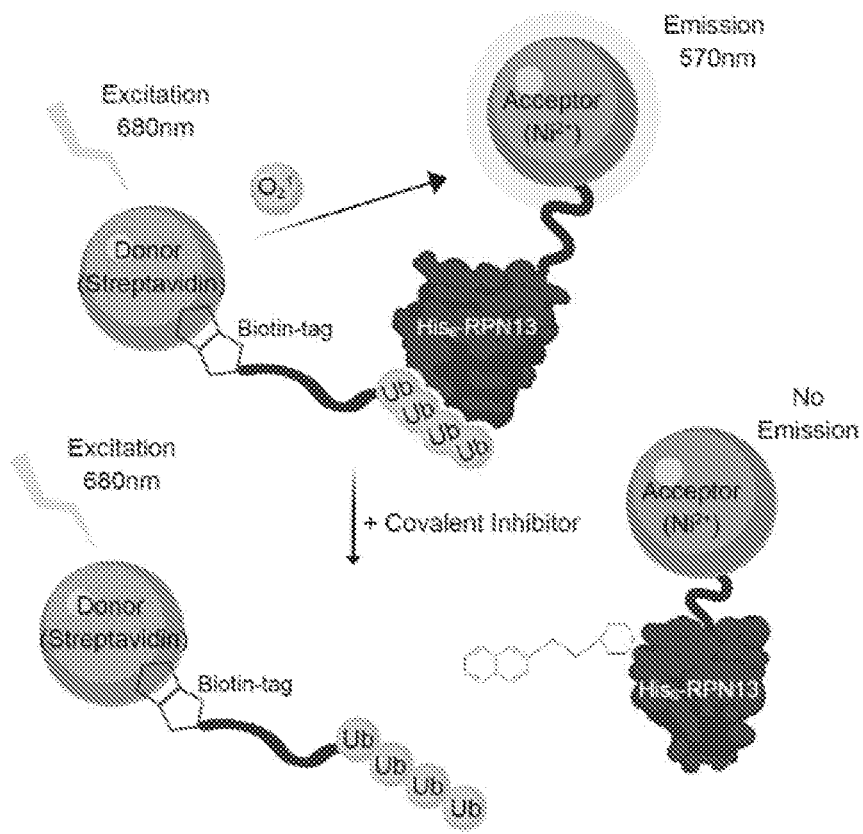
Figure 19D:
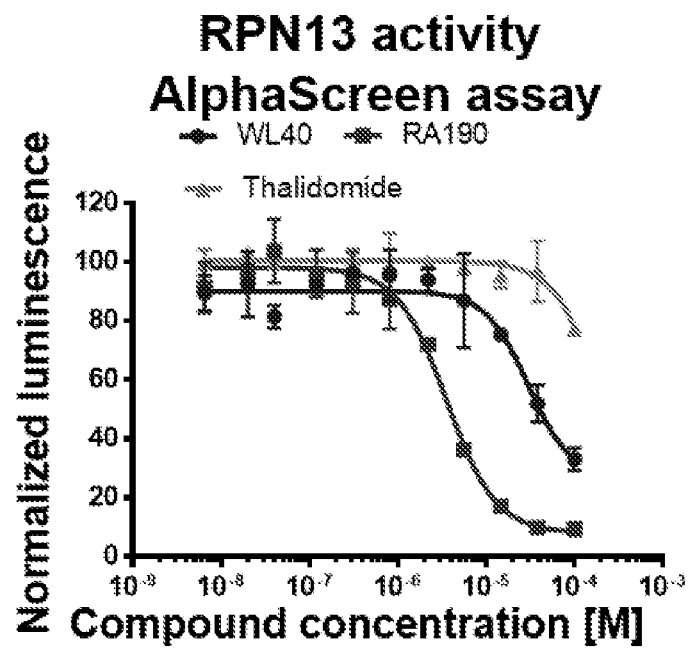
Figure 19E:
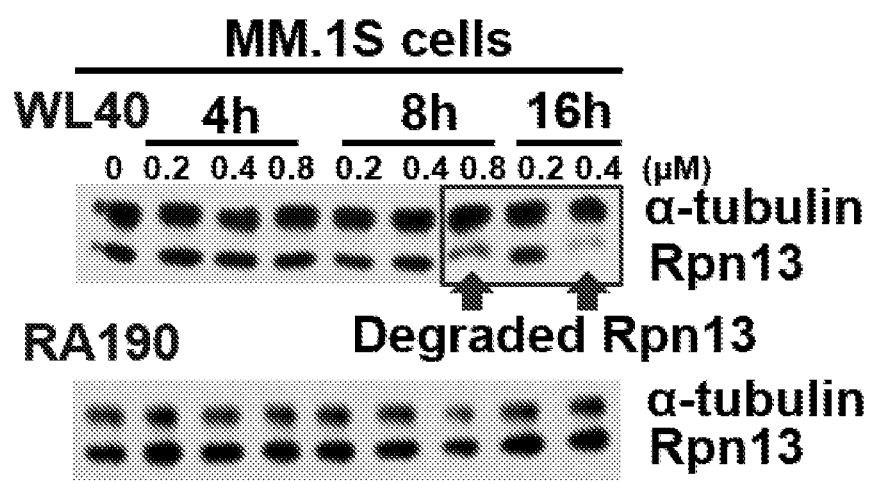
Figure 19F:
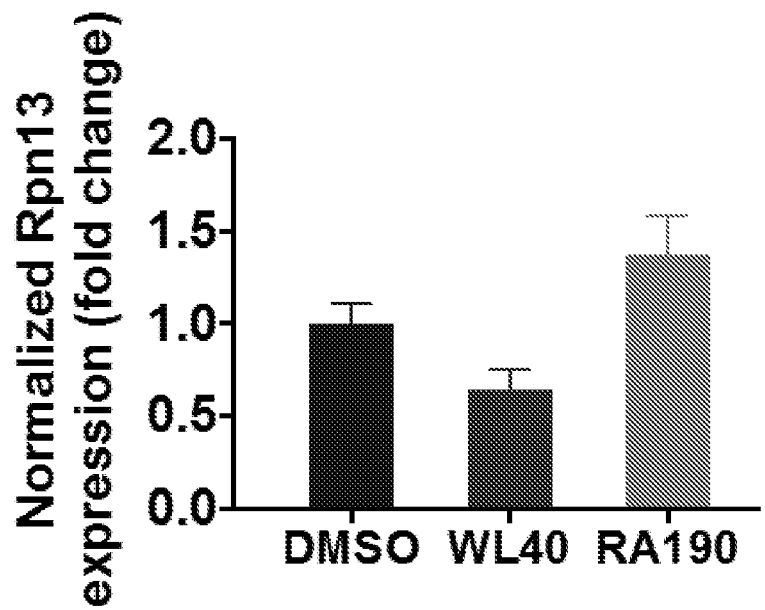
Figure 19G:
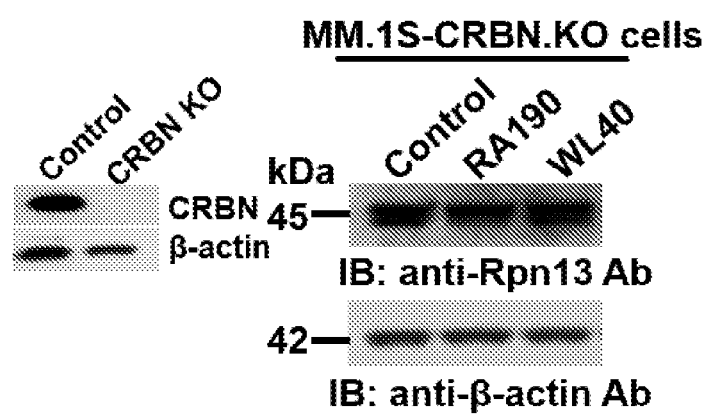
Figure 19H:
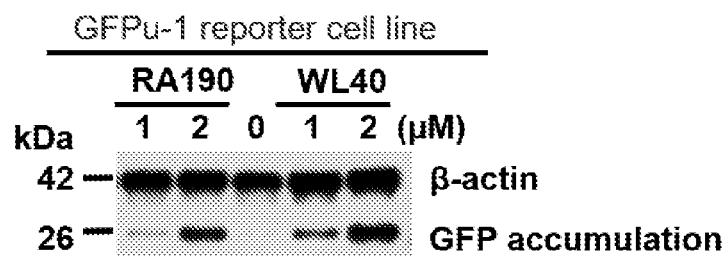
Figure 19I:
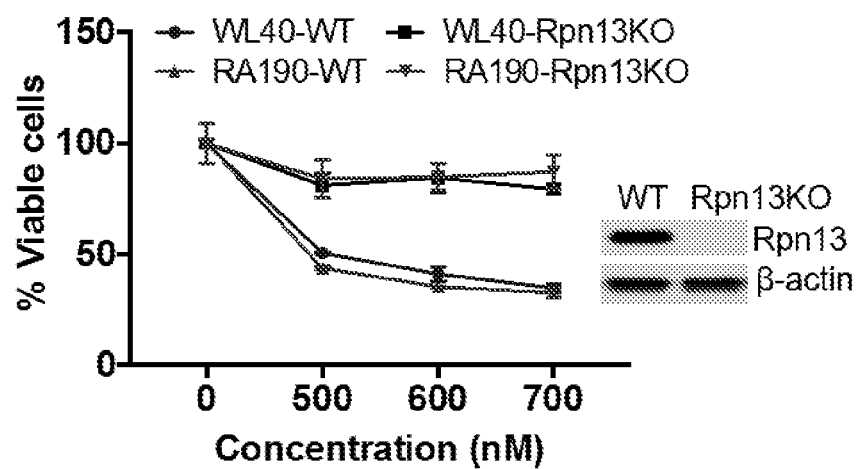

FIGS. 19A-19I show the exemplary design and characterization of exemplary Rpn13 degrader WL40. FIG. 19A shows the synthesis of WL40. WL40 was created by linking the Rpn13 inhibitor RA190 to the IMiD thalidomide as a ligand for the CRBN E3 ligase via a PEG linker. FIG. 19B shows results of a Cereblon AlphaScreen assay to measure the displacement of biotinylated-Pomalidomide probe (triplicate means±SD). FIG. 19C is a schematic cartoon for the novel AlphaScreen assay to measure the binding activity of inhibitor with RPN13 proteins. FIG. 19D shows the results of a RPN13 AlphaScreen assay to measure the binding activity of inhibitor with RPN13 proteins (triplicate means±SD). FIG. 19E depicts immunoblot analysis of multiple myeloma 1S (MM.1S) cells, which were treated with WL40 or RA190 at the indicated concentrations and time periods; protein lysates were subjected to the immunoblot analysis using anti-Rpn13 or anti-tubulin Abs. FIG. 19F depicts flow cytometry analysis of MM.1S cells, which were treated with DMSO control, WL40 (400 nM), or RA190 (500 nM) for 16 hours; cells were then washed and stained with Rpn13 Ab conjugated with AlexaFluor-647, followed by the flow cytometry analysis. Isotype Ab conjugated to AlexaFluor-647 was used as control for non-specific binding. Data was quantified using FACS Diva (BD Biosciences, USA) and FlowJo (FlowJo LLC, USA). FIG. 19G depicts immunoblot analysis of MM.1S-CRBN KO cells, which were treated with WL40 (400 nM) or RA190 (500 nM) for 16 hours; protein lysates were subjected to the immunoblot analysis using anti-Rpn13 or anti β-actin Abs. Insert: Protein lysates from MM.1S.WT control and MM.1S-CRBN KO cells were subjected to immunoblot analysis using anti-CRBN or anti-β-actin Abs. FIG. 19H is an immunoblot showing the levels of Ub-GFP accumulation in a GFPu-1 reporter cell line treated with indicated concentrations of WL40 and RA190 for 16 hours. Blots shown are representative of 3 independent experiments. FIG. 19I shows an assessment for cell viability of HCT116-WT and HCT116-CRISPR Rpn13KO cells, which were treated with WL40 or RA190 at the indicated concentrations for 48 hours, followed by the assessment of cell viability using WST assay (mean±SD; p<0.001; n=3). Insert: Protein lysates from Rpn13-WT and KO cells were subjected to immunoblot analysis using anti-Rpn13 or β-actin Abs.

Figure 20A:
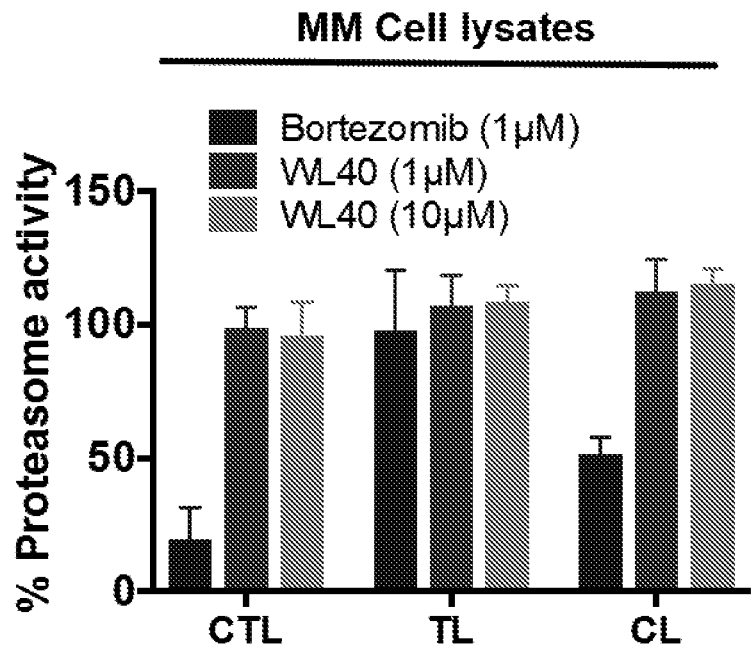
Figure 20B:
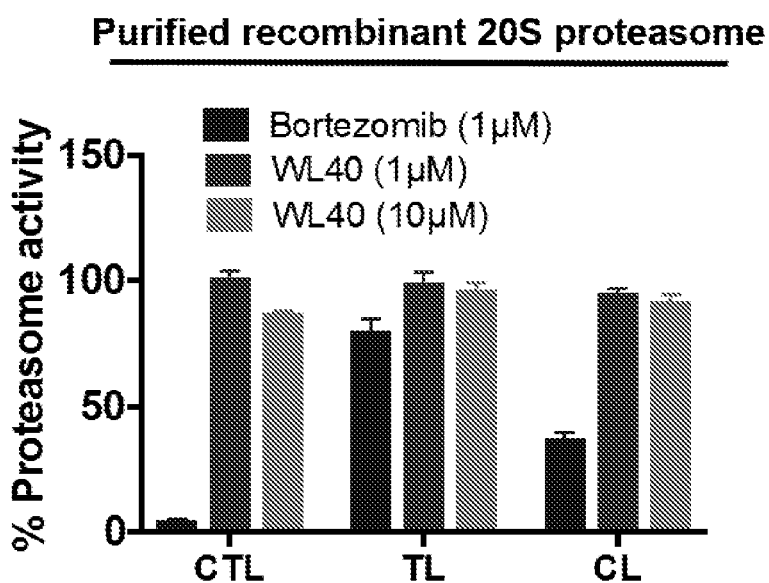
Figure 20C:
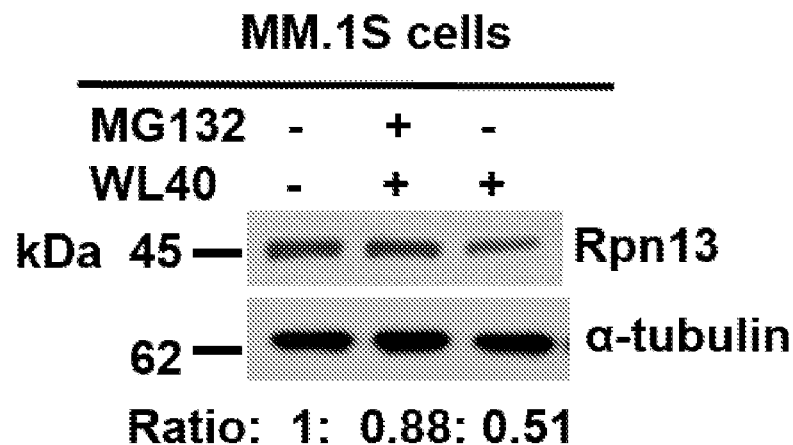
Figure 20D:
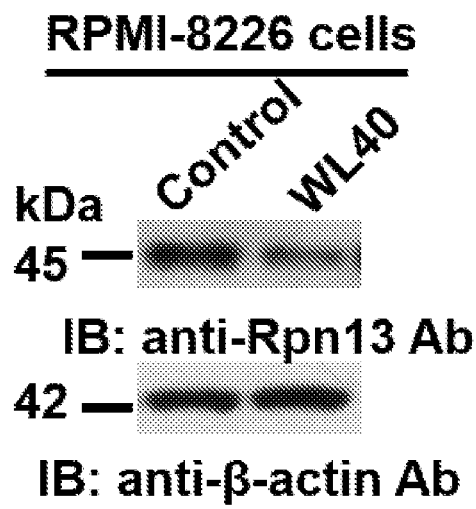
Figure 20E:
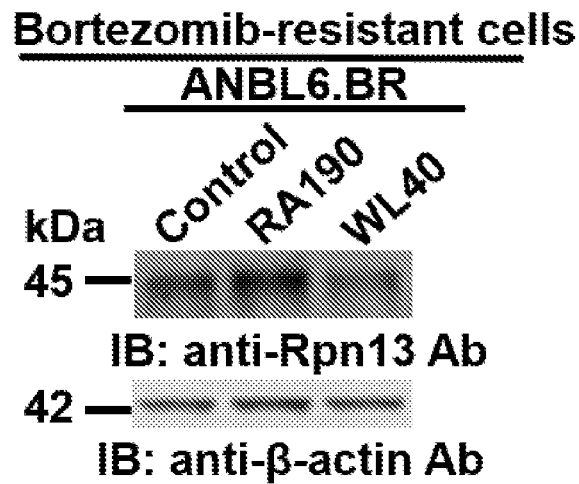
Figure 20F:
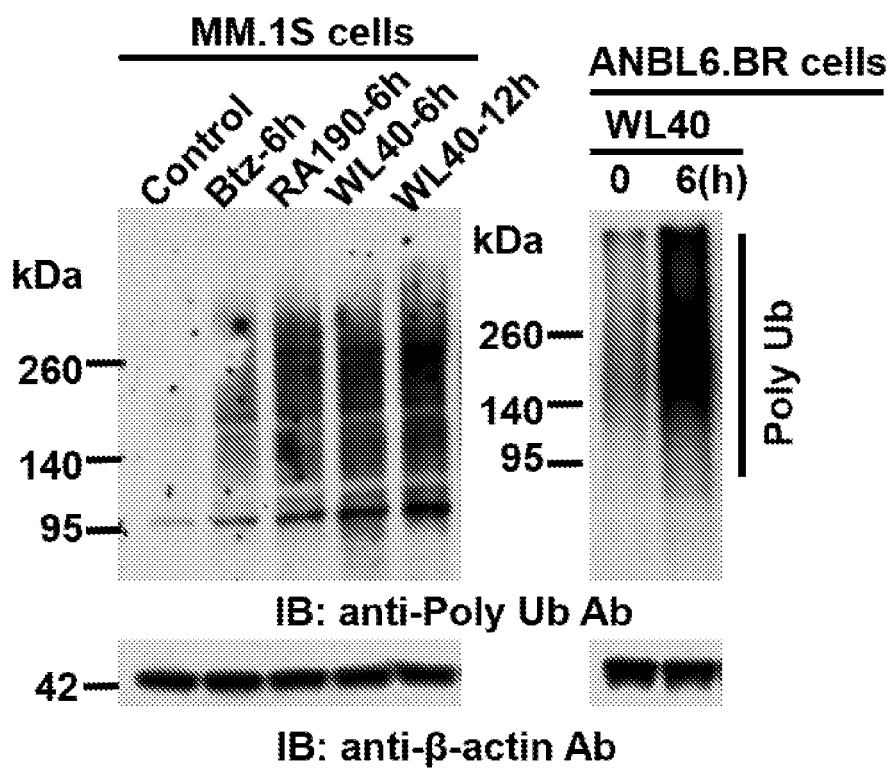

FIGS. 20A to 20F show that WL40 blocks proteasome-mediated protein degradation without inhibiting proteasome proteolytic activities FIG. 20A is a bar graph showing percent proteasome activity after normalization using DMSO control (mean±SD; n=3). MM.1S cells, which were treated with DMSO control, bortezomib, or WL40 at indicated concentration for 3 hours; protein lysates were analyzed for different proteasome activities (CT-L, chymotrypsin-like; T-L, trypsin-like; C-L, caspase-like). FIG. 20B is a bar graph showing percent proteasome activity after normalization with DMSO control (mean±SD; n=3). Recombinant 20S proteasome was incubated with DMSO, bortezomib, or WL40 for 30 minutes, followed by assessment of the above-noted proteasome activities. FIG. 20C MM.1S cells were pretreated with exemplary proteasome inhibitor MG132 (10 µM) for 1 hour, followed by addition of WL40 (400 nM) for 8 hours. As a positive control for WL40-induced Rpn13 degradation, cells were also treated with WL40 alone for 8 hours. Total protein lysates were subjected to immunoblots for Rpn13 and α-tubulin. FIG. 20D shows immunoblot analysis of RPMI-8226 cells, which were treated with WL40 (400 nM) for 16 hours; protein lysates were subjected to the immunoblot analysis using anti-Rpn13 or anti-β-actin Abs. FIG. 20E ANBL6.BR cells were treated with WL40 (400 nM) or RA190 (500 nM) for 16 hours; protein lysates were subjected to immunoblot analysis using anti-Rpn13 or anti-β-actin Abs. FIG. 20F shows immunoblot analysis of MM.1S cells, which were treated with DMSO control, bortezomib (5 nM), RA190 (300 nM), or WL40 (200 nM) for indicated time periods; protein lysates were subjected to the immunoblot analysis using anti-polyubiquitin or anti-β-actin Abs (left panel). FIG. 20F shows that ANBL6.BR cells were treated with DMSO as a control or WL40 (1 µM) for 6 hours; protein lysates were subjected to immunoblot analysis using anti-polyubiquitin or anti-β-actin Abs (right panel).

Figure 21A:
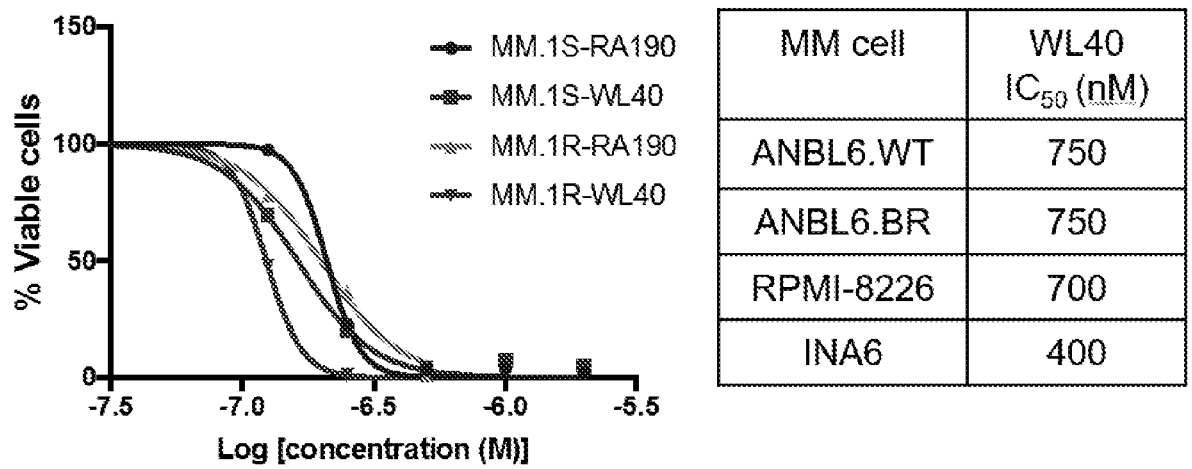
Figure 21B:
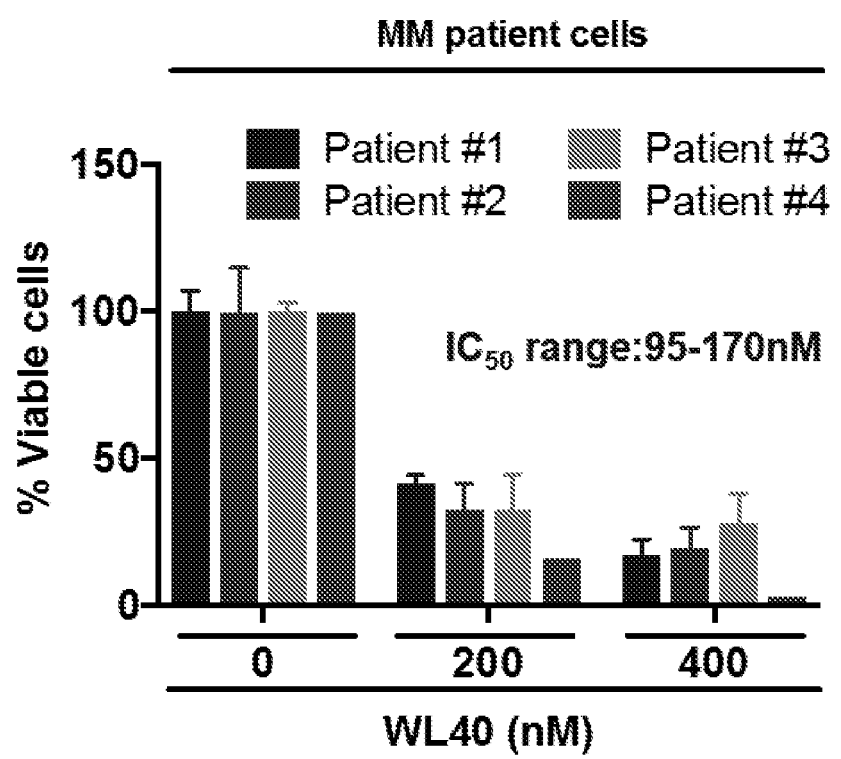
Figure 21C:
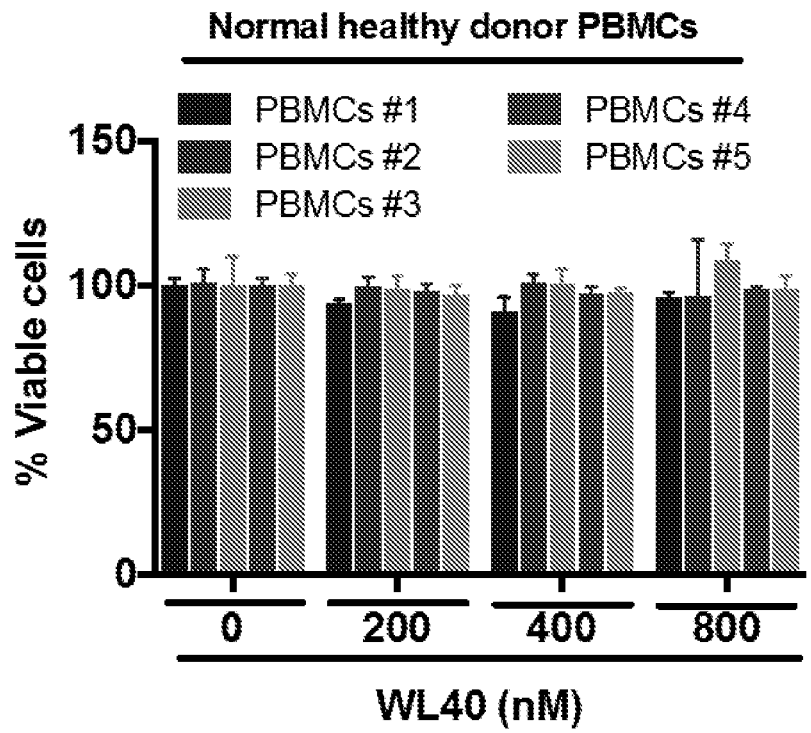
Figure 21D:
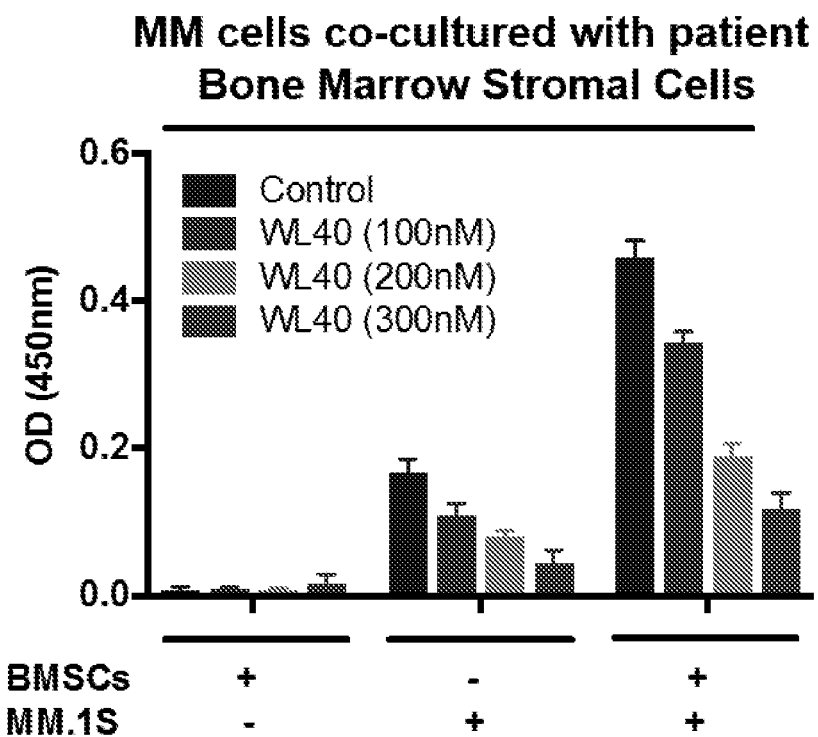
Figure 21E:
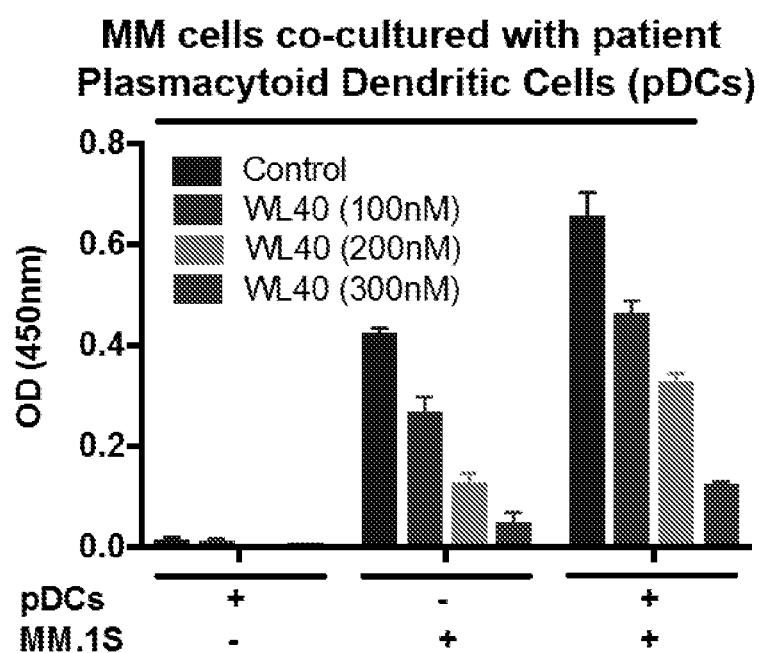

FIGS. 21A to 21E show that WL40 triggers anti-MM activity as well as overcomes the bortezomib-resistance and cytoprotective activity of the MM bone marrow (BM) microenvironment FIG. 21A shows an assessment for the cell viability of MM.1S and MM.1R cells, which were treated with DMSO control, WL40, or RA190 at indicated concentrations for 48 hours, followed by the assessment for cell viability using a standard WST (cell viability and proliferation) assay (p<0.05 for both cell lines; n=3). Table: ANBL6.WT (plasma cell myeloma; wild type), ANBL6.BR (plasma cell myeloma; bortezomib-resistant), RPMI-8226 (B-lymphocyte), or INA6 MM (plasma cell myeloma) cell lines were treated with DMSO as a control or WL40 for 48 hours, followed by assessment for cell viability. The IC$_{50}$ of WL40 for cell lines is shown. FIG. 21B is a bar graph showing the percentage of viable cells in different patients (patients 1-4). Purified CD138$^+$ patient MM cells, which were treated with DMSO control or WL40 at indicated concentrations for 48 hours, followed by assessment for cell viability using CellTiter-Glo assay (mean±SD of triplicate cultures; p<0.001). FIG. 21C is a bar graph showing the percentage of viable cells within the PBMCs. Normal PBMCs from healthy donors were treated with DMSO control or WL40 at indicated concentrations for 48 hours, and then analyzed for cell viability using CellTiter-Glo assay (mean±SD of quadruplicate cultures). FIG. 21D is a bar graph showing the percentage of viable cells within MM cells co-cultured with the patient BMSCs (bone marrow stromal cells). MM.1S cells were cultured with or without patient BMSCs in the presence or absence of WL40 for 48 hours, and cell proliferation was measured by WST assay (mean±SD; n=3; p<0.0001). FIG. 21E is a bar graph showing the percentage of viable cells within MM cells co-cultured with patient plasmacytoid dendritic cells (pDCs). MM.1S cells were cultured with or without patient pDCs in the presence or absence of WL40 for 48 hours, and cell proliferation was measured by WST assay (mean±SD; n=3; p<0.0001).

Figure 22A:
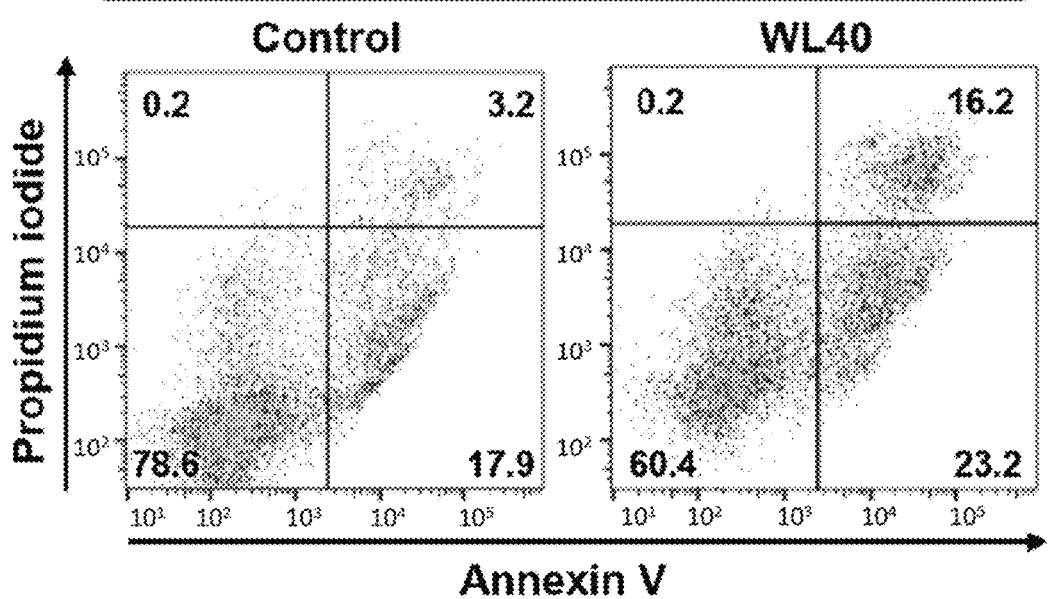
Figure 22B:
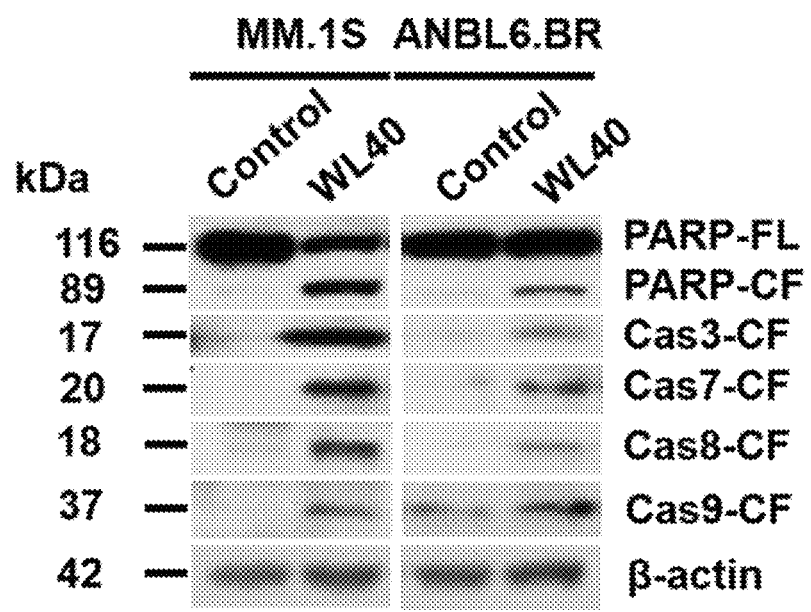
Figure 22C:
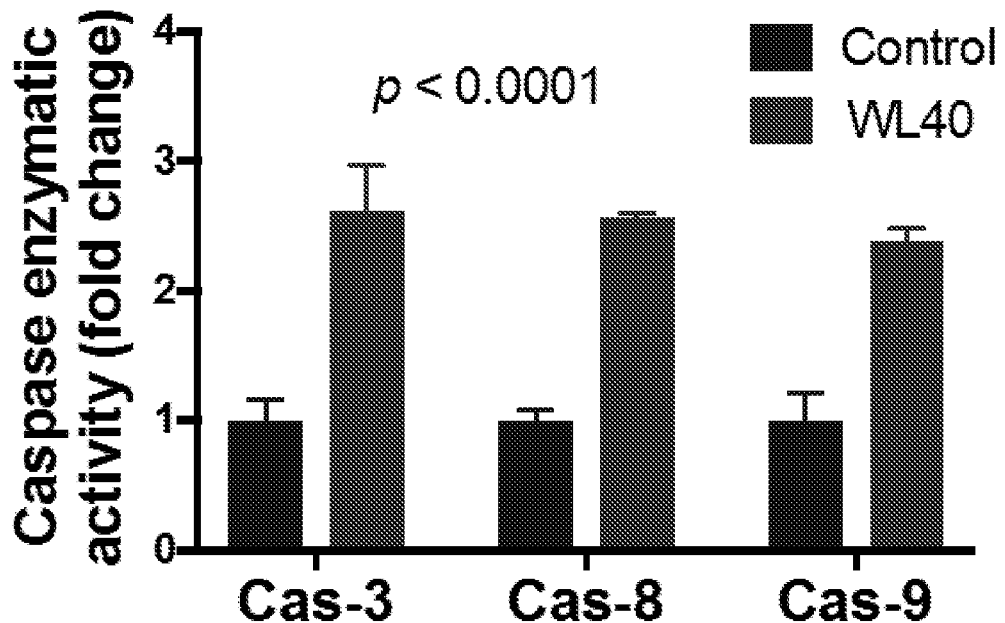
Figure 22D:
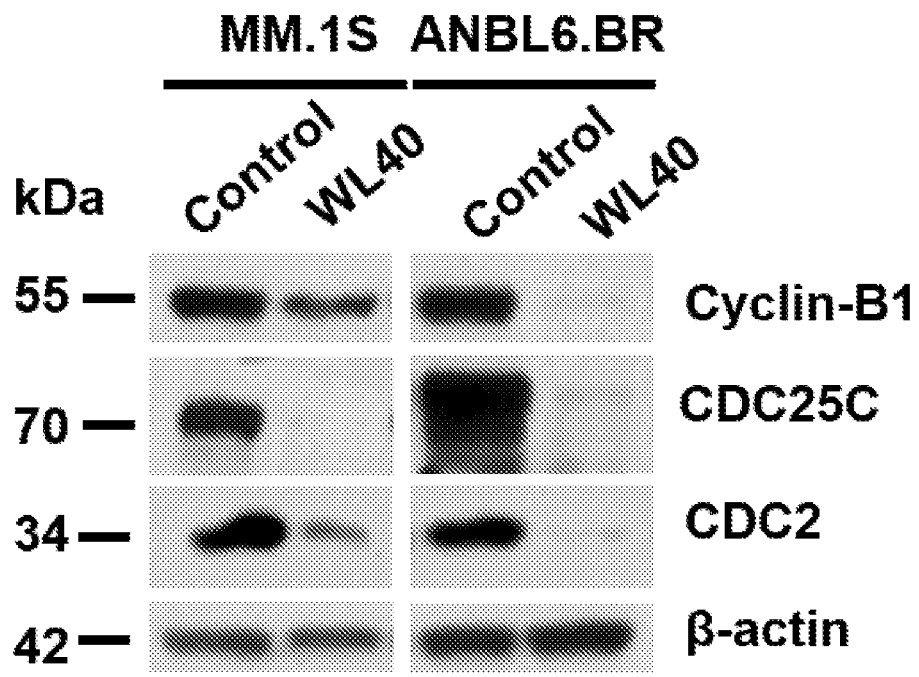
Figure 22E:
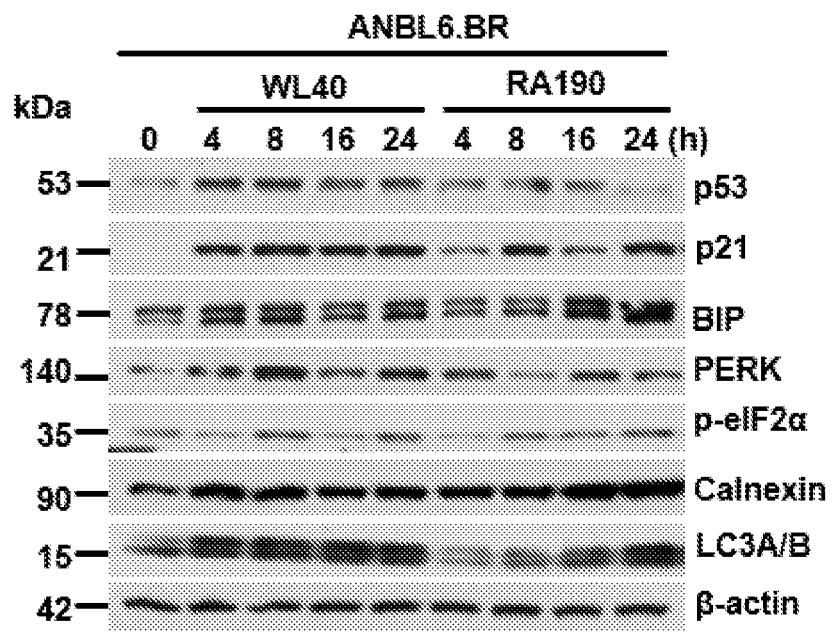
Figure 22F:
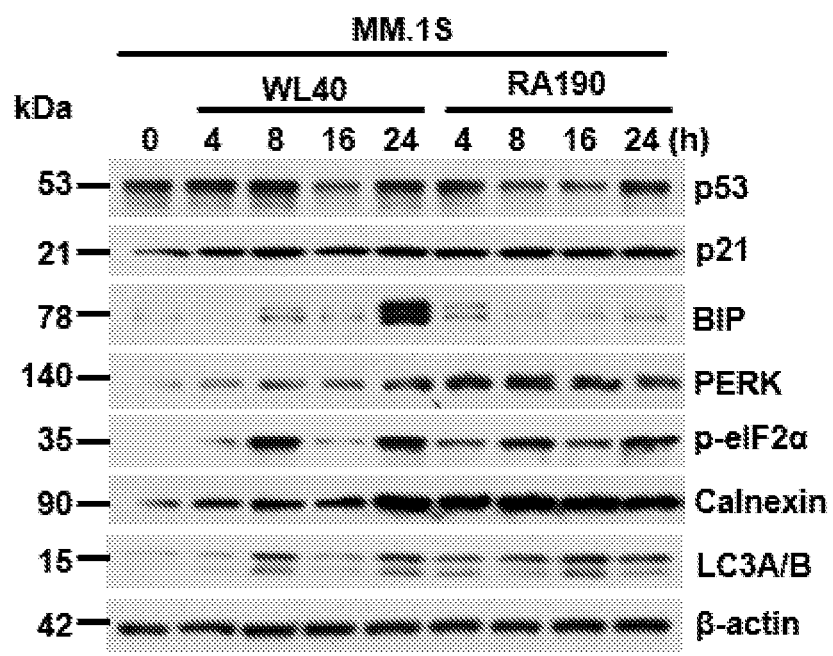

FIGS. 22A to 22F show the mechanisms of WL40-induced MM cell death. FIG. 22A shows an analysis of apoptosis in view of treatment of MM.1S cells with the control DMS or WL40. MM.1S cells were treated with DMSO control or WL40 (200 nM) for 16 hours, and then analyzed for apoptosis using Annexin V/PI double staining assay (mean±SD; n=3; p<0.001). FIG. 22B is an immunoblot of MM.1S and ANBL6.BR cells, which were treated with DMSO control or WL40 (200 nM for MM.1S; 1 μM for ANBL6.BR) for 16 hours; protein lysates were then subjected to the immunoblotting using antibodies against poly ADP ribose polymerase (PARP), caspase-3, caspase-7, caspase-8, caspase-9, or β-actin. FL, full length; CF, cleaved fragment. FIG. 22C is a bar graph measuring enzymatic activity. MM.1S cells were treated with DMSO control or WL40 (200 nM) for 12 hours, followed by the measurement of caspase-3, caspase-8, or caspase-9 enzymatic activity (mean±SD; n=3; p<0.0001). FIG. 22D is an immunoblot of MM.1S and ANBL6.BR cells, which were treated with DMSO control or WL40 (200 nM for MM.1S; 1 μM for ANBL6.BR) for 16 hours; protein lysates were then subjected to the immunoblotting using specific antibodies against Cyclin-B1, Cell Division Cycle 25C (CDC25C), Cell Division Cycle 2 (CDCl$_2$), or β-actin. FIG. 22E is an immunoblot of ANBL6.BR cells, which were treated with DMSO as a control, WL40 (1 μM), or RA190 (1 μM) for the indicated time periods; protein lysates were subjected to the immunoblotting using specific antibodies against p53, p21, BIP, PERK, p-eIF2α, calnexin, LC3A/B, and β-actin. FIG. 22F is an immunoblot of MM.1S cells, which were treated with DMSO as a control, WL40 (200 nM), or RA190 (300 nM) for the indicated time periods; protein lysates were subjected to the immunoblotting using specific antibodies against p53, p21, BIP, PERK, p-eIF2a, calnexin, LC3A/B, and β-actin. Blots shown are representative of three independent experiments.

Figure 23A:
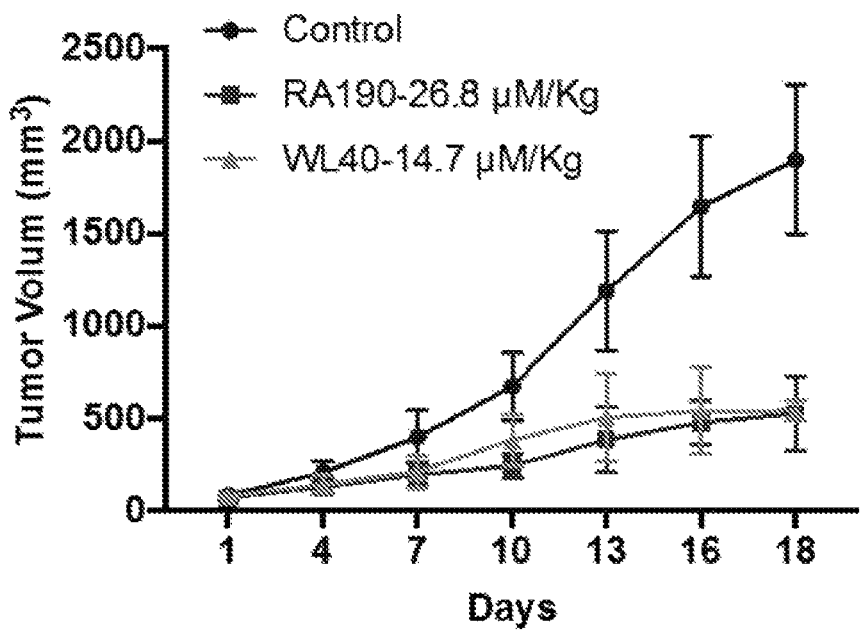
Figure 23B:
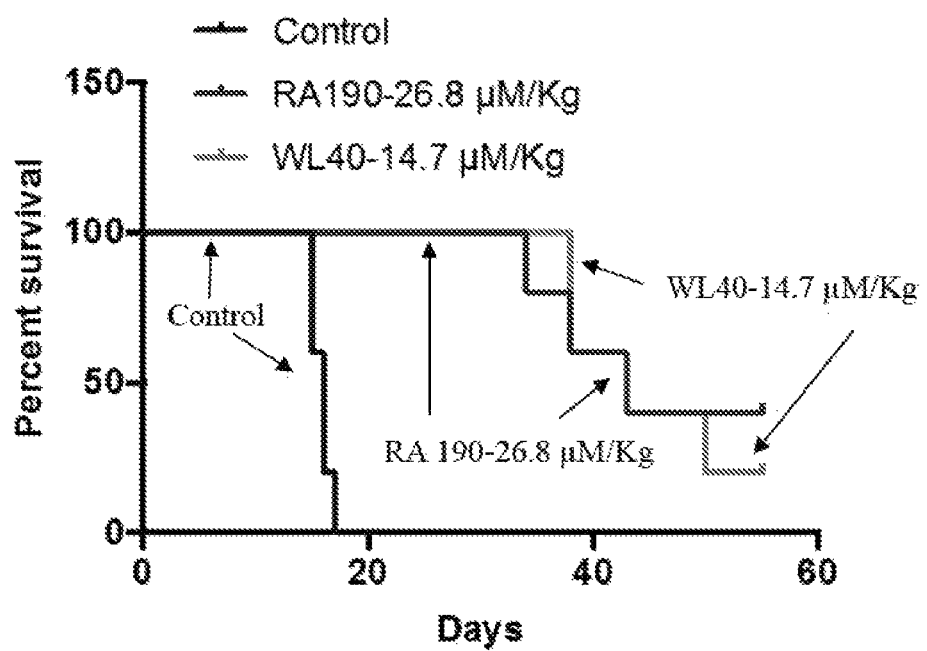
Figure 23C:
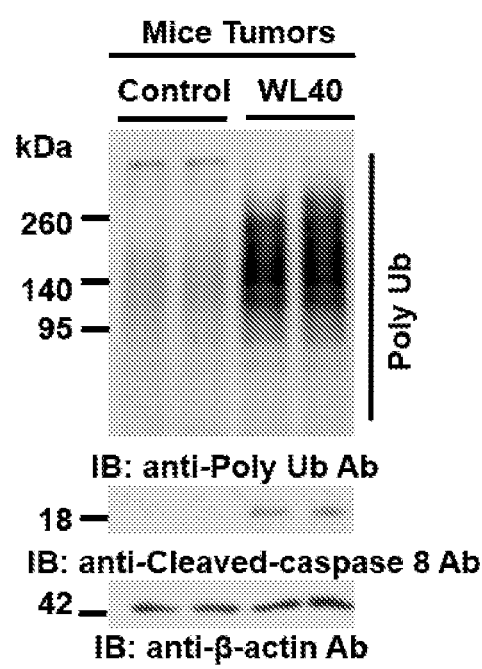
Figure 23D:
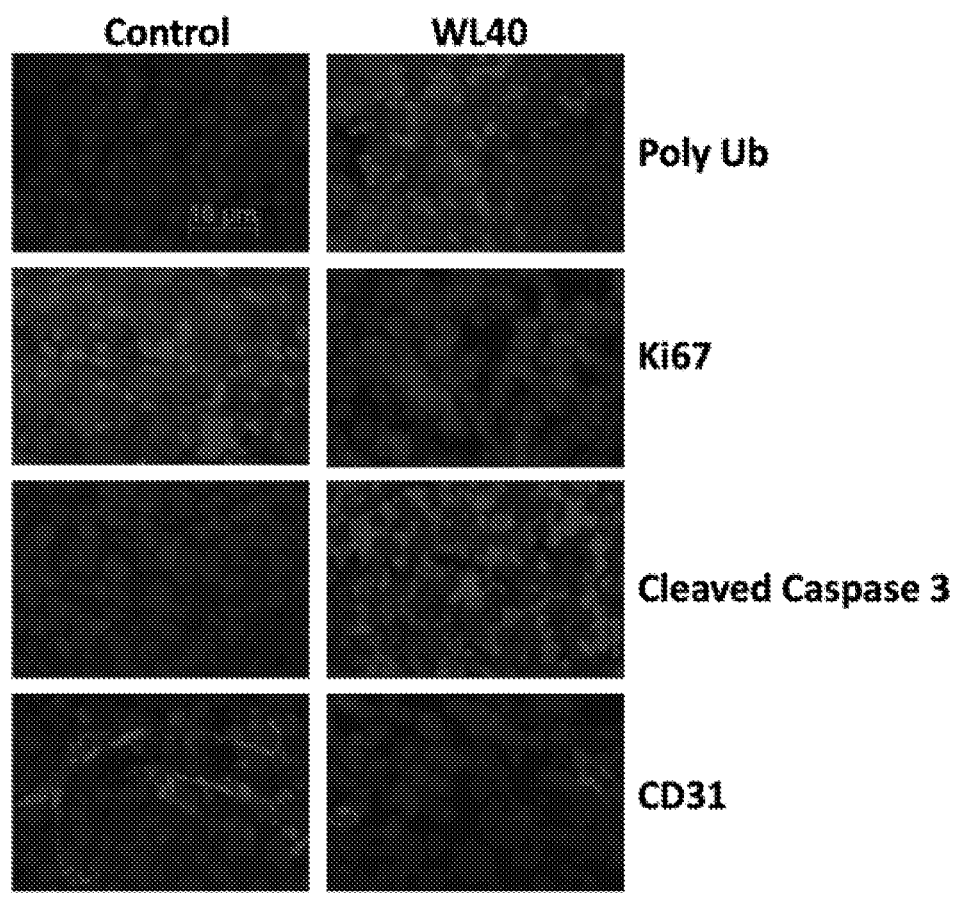

FIGS. 23A to 23D show that WL40 inhibits xenografted human MM cell growth and prolongs host survival FIG. 23A shows the tumor volume (mean tumor volume±SD in mm$^3$, 10 mice/group) upon treatment with WL40 and RA190 at the indicated concentration versus time. Mice bearing human MM.1S MM tumors were treated with either vehicle control, WL40 (14.7 μM/kg; i.p.), or RA190 (26.8 μM/kg; i.p.) twice weekly for 18 days. FIG. 23B are Kaplan-Meier plots which show survival of mice. FIG. 23C shows immunoblot analysis of lysates of tumors harvested from control mice, and WL40- and RA190-treated mice. The lysates were subjected to the immunoblot analysis using anti-polyubiquitin, anti-cleaved-caspase-8, or anti-β-actin Abs. FIG. 23D show tumor sections from the vehicle control, and WL40-treated mice that were stained with anti-polyubiquitin, Ki67, caspase-3 (cleaved form), and CD31 antibodies. Scale bar, 10 μm.

Figure 24A:
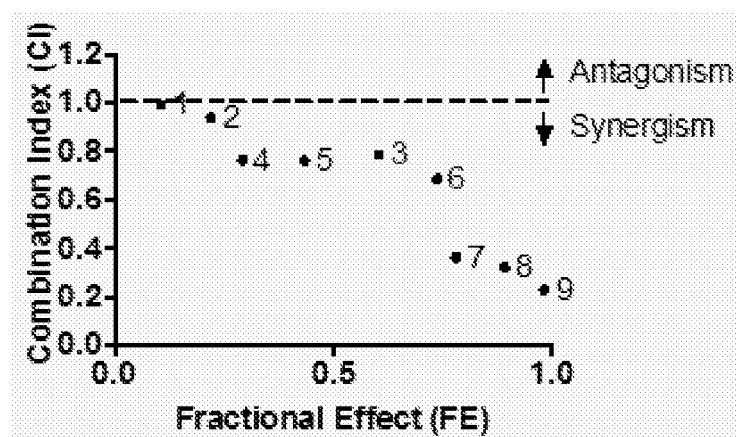
Figure 24B:
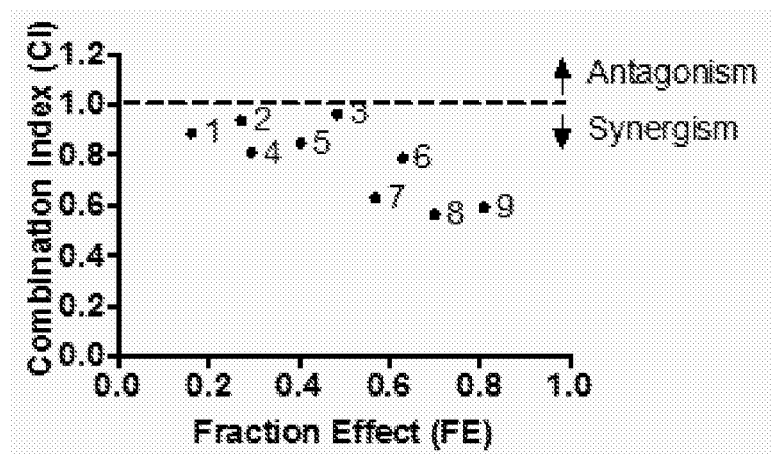
Figure 24C:
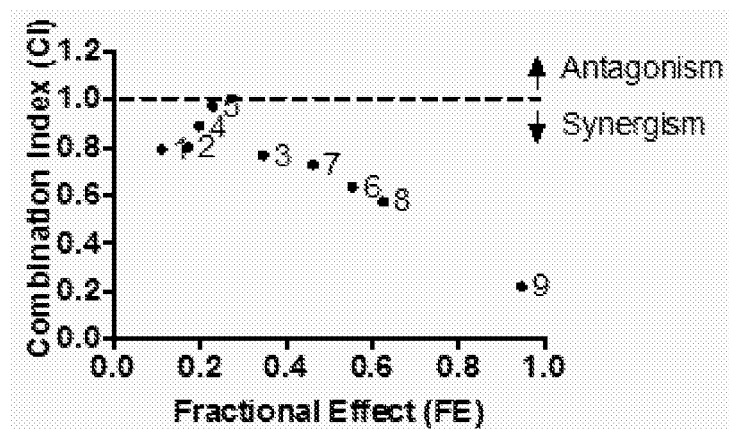

FIGS. 24A to 24C show that combinations of WL40 with pomalidomide, lenalidomide, or bortezomib trigger synergistic anti-MM activity. FIG. 24A shows MM.1S cells that were treated with WL40, pomalidomide, or WL40 plus pomalidomide for 48 hours, and then assessed for viability using WST assay. Isobologram analysis shows the synergistic cytotoxic effect of WL40 and pomalidomide. The graph is derived from the values given in the table (lower panel). Combination index (CI)<1 indicates synergy. FIG. 24B shows MM.1S cells that were treated with WL40, lenalidomide, or WL40 plus lenalidomide for 48 hours, and then assessed for viability using WST assay. Synergistic anti-MM activity was analyzed as in FIG. 24A. FIG. 24C shows MM.1S cells that were treated with WL40, bortezomib, or WL40 plus bortezomib for 48 hours, and then assessed for viability using a WST assay. Synergistic anti-MM activity was analyzed as in FIG. 24A.

Figure 25A:
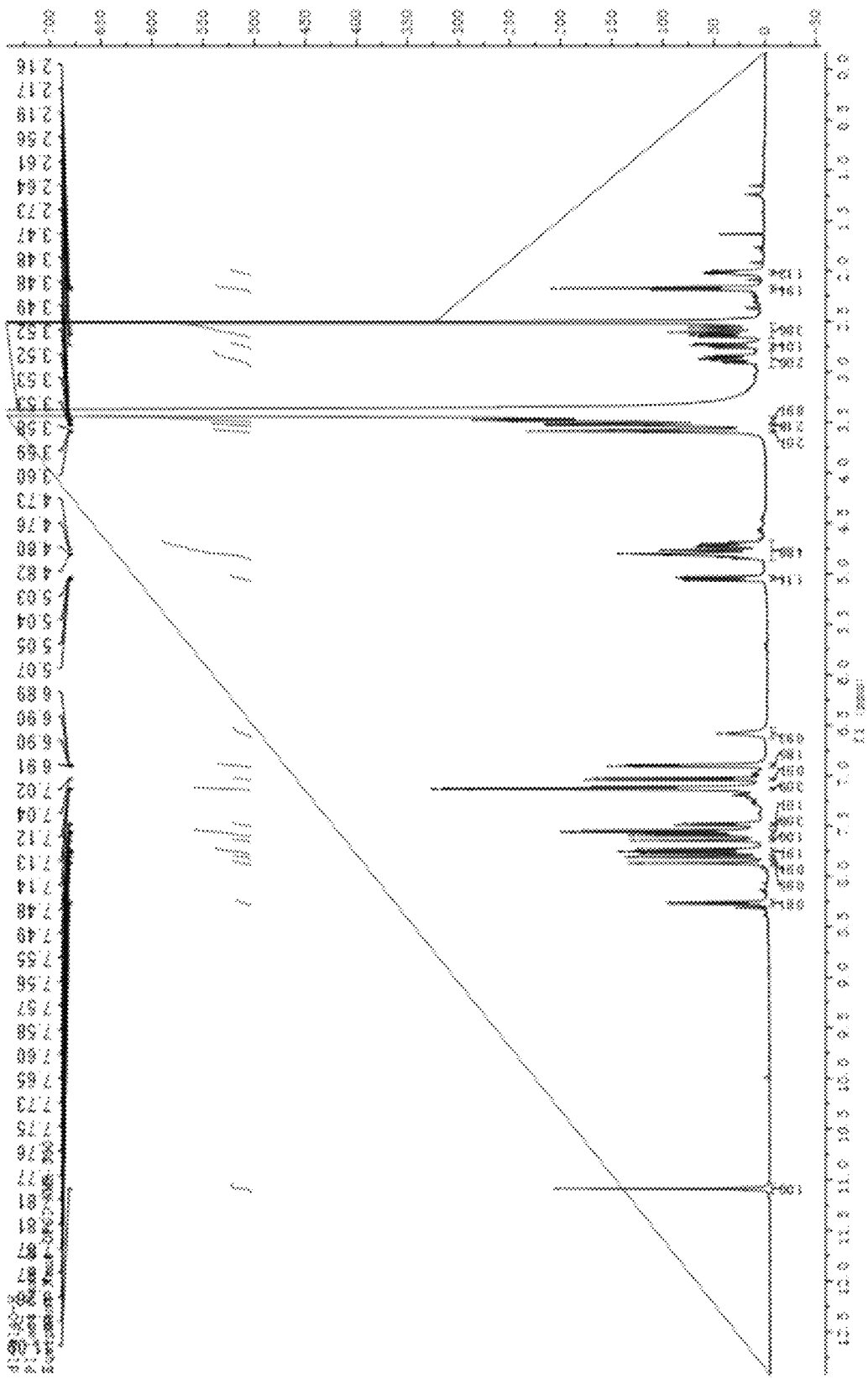
Figure 25B:
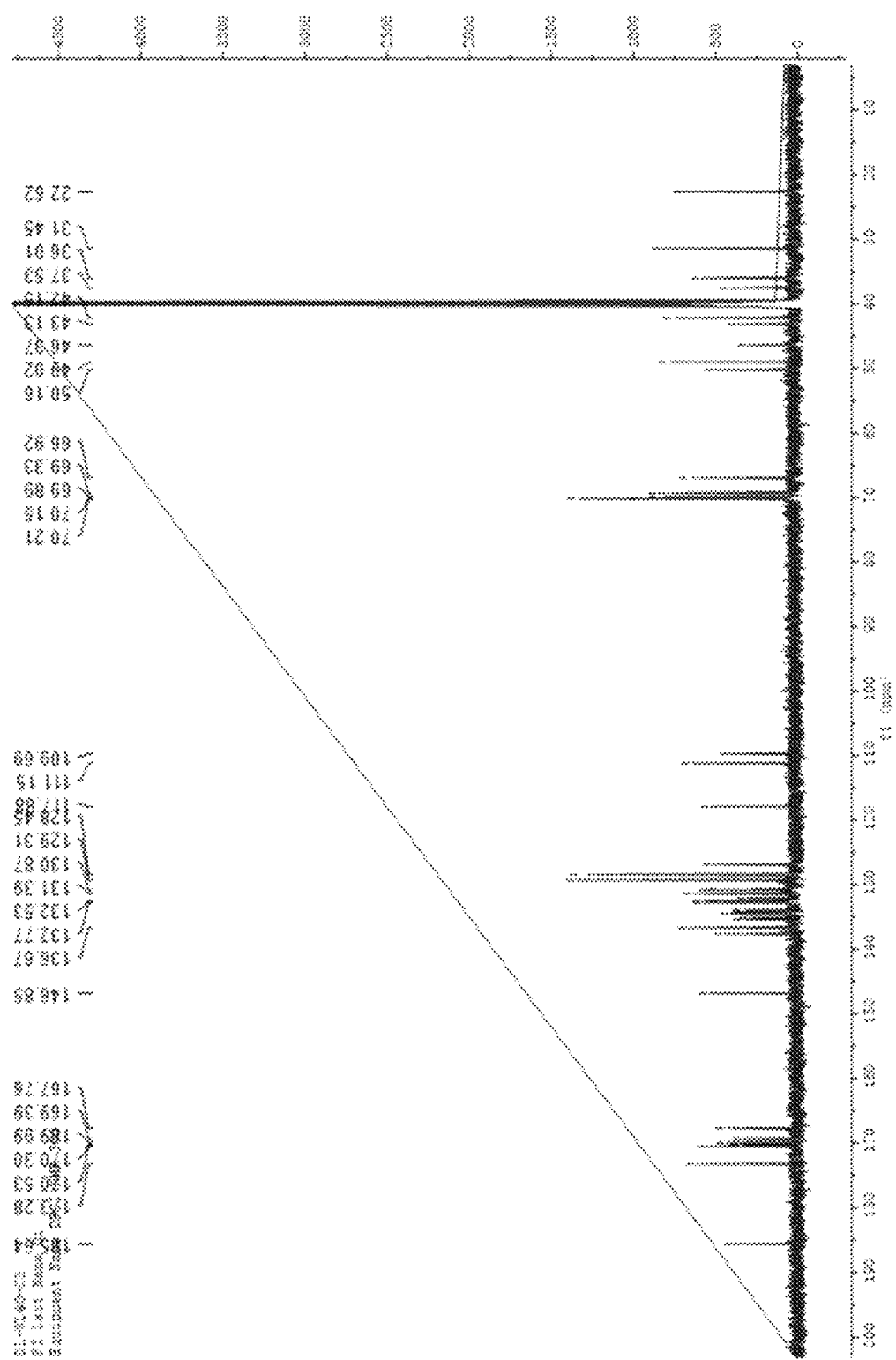

FIGS. 25A to 25B show NMR spectra for WL40. The compound WL40 was fully characterized using $^1$H NMR (FIG. 25A) and $^{13}$C NMR (FIG. 25B).

DETAILED DESCRIPTION OF CERTAIN EMBODIMENTS OF THE INVENTION

The bifunctional compounds described herein interact with an E3 ubiquitin ligase and the ubiquitin receptor RPN13 (ADRM1). As described herein, without wishing to be bound by any particular theory, the therapeutic effect may be the result of degradation, modulation, or binding of an E3 ubiquitin ligase (e.g., Cereblon) by a compound described herein. For example, the therapeutic effect may be a result of recruitment of an E3 ubiquitin ligase (e.g., Cereblon) by modulation, targeting, binding, or modification of the E3 ubiquitin ligase, which induces the ubiquitination of a target protein, such as RPN13, and the use of a binder of the ubiquitin receptor RPN13 (e.g., RA190) which brings the E3 ubiquitin ligase in proximity to RPN13. E3 ubiquitin ligase is brought into proximity with RPN13, which leads to the ubiquitination of RPN13 and its subsequent degradation by the proteasome.

A compound may be provided for use in any composition, kit, or method described herein as a pharmaceutically acceptable salt, co-crystal, tautomer, stereoisomer, solvate, hydrate, polymorph, isotopically enriched derivative, or prodrug thereof.

In certain embodiments, the compounds that bind to RPN13 are compounds derived from the compounds described in U.S. patent application U.S. Ser. No. 14/889,768, filed May 6, 2014, which is incorporated herein by reference.

In certain embodiments, the E3 ubiquitin ligase binding moiety of the bifunctional compounds of Formulae (I) and (I') is derived from E3 ubiquitin ligase binding moiety (based on an immunomodulatory imide drug (e.g., derivatives of lenalidomide, thalidomide) of the bifunctional compounds described in U.S. patent application U.S. Ser. No. 15/148,253, filed May 6, 2016, U.S. Ser. No. 14/707,930, filed May 8, 2015, U.S. Ser. No. 62/096,318, filed Dec. 23, 2014, U.S. Ser. No. 62/128,457, filed Mar. 4, 2015, U.S. Ser. No. 62/149,170, filed Apr. 17, 2015, each of which is incorporated herein by reference.

In certain embodiments, the E3 ubiquitin ligase binding moiety of the bifunctional compounds of Formula (I) is derived from E3 ubiquitin ligase binding moiety within the bifunctional compounds described in U.S. patent application U.S. Ser. No. 15/148,253, filed May 6, 2016, U.S. Ser. No. 14/707,930, filed May 8, 2015, U.S. Ser. No. 62/096,318, filed Dec. 23, 2014, U.S. Ser. No. 62/128,457, filed Mar. 4, 2015, U.S. Ser. No. 62/149,170, filed Apr. 17, 2015, each of which is incorporated herein by reference.

In one aspect, disclosed are compounds of Formulae (I) and (I'):

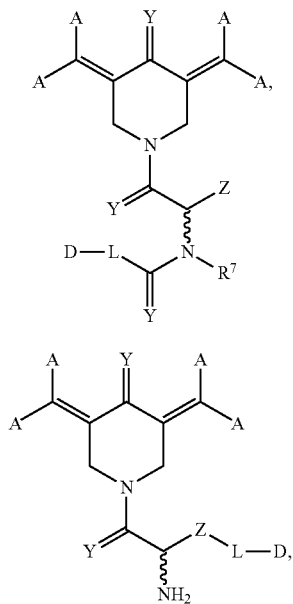

or a pharmaceutically acceptable salt, solvate, hydrate, tautomer, or stereoisomer thereof, wherein:

in each pair of A's, one A is hydrogen, and the other A is one of:

(i) phenyl, optionally substituted with 1-5 substituents selected from the group consisting of $R^1$, $OR^1$, $NR^1R^2$, $S(O)_qR^1$, $SO_2R^1R^2$, $NR^1R^2SO_2R_2$, $C(O)R^1$, $C(O)OR^1$, $C(O)NR^1R^2$, $NR^1C(O)R^2$, $NR^1C(O)OR^2$, $CF_3$, and $OCF_3$;

(ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

(iii) a 5- or 6-membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and (iv) an 8- to 10-membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

wherein Y is selected from the group consisting of O, S, $NR^1$, and $CR^1R^2$, and wherein $R^1$ and $R^2$ are selected from the group consisting of hydrogen, nitro, hydroxyl, carboxy, amino, halogen, cyano and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano;

wherein $R^7$ is hydrogen, $C_{1-6}$ alkyl, or a nitrogen protecting group;

wherein Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; —$(CH_2)_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4;

L is a linker; and

D is an E3 ubiquitin ligase binding moiety.

Group D

In certain embodiments, D is an E3 ubiquitin ligase binding moiety. D is inclusive of all moieties that bind, or can bind, any E3 ubiquitin ligase. For example, in certain embodiments, D is capable of binding an E3 ubiquitin ligase, such as Cereblon. In certain embodiments, D is capable of binding to multiple different E3 ubiquitin ligases. In certain embodiments, E binds to Cereblon. In certain embodiments, D is based on an immunomodulatory imide drug. In certain embodiments, D is derived from lenalidomide. In certain embodiments, D is derived from thalidomide.

Human Cereblon (CRBN) is a protein of 442 amino acids with an apparent molecular weight of ~51 kDa (GenBank: AAH17419). (For the CRBN protein sequence see: Higgins et al., *Neurology.* 2004, 63, 1927-31. For additional information related to the CRBN structure see Hartmann et al., *PLoS One.* 2015, 10, e0128342.) Human CRBN contains the N-terminal part (237-amino acids from 81 to 317) of ATP-dependent Lon protease domain without the conserved Walker A and Walker B motifs, 11 casein kinase II phosphorylation sites, 4 protein kinase C phosphorylation sites, 1 N-linked glycosylation site, and 2 myristoylation sites. CRBN is widely expressed in testis, spleen, prostate, liver, pancreas, placenta, kidney, lung, skeletal muscle, ovary, small intestine, peripheral blood leukocyte, colon, brain, and retina. CRBN is located in the cytoplasm, nucleus, and peripheral membrane. (Chang et al., *Int. J. Biochem. Mol. Biol.* 2011, 2, 287-94.)

Cereblon is an E3 ubiquitin ligase, and it forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, Cereblon ubiquitination of target proteins results in increased levels of fibroblast growth factor 8 (FGF8) and fibroblast growth factor 10 (FGF10). FGF8, in turn, regulates a number of developmental processes, such as limb and auditory vesicle formation.

In certain embodiments, D is a modulator, binder, inhibitor, or ligand of Cereblon. In certain embodiments, D is a modulator of Cereblon. In certain embodiments, D is a binder of Cereblon. In certain embodiments, D is an inhibitor of Cereblon. In certain embodiments, D is a ligand of Cereblon. In certain embodiments, D is any modulator, binder, inhibitor, or ligand of Cereblon disclosed in U.S. patent application U.S. Ser. No. 14/792,414, filed Jul. 6, 2015, U.S. patent application U.S. Ser. No. 14/707,930, filed May 8, 2015, and International Patent Application, PCT/US2013/054663, filed Aug. 13, 2013, each of which is incorporated herein by reference. In certain embodiments, D is a modulator, binder, inhibitor, or ligand of a Cereblon variant. In certain embodiments, D is a modulator, binder, inhibitor, or ligand of a Cereblon isoform.

In certain embodiments, D comprises a heteroaryl ring. In certain embodiments, D comprises a fused bicyclic heteroaryl ring. In certain embodiments, D comprises a fused bicyclic heteroaryl ring and a heterocyclic ring. In certain embodiments, D comprises a fused bicyclic heteroaryl ring and a heterocyclic ring, where the heterocyclic ring contains at least one nitrogen. In certain embodiments, D comprises a fused bicyclic heteroaryl ring and a heterocyclic ring, where the fused bicyclic heteroaryl ring and heterocyclic ring each contain at least one nitrogen. In certain embodiments, D comprises a fused bicyclic heteroaryl ring and a heterocyclic ring, where the fused bicyclic heteroaryl ring and heterocyclic ring each contain one nitrogen. In certain embodiments, D comprises a phthalimido group, or an analogue or derivative thereof. In certain embodiments, D comprises a phthalimido-glutarimide group, or an analogue or derivative thereof.

In certain embodiments, D is of Formula (E-I):

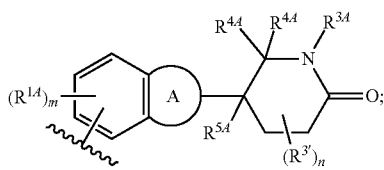

(E-I)

wherein:

Ring A is a substituted or unsubstituted heterocyclyl, or substituted or unsubstituted heteroaryl ring;

each $R^{1A}$ is, independently, halogen, —OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl;

m is 0, 1, 2, or 3; and n is 1 or 2.

In certain embodiments, Formula (E-I) is derived from an immunomodulatory imide drug (e.g., derived from lenalidomide or thalidomide). In certain embodiments, Formula (E-I) is of Formula (IA) or Formula (IB).

In certain embodiments, D is of Formula (IA):

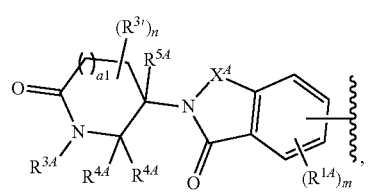

(IA)

wherein:

$X^A$ is C(O) or $C(R^{3A})_2$;

each $R^{1A}$ is independently halogen, OH, $C_1$-$C_6$ alkyl, or $C_1$-$C_6$ alkoxy;

$R^{3A}$ is H or $C_1$-$C_3$ alkyl;

each $R^{3'}$ is independently $C_1$-$C_3$ alkyl;

each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, or halogen;

m is 0, 1, 2, or 3;

n is (3, 1 or 2; and a1 is 0 or 1.

In certain embodiments, D is of Formula (IA-a):

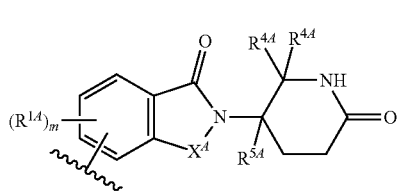

(IA-a)

wherein:

$X^A$ is C(O) or $C(R^{3A})_2$;

each $R^{1A}$ is, independently, halogen, OH, $C_1$-$C_6$ alkyl, or $C_1$-$C_6$ alkoxy;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl; and m is 0, 1, 2, or 3.

In certain embodiments, D is of Formula (IA-b):

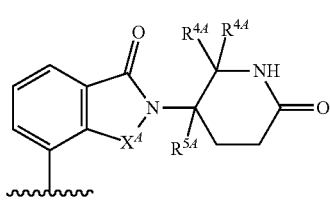

(IA-b)

wherein:

$X^A$ is C(O) or $C(R^{3A})_2$;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and
$R^{5A}$ is H, $C_1$-$C_3$ alkyl, F, or Cl.

In certain embodiments, D is of Formula (IA-c):

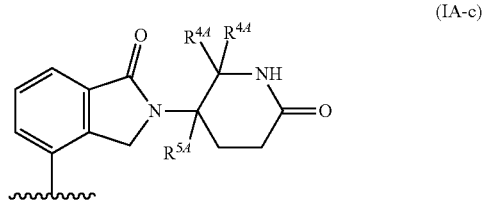

(IA-c)

wherein:
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and
$R^{5A}$ is H, $C_1$-$C_3$ alkyl, F, or Cl.

In certain embodiments, D is of Formula (IA-d):

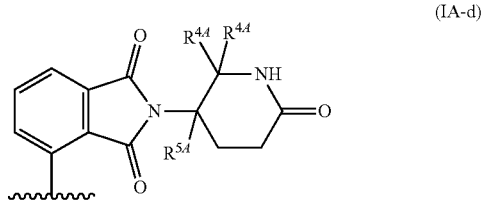

(IA-d)

wherein:
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and
$R^{5A}$ is H, $C_1$-$C_3$ alkyl, F, or Cl.

In certain embodiments, D is of Formula (IB):

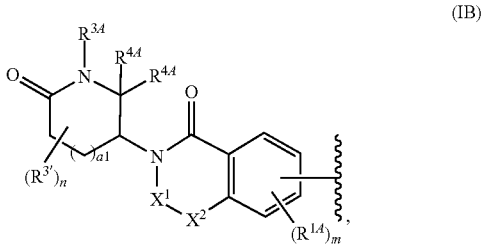

(IB)

wherein:
—$X^1$—$X^2$— is C($R^{3A}$)=N or C($R_{3A}$)$_2$—C($R^{3A}$)$_2$;
each $R^{1A}$ is independently halogen, OH, $C_1$-$C_6$ alkyl, or $C_1$-$C_6$ alkoxy;
$R^{3A}$ is H or $C_1$-$C_3$ alkyl;
each $R^{3'}$ is independently $C_1$-$C_3$ alkyl;
each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, or halogen;
m is 0, 1, 2, or 3;
n is 0, 1, or 2; and
a1 is 0 or 1.

In certain embodiments, D is of Formula (IB-a):

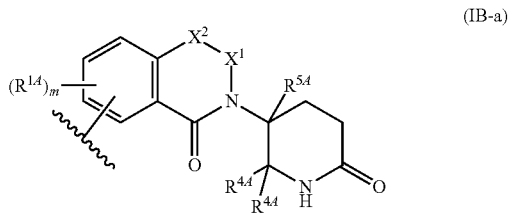

(IB-a)

wherein:
$X^1$—$X^2$ is C($R^{3A}$)=N or C($R^{3A}$)$_2$—C($R^{3A}$)$_2$;
each $R^{1A}$ is, independently, halogen, —OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl; and
m is 0, 1, 2, or 3.

In certain embodiments, D is of Formula (IB-b):

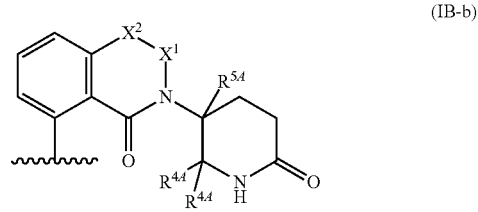

(IB-b)

wherein:
$X^3$—$X^2$ is C($R^{3A}$)=N or C($R^{3A}$)$_2$—C($R^{3A}$)$_2$;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl.

In certain embodiments, D is of Formula (IB-c):

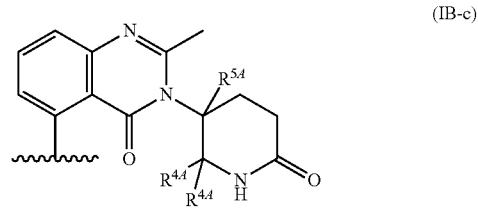

(IB-c)

wherein:
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl.

Formulae (IA), (IA-a), and (IA-b) include substituent $X^A$. In certain embodiments, $X^A$ is C(O). In certain embodiments, $X^A$ is $C(R^{3A})_2$.

Formulae (IA), (IA-a), and (IA-b) include substituents —$X^1$—$X^2$—. In certain embodiments, —$X^1$—$X^2$— is $C(R^{3A})$=N. In certain embodiments, —$X^1$—$X^2$— is C(H)=N. In certain embodiments, —$X^1$—$X^2$— is C($C_1$-$C_3$ alkyl)=N. In certain embodiments, —$X^1$—$X^2$— is $C(R_{3A})_2$—$C(R^{3A})_2$. In certain embodiments, —$X^1$—$X^2$— is $C(H)_2$—$C(H)_2$. In certain embodiments, —$X^1$—$X^2$— is $C(H)_2$—$C(C_1$-$C_3$ alkyl)$_2$. In certain embodiments, —$X^1$—$X^2$— is $C(H)_2$—C($C_1$-$C_3$ alkyl)$_2$. In certain embodiments, —$X^1$—$X^2$— is $C(H)_2$—$C(C_1$-$C_3$ alkyl)$_2$. In certain embodiments, —$X^1$—$X^2$— is $C(C_1$-$C_3$ alkyl)$_2$-$C(C_1$-$C_3$ alkyl)$_2$.

Formula (E-I) includes Ring A. In certain embodiments, Ring A is a substituted or unsubstituted heterocyclyl ring. In certain embodiments, Ring A is a substituted or unsubstituted heterocyclyl ring, which is a 3- to 10-membered non-aromatic ring system having ring carbon atoms and 1 to 4 ring heteroatoms, wherein each heteroatom is independently selected from nitrogen, oxygen, or sulfur. In certain embodiments, Ring A is a substituted or unsubstituted heteroaryl ring. In certain embodiments, Ring A is a substituted or unsubstituted heterocyclyl ring, which is a 5-10 membered monocyclic or bicyclic 4n+2 aromatic ring system having ring carbon atoms and 1-4 ring heteroatoms provided in the aromatic ring system, wherein each heteroatom is independently selected from the group consisting of nitrogen, oxygen and sulfur. In certain embodiments, Ring A is a substituted or unsubstituted pyrrolidin-2-one. In certain embodiments, Ring A is a substituted or unsubstituted pyrrolidine-2,5-dione. In certain embodiments, Ring A is a substituted or unsubstituted 5,6-dihydropyrimidin-4(3H)-one. In certain embodiments, Ring A is a substituted or unsubstituted tetrahydropyrimidin-4(1H)-one.

Formulae (E-I), (IA-a), (IA), (IB), and (IB-a) include substituent $R^{1A}$. In certain embodiments, $R^{1A}$ is independently halogen, OH, $C_1$-$C_6$ alkyl, or $C_1$-$C_6$ alkoxy. In certain embodiments, at least one instance of $R^{1A}$ is halogen (e.g., F, Cl, Br, or I). In certain embodiments, at least one instance of $R^{1A}$ is OH. In certain embodiments, at least one instance of $R^{1A}$ is $C_1$-$C_6$ alkyl (e.g., methyl, ethyl). In certain embodiments, at least one instance of $R^{1A}$ is $C_1$-$C_6$ alkoxy (e.g., methoxy, ethoxy). In certain embodiments, m is 0. In certain embodiments, m is 1. In certain embodiments, m is 2. In certain embodiments, m is 3.

Formulae (E-I), (IA), (IB), (IB-a), and (IB-b) include substituent $R^{3A}$. In certain embodiments, at least one instance of $R^{3A}$ is H. In certain embodiments, at least one instance of $R^{3A}$ is $C_1$-$C_3$ alkyl (e.g., methyl, ethyl). In certain embodiments, at least one instance of $R^3$ is $C_1$-$C_3$ alkyl (e.g., methyl, ethyl). In certain embodiments, n is 0. In certain embodiments, n is 1. In certain embodiments, n is 2.

Formulae (E-I), (IA-a), (IA-b), (IA-c), (IA-d), (IA), (IB), (IB-a), (IB-b), and (IB-c) include substituent $R^{5A}$. In certain embodiments, $R^{5A}$ is H. In certain embodiments, $R^{5A}$ is deuterium. In certain embodiments, $R^{5A}$ is $C_1$-$C_3$ alkyl. In certain embodiments, $R^{3A}$ is halogen (e.g., F, Cl, Br, or I).

In certain embodiments, a1 is 0. In certain embodiments, a1 is 1.

Formulae (E-I), (IA-a), (IA-b), (IA-c), (IA-d), (IA), (IB), (IB-a), (IB-b), and (IB-c) include substituent $R^{4A}$. In certain embodiments, at least one instance of $R^{4A}$ is H. In certain embodiments, at least one instance of $R^{4A}$ is $C_1$-$C_3$ alkyl (e.g., methyl, ethyl). In certain embodiments, two $R^{4A}$, together with the carbon atom to which they are attached, form a C(O), $C_3$-$C_6$ carbocycle, or a. 4-, 5-, or 6-membered heterocycle comprising 1 or 2 heteroatoms selected from N and O.

In certain embodiments, m and n are both 0; $R^{3A}$ is H; two $R^{4A}$, together with the carbon atom to which they are attached, form a C(O); and $R^{5A}$ is H.

In certain embodiments, a1 is 1; m and n are both 0; $R^{3A}$ is H; two $R^{4A}$, together with the carbon atom to which they are attached, form a C(O); $R^{5A}$ is H; and $X^A$ is C(O). In certain embodiments, a1 is 1; m and n are both 0; $R^{3A}$ is H; two $R^{4A}$, together with the carbon atom to which they are attached, form a C(O); $R^{5A}$ is H; and $X^A$ is $C(R^{3A})_2$. In certain embodiments, two $R^{4A}$, together with the carbon atom to which they are attached, form a C(O); $R^{5A}$ is H; and $X^A$ is C(O). In certain embodiments, two $R^{4A}$, together with the carbon atom to which they are attached, form a C(O); $R^{5A}$ is H; and $X^A$ is $C(R^{3A})_2$. In certain embodiments, two $R^{4A}$, together with the carbon atom to which they are attached, form a C(O); and $R^{5A}$ is H.

In certain embodiments, —$X^1$—$X^2$— is $C(R^{3A})$=N: $R^{3A}$ is H; and two $R^{4A}$, together with the carbon atom to which they are attached, form a C(O). In certain embodiments, —$X^1$—$X^2$— is $C(R_{3A})_2$—$C(R^{3A})_2$; $R^{3A}$ is H; and two $R^{4A}$, together with the carbon atom to which they are attached, form a C(O). In certain embodiments, —$X^1$—$X^2$— is $C(R^{3A})$=N; $R^{5A}$ is H; and two $R^{4A}$, together with the carbon atom to which they are attached, form a C(O). In certain embodiments, —$X^1$—$X^2$— is $C(R_{3A})_2$—$C(R^{3A})_2$; $R^{5A}$ is H; and two $R^{4A}$, together with the carbon atom to which they are attached, form a C(O).

In certain embodiments, D is thalidomide, lenalidomide, pomalidomide, CC-885 (Matyskiela et al., *Nature* 2016, 535, 252-257), 3-(5-amino-2-methyl-4-oxoquinazolin-3(4H)-yl)piperidine-2,6-dione, or an analogue or derivative thereof. In certain embodiments, D is thalidomide. In certain embodiments, D is lenalidomide.

In certain embodiments, D is:

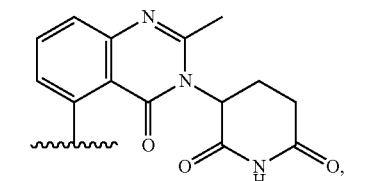

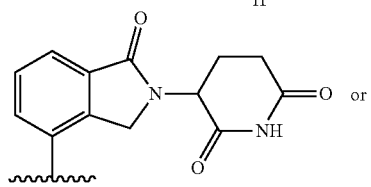

or

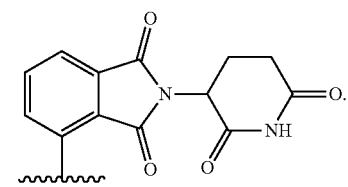

In certain embodiments, D is:

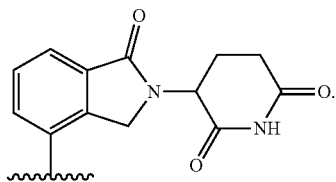 [SMILES: *c1cccc2c1CN(C1CCC(=O)NC1=O)C2=O]

In certain embodiments, D is

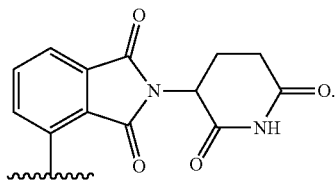 [SMILES: *c1cccc2c1C(=O)N(C1CCC(=O)NC1=O)C2=O]

In certain embodiments, D is of the formula:

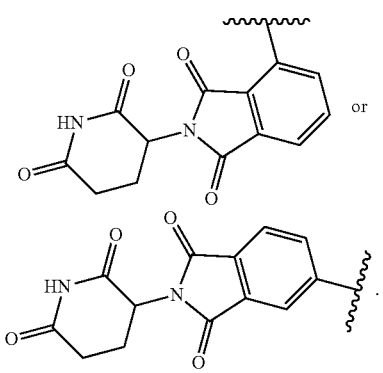

In certain embodiments, the E3 ligase binding moiety binds an E3 ubiquitin ligase with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety binds Cereblon with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety selectively binds an E3 ubiquitin ligase as compared to another protein. In some embodiments, the E3 ligase binding moiety selectively binds Cereblon over another protein. In some embodiments, the E3 ligase binding moiety selectively binds Cereblon over another E3 ubiquitin ligase. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Substituents A, Y, Z, $R^1$, $R^2$, $R^7$

Compounds of Formulae (I) and (I') are bifunctional compounds that bind to the ubiquitin receptor RPN13 on one end and bind to E3 ligase on the other end. For compounds of Formulae (I) and (I'), the E3 ligase binding moiety includes substituents A, Y, Z, $R^1$, and $R^2$.

In each pair of A's, one A is hydrogen, and the other A is one of:

(i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

(ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

(iii) a 5 or 6 membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR$ $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and (iv) an 8 to 10 membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$.

In each pair of A's, in some embodiments, one A is phenyl, optionally substituted with 1-5 substituents including $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, or $OCF_3$. In some embodiments, one A is phenyl. In some embodiments, one A is phenyl substituted with halogen. In some embodiments, in each pair of A's, one A is hydrogen; and the other A is phenyl, optionally substituted with $R^1$. In some embodiments, in each pair of A's, one A is hydrogen; and the other A is phenyl substituted with halogen (e.g., F, Cl, Br, or I).

In each pair of A's, in some embodiments, one A is naphthyl, optionally substituted with 1-5 substituents including $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, or $OCF_3$.

In some embodiments, in each pair of A's, one A is hydrogen; and the other A is phenyl, optionally substituted with $R^1$. In some embodiments, in each pair of A's, one A is hydrogen and the other A is phenyl substituted with halogen. In each pair of A's, one A is hydrogen and the other A is phenyl substituted with F. In some embodiments, in each pair of A's, one A is hydrogen and the other A is phenyl substituted with Cl. In some embodiments, in each pair of A's, one A is hydrogen and the other A is phenyl substituted with Br. In some embodiments, in each pair of A's, one A is hydrogen and the other A is phenyl substituted with I. In some embodiments, in each pair of A's, both A's are phenyl, optionally substituted with 1-5 substituents including $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, or $OCF_3$. In some embodiments, in each pair of A's, both A's are phenyl, optionally substituted with $R^1$.

In some embodiments, at least one instance of Y is selected from the group consisting of O, S, $NR^1$, and $CR^2$. In some embodiments, at least one instance of Y is O. In certain embodiments, both Y are O. In some embodiments, one instance of Y is O and the other instance of Y is —$CH_2$. In some embodiments, both instances of Y are —$CH_2$.

In some embodiments, $R^1$ and $R^2$ are selected from the group consisting of hydrogen, nitro, hydroxyl, carboxy, amino, halogen, cyano, and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano. In some embodiments, $R^1$ is substituted or unsubstituted alkyl (e.g., substituted or unsubstituted $C_{1-6}$ alkyl). In some embodiments, $R^1$ is halogen (e.g., F, Br, Cl). In some embodiments, $R^2$ is substituted or unsubstituted alkyl (e.g., substituted or unsubstituted $C_{1-6}$ alkyl). In some embodiments, all the instances of $R^1$ are the same.

In some embodiments, $R^7$ is hydrogen. In some embodiments, $R^7$ is $C_{1-6}$ alkyl (e.g., substituted or unsubstituted $C_{1-6}$ alkyl) (e.g., methyl, ethyl, or propyl)). In some embodiments, $R^7$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In some embodiments, Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; and —$(CH_2)_q$—K. In some embodiments, K is a 5 or 6 membered monocyclic heterocyclic ring, containing 1 to 4 atoms selected from oxygen, nitrogen, and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4. In certain embodiments, q is 0. In certain embodiments, q is 1. In certain embodiments, q is 2. In certain embodiments, q is 3. In certain embodiments, q is 4.

In some embodiments, Z is phenyl. In some embodiments, Z is benzyl. In some embodiments, Z is unsubstituted benzyl.

In certain embodiments, a compound of Formula (I) is of formula:

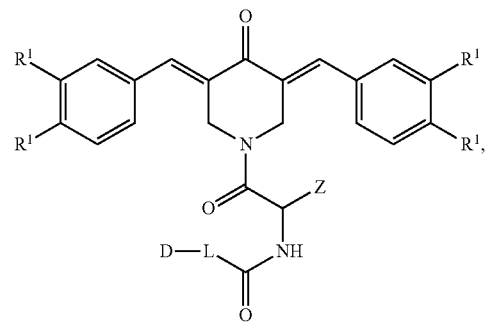

or a pharmaceutically acceptable salt thereof.

In certain embodiments, a compound of Formula (I) is of formula:

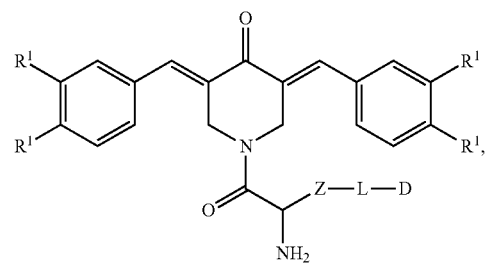

or a pharmaceutically acceptable salt thereof.

In certain embodiments, a compound of Formula (I) is of formula:

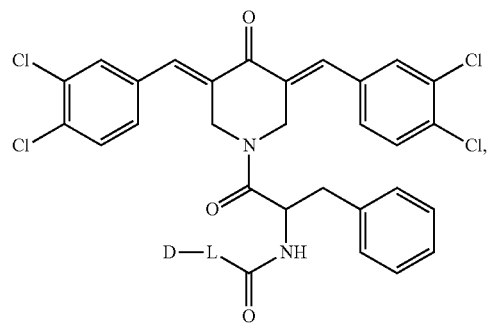

or a pharmaceutically acceptable salt thereof.

In certain embodiments, a compound of Formula (I) is of formula:

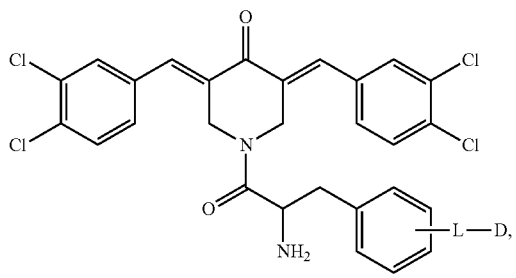

or a pharmaceutically acceptable salt thereof.

In certain embodiments, a compound of Formula (I) is of formula:

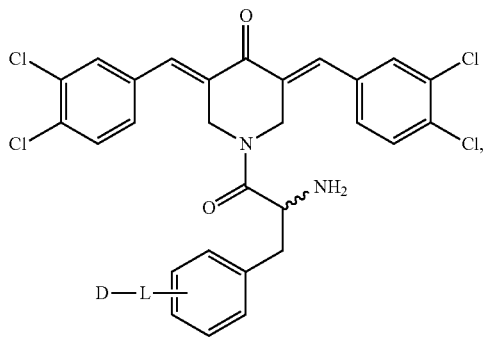

or a pharmaceutically acceptable salt thereof.

Linker L

In Formula (I), L is a divalent moiety linking the group D to the moiety of

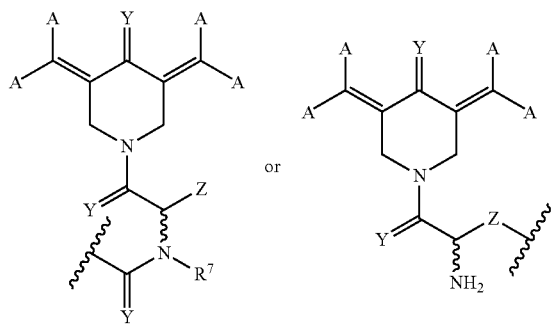

(i.e., the RPN13 binding moiety). In Formula (I), L covalently links the group D to the moiety of

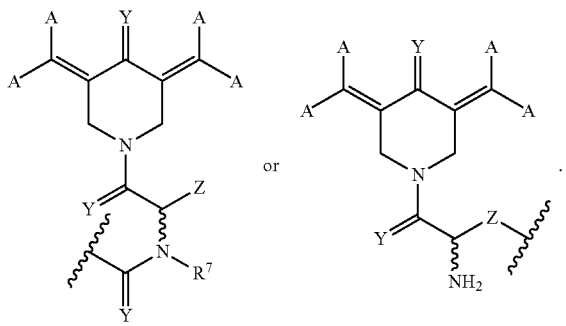

In Formulae (I) and (I'), L is a divalent moiety. In certain embodiments, L is a bond, a substituted or unsubstituted $C_{1-12}$ hydrocarbon chain, optionally wherein one or more chain atoms of the hydrocarbon chain are independently replaced with —C(=O)—, —O—, —S—, —NR$^b$—, —N=, or =N—, substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L is any "L0" group or "Linker" group recited in U.S. patent application U.S. Ser. No. 14/707,930, filed May 8, 2015, which is incorporated herein by reference. In certain embodiments, L is any "L" group recited in U.S. patent application U.S. Ser. No. 14/792,414, filed Jul. 6, 2015, which is incorporated herein by reference.

In certain embodiments, the chain of linker L comprises up to 50 atoms as the shortest path between D and the moiety of

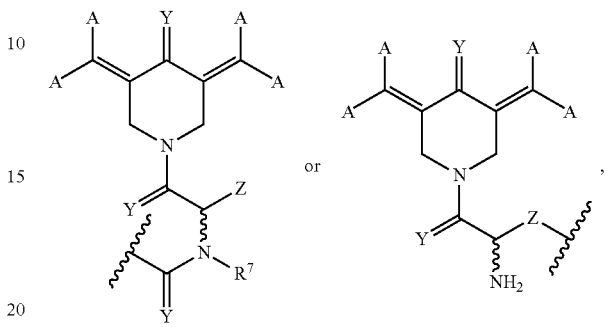

excluding hydrogen atoms. In certain embodiments, the chain of linker L comprises up to 50 atoms, excluding hydrogen atoms. In certain embodiments, L comprises up to 40 atoms, excluding hydrogen atoms. In certain embodiments, L comprises up to 30 atoms, excluding hydrogen atoms. In certain embodiments, L comprises up to 20 atoms, excluding hydrogen atoms. In certain embodiments, L comprises up to 14 atoms, excluding hydrogen atoms. In certain embodiments, L comprises up to 15 atoms, excluding hydrogen atoms. In certain embodiments, L comprises up to 12 atoms, excluding hydrogen atoms. In certain embodiments, L comprises up to 10 atoms, excluding hydrogen atoms. In certain embodiments, L comprises up to 9 atoms excluding hydrogen atoms. In certain embodiments, L comprises up to 6 atoms excluding hydrogen atoms. In certain embodiments, L comprises up to 5 atoms excluding hydrogen atoms. In certain embodiments, L comprises up to 3 atoms excluding hydrogen atoms.

In certain embodiments, any of the atoms in L can be substituted. In certain embodiments, none of the atoms in the linker L are substituted. In certain embodiments, none of the carbon atoms in the linker are substituted.

In certain embodiments, L is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, each instance of R$^b$ is independently hydrogen, substituted or unsubstituted $C_{1-6}$ alkyl, or a nitrogen protecting group, or optionally two instances of R$^b$ are taken together with their intervening atoms to form a substituted or unsubstituted heterocyclic or substituted or unsubstituted heteroaryl ring.

In certain embodiments, L is a substituted or unsubstituted $C_{1-14}$ hydrocarbon chain, optimally wherein one or more chain atoms of the hydrocarbon chain are independently replaced with —O— or —NR$^b$—. In certain embodiments, L is a substituted or unsubstituted $C_{12-14}$ hydrocarbon chain, optimally wherein one or more chain atoms of the hydrocarbon chain are independently replaced with —O— or —NR$^b$—. In certain embodiments, L is a substituted or unsubstituted $C_{14}$ hydrocarbon chain, optimally wherein one or more chain atoms of the hydrocarbon chain are independently replaced with —O— or —NR$^b$—. In certain embodiments, L is a substituted or unsubstituted $C_{12}$ hydrocarbon chain, optimally wherein one or more chain atoms of the hydrocarbon chain are independently replaced with —O— or —NR$^b$—. In certain embodiments, L is a substituted or unsubstituted C$_{1-12}$ hydrocarbon chain, optimally wherein one or more chain atoms of the hydrocarbon chain are independently replaced with —O— or —NR$^b$—. In certain embodiments, L is a substituted or unsubstituted C$_{8-12}$ hydrocarbon chain, optimally wherein one or more chain atoms of the hydrocarbon chain are independently replaced with —O— or —NR$^b$—. In certain embodiments, L is a substituted or unsubstituted C$_8$ hydrocarbon chain, optimally wherein one or more chain atoms of the hydrocarbon chain are independently replaced with —O— or —NR$^b$—. In certain embodiments, L is a substituted or unsubstituted C$_{12}$ hydrocarbon chain, optimally wherein one or more chain atoms of the hydrocarbon chain are independently replaced with —O— or —NR$^b$—. In certain embodiments, L is a substituted or unsubstituted C$_{1-12}$ hydrocarbon chain. In certain embodiments, one or more chain atoms of the hydrocarbon chain of L are independently replaced with —C(=O)—, —O—, —S—, —NR$^b$—, —N=, or =N—. In certain embodiments, L is a substituted or unsubstituted C$_{1-12}$ hydrocarbon chain, wherein one chain atom of the hydrocarbon chain is independently replaced with —O—. In certain embodiments, L is an unsubstituted C$_{1-3}$ hydrocarbon chain.

In certain embodiments, L is an all-carbon, substituted or unsubstituted C$_{6-12}$ hydrocarbon chain.

In certain embodiments, L is an all-carbon, substituted or unsubstituted C$_{1-12}$ hydrocarbon chain. In certain embodiments, L is an all-carbon, substituted or unsubstituted C$_{1-6}$ hydrocarbon chain. In certain embodiments, L is of the formula:

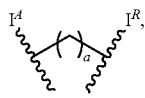

wherein a is 0, 1, 2, 3, 4, 5, or 6. In certain embodiments, a is 0. In certain embodiments, L is a bond. In certain embodiments, a is 1. In certain embodiments, a is 2. In certain embodiments, a is 3. In certain embodiments, a is 4. In certain embodiments, a is 5. In certain embodiments, a is 6. In certain embodiments, L is of the formula:

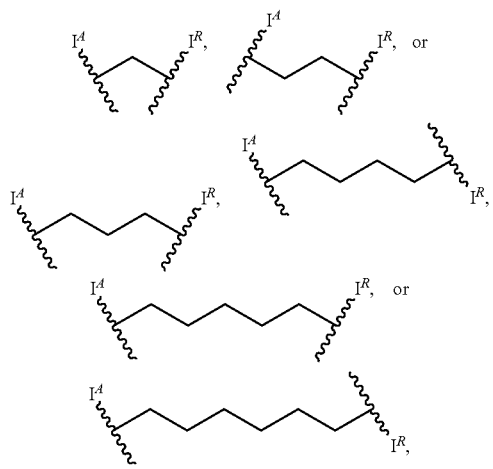

wherein $l^A$ indicates the point of attachment to D, and $l^R$ indicates the point of attachment to the moiety of formula

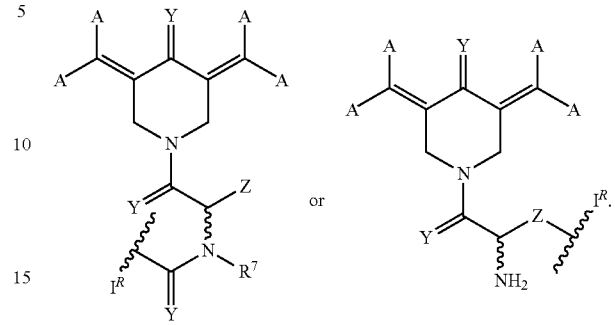

In certain embodiments, L is of the formula:

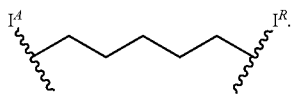

In certain embodiments, L is a substituted or unsubstituted C$_{1-12}$ hydrocarbon chain, optionally wherein one or more chain atoms of the hydrocarbon chain are independently replaced with —C(=O)—, —O—, —S—, —NR$^b$—, —N=, or =N—. In certain embodiments, L is an unsubstituted C$_{1-12}$ hydrocarbon chain, wherein one or more chain atoms of the hydrocarbon chain are independently replaced with —O— or —NR$^b$—. In certain embodiments, L is an unsubstituted C$_{1-2}$ hydrocarbon chain, wherein one chain atom of the hydrocarbon chain is replaced with —O—. In certain embodiments, L is of the formula:

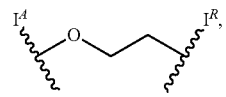

wherein $l^A$ indicates the point of attachment to D, and $l^R$ indicates the point of attachment to the

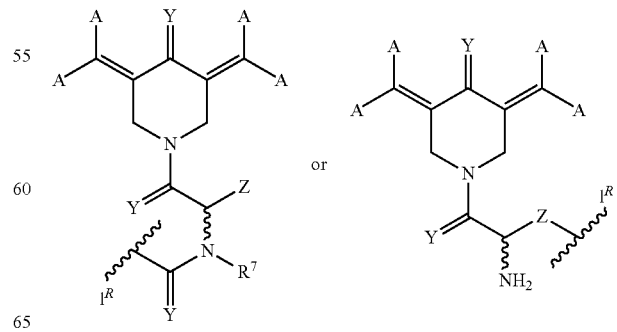

moiety. In certain embodiments, L is of the formula:

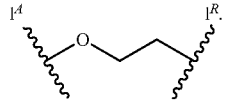

In certain embodiments, L is a substituted $C_{1-6}$ hydrocarbon chain, wherein one chain atom of the hydrocarbon chain is replaced with —N—. In certain embodiments, L is of the formula:

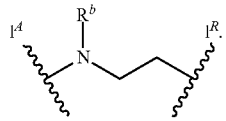

In certain embodiments, L is of the formula:

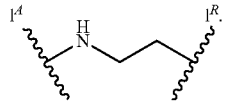

In certain embodiments, L is of the formula:

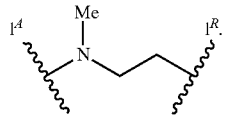

In certain embodiments, L is of the formula:

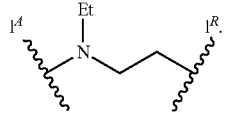

In certain embodiments, L is an unsubstituted $C_{1-3}$ hydrocarbon chain, wherein one chain atom of the hydrocarbon chain is replaced with —C(=O)—. In certain embodiments, L is an unsubstituted $C_{1-3}$ hydrocarbon chain, wherein one chain atom of the hydrocarbon chain is replaced with —S—. In certain embodiments, L is an unsubstituted $C_{1-3}$ hydrocarbon chain, wherein one chain atom of the hydrocarbon chain is replaced with —$NR^b$—. In certain embodiments, L is an unsubstituted $C_{1-3}$ hydrocarbon chain, wherein one chain atom of the hydrocarbon chain is replaced with —N=. In certain embodiments, L is an unsubstituted $C_{1-3}$ hydrocarbon chain, wherein one chain atom of the hydrocarbon chain is replaced with =N—.

In certain embodiments, L is of the formula:

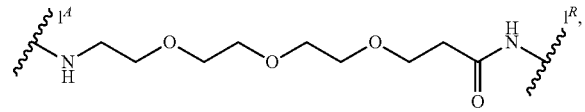

-continued

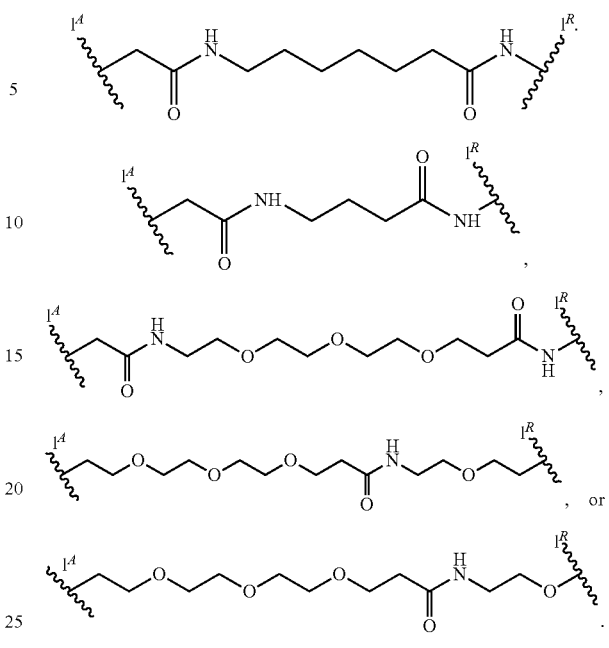

In certain embodiments, L is of the formula:

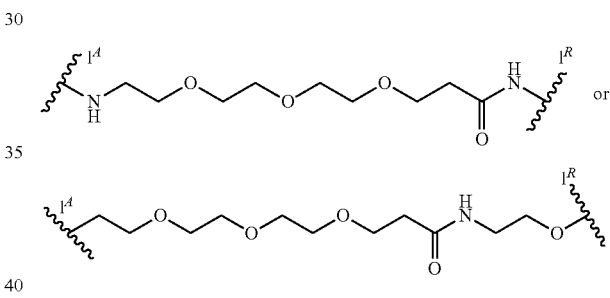

In certain embodiments, L is L is

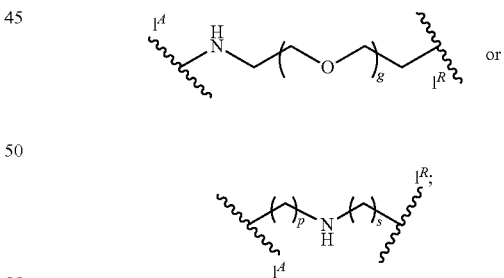

and g is 2, 3, or 4; p is 0, 1, 2, 3, 4, or 5; and s is 1, 2, 3, 4, 5, or 6. In certain embodiments, g is 2. In certain embodiments, g is 3. In certain embodiments, g is 4. In certain embodiments, p is 0. In certain embodiments, p is 1. In certain embodiments, p is 2. In certain embodiments, p is 3. In certain embodiments, p is 4. In certain embodiments, p is 5. In certain embodiments, s is 1. In certain embodiments, s is 2. In certain embodiments, s is 3. In certain embodiments, s is 4. In certain embodiments, s is 5. In certain embodiments, s is 6. In certain embodiments, L is

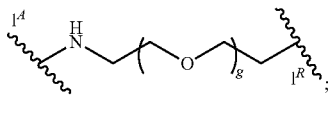

and g is 2, 3, or 4. In certain embodiments, L is

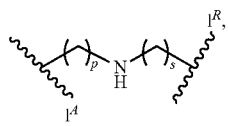

wherein p is 0 and s is 2, 3, 4, 5, or 6. In certain embodiments, L is

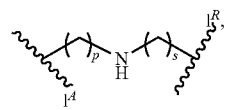

wherein p is 0; and s is 4, 5, or 6. In certain embodiments, p is 0; and s is 2, 3, 4, 5, or 6. In certain embodiments, p is 0; and s is 3, 4, or 5. In certain embodiments, s is 3, 4, or 5.

In certain embodiments, L is

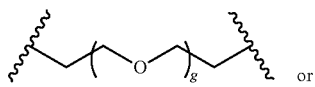

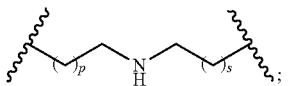

g is 1-5; p is 2-5; and s is 1-5. In certain embodiments, g is 1. In certain embodiments, g is 2. In certain embodiments, g is 3. In certain embodiments, g is 4. In certain embodiments, g is 5. In certain embodiments, p is 2. In certain embodiments, p is 3. In certain embodiments, p is 4. In certain embodiments, p is 5. In certain embodiments, s is 1. In certain embodiments, s is 2. In certain embodiments, s is 3. In certain embodiments, s is 4. In certain embodiments, s is 5. In certain embodiments, L is an all-carbon, substituted or unsubstituted $C_{1-12}$ hydrocarbon chain. In certain embodiments, L is an all-carbon, substituted $C_{1-12}$ hydrocarbon chain. In certain embodiments, L is an all-carbon, unsubstituted $C_{1-12}$ hydrocarbon chain.

In certain embodiments, L is of the formula:

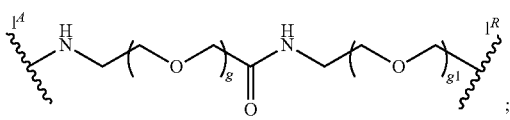

g is 1-5; and g1 is 1-5. In certain embodiments, g is 1, 2, 3, 4, or 5. In certain embodiments, g1 is 1, 2, 3, 4, or 5. In certain embodiments, L is of the formula:

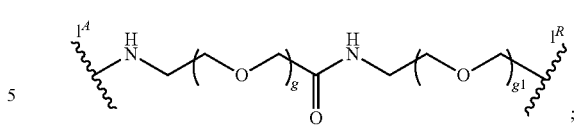

g is 3 or 4; and g1 is 3 or 4. In certain embodiments, L is of the formula:

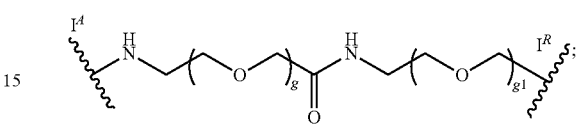

g is 3; and g1 is 3 or 4. In certain embodiments, g is 1. In certain embodiments, g is 2. In certain embodiments, g is 3. In certain embodiments, g is 4. In certain embodiments, g is 5. In certain embodiments, g1 is 1. In certain embodiments, g1 is 2. In certain embodiments, g1 is 3. In certain embodiments, g1 is 4. In certain embodiments, g1 is 5.

In certain embodiments, L is

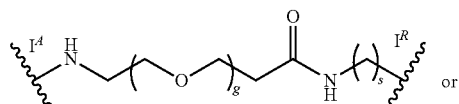

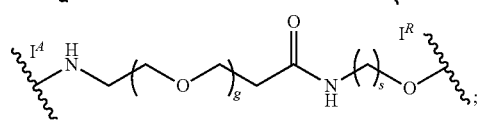

g is 1, 2, 3, 4, or 5; and s is 2, 3, or 4. In certain embodiments, L is

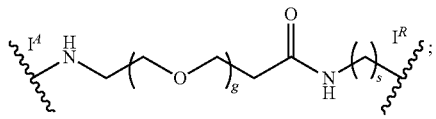

g is 3 or 4; and s is 2, 3, or 4. In certain embodiments, L is

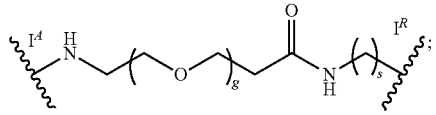

g is 3 or 4; and s is 2 or 3. In certain embodiments, L is

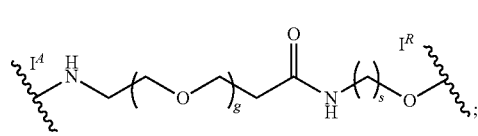

g is 3 or 4; and s is 2, 3, or 4. In certain embodiments, L is

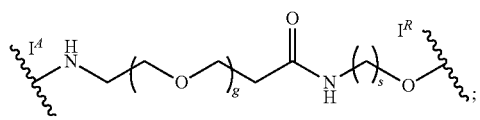

g is 3 or 4; and s is 2 or 3. In certain embodiments, g is 1. In certain embodiments, g is 2. In certain embodiments, g is 3. In certain embodiments, g is 4. In certain embodiments, g is 5. In certain embodiments, s is 2. In certain embodiments, s is 3. In certain embodiments, s is 4.

In certain embodiments, L is of the formula:

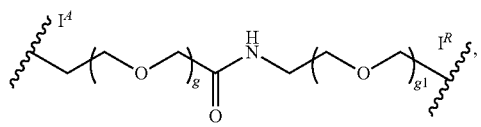

wherein: g is 1-5; and g1 is 1-5. In certain embodiments, g is 1. In certain embodiments, g is 2. In certain embodiments, g is 3. In certain embodiments, g is 4. In certain embodiments, g is 5. In certain embodiments, g1 is 1. In certain embodiments, g1 is 2. In certain embodiments, g1 is 3. In certain embodiments, g1 is 4. In certain embodiments, g1 is 5. In certain embodiments, L is of the formula:

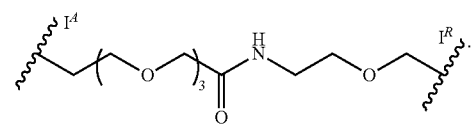

In certain embodiments, L is of the formula:

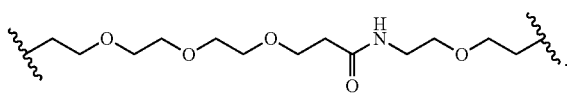 [SMILES: *CCOCCNC(=O)CCOCCOCCOCC*]

In certain embodiments, L is of the formula:

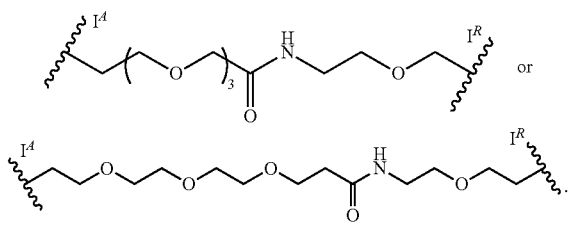

In certain embodiments, L is of the formula:

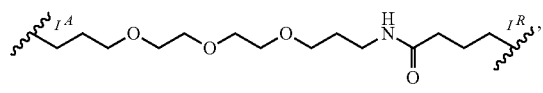

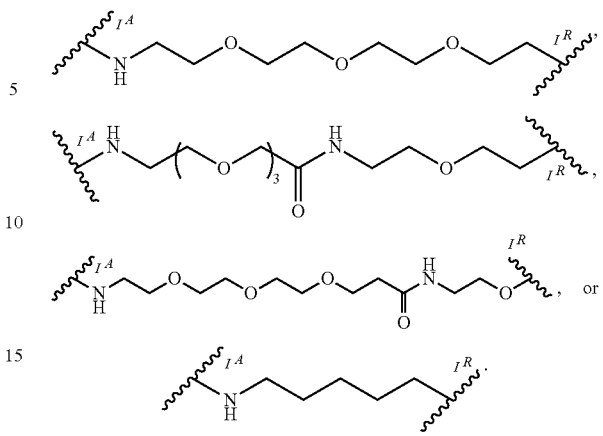

In certain embodiments, L is of the formula:

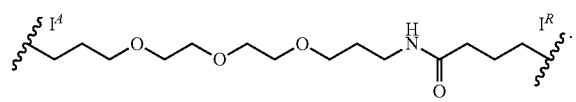

In certain embodiments, L is of the formula:

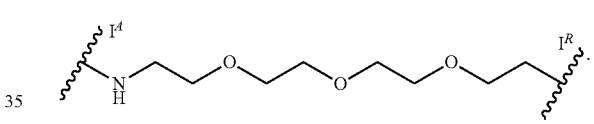

In certain embodiments, L is of the formula:

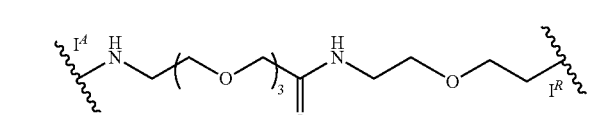

In certain embodiments, L is of the formula:

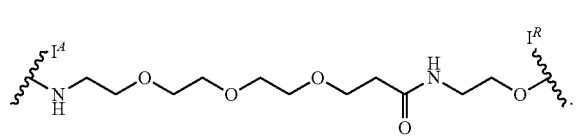

In certain embodiments, L is of the formula:

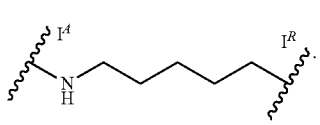

In certain embodiments, a compound of Formulae (I) or (I') is of the formula:

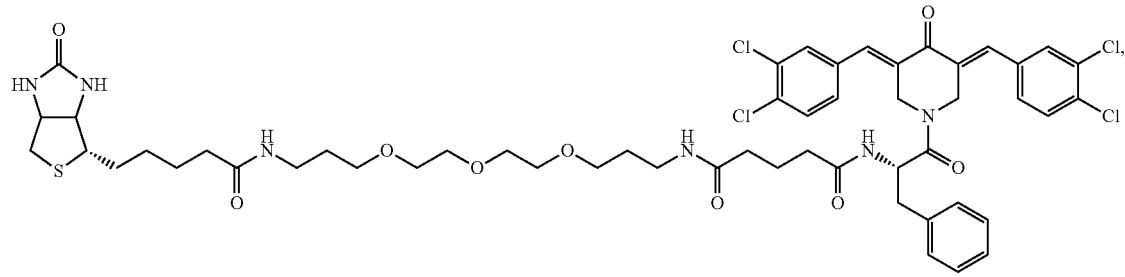
(LW-RPN13-4)
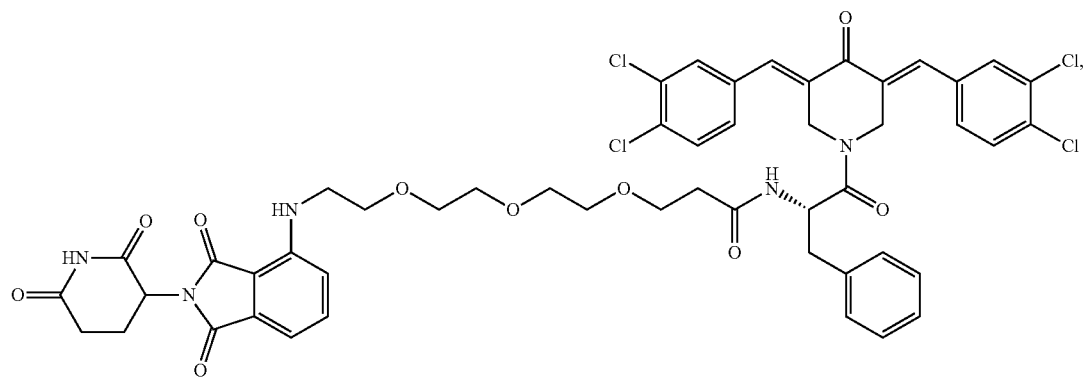
(LW-RPN13-4; WL-40)
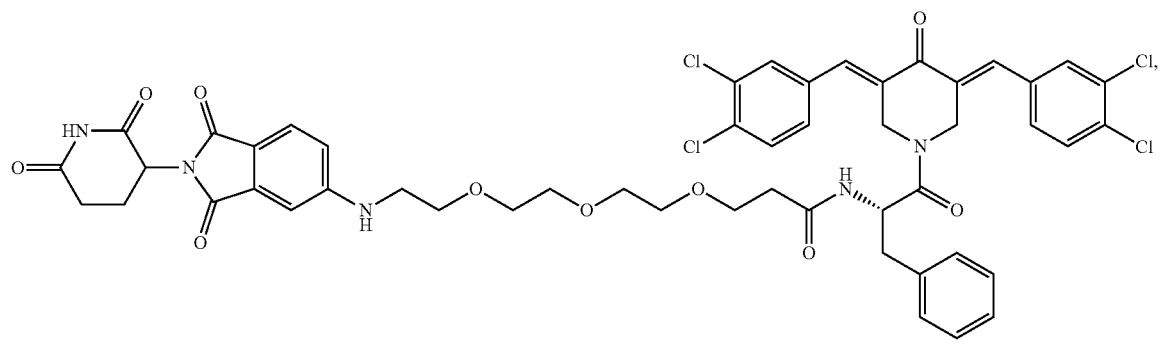
(LW-RPN13-2)
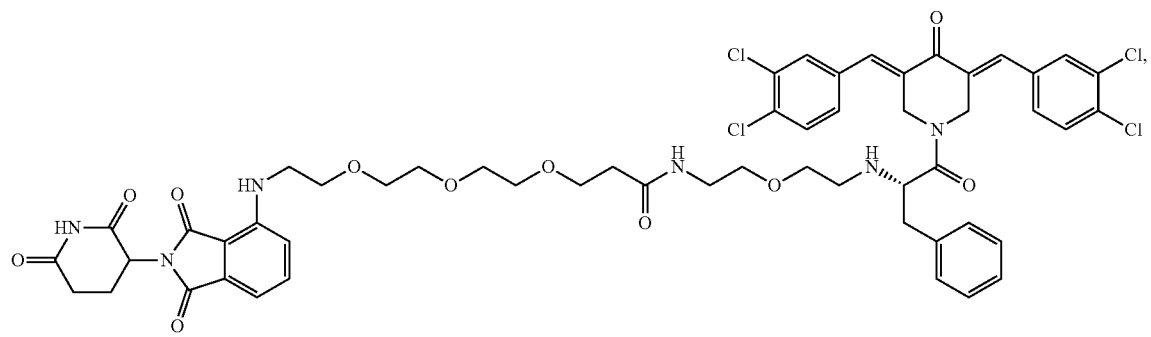
(dRPN13-3)

-continued
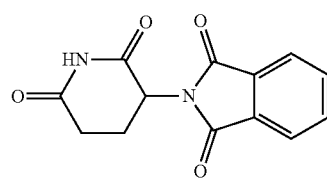
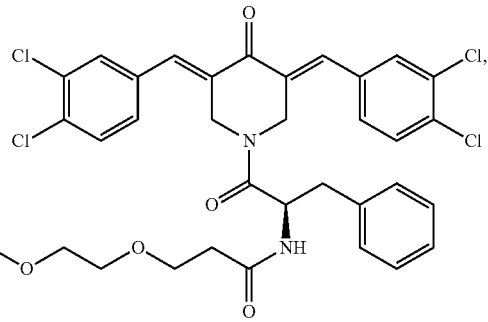
(WL44)
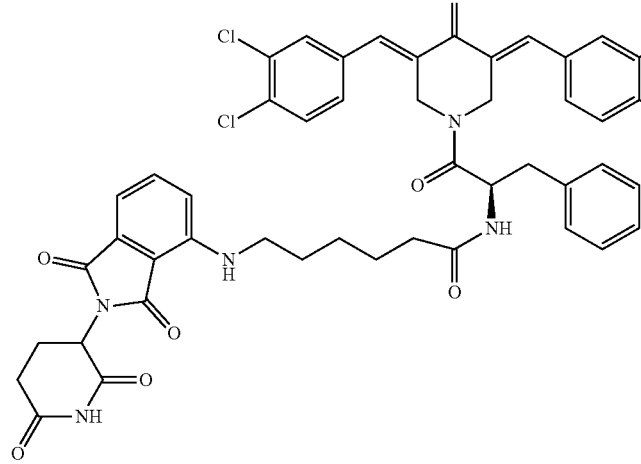
(WL4)
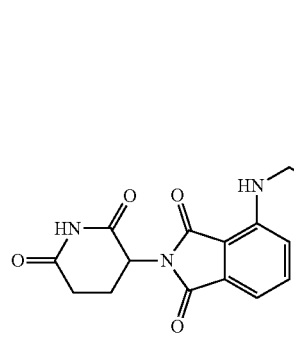
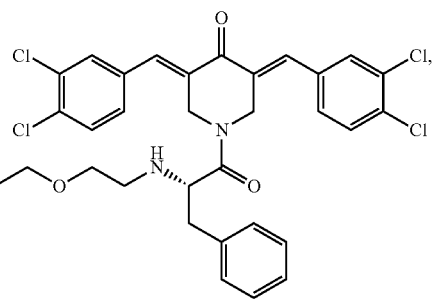
JQRA
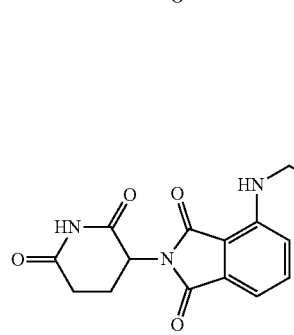
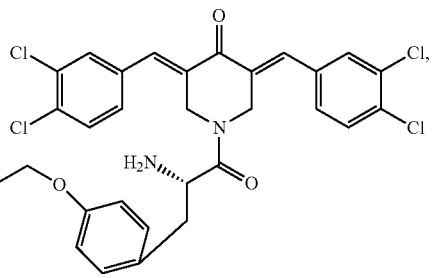
or a pharmaceutically acceptable salt, solvate, hydrate, tautomer, or stereoisomer thereof.

In certain embodiments, a compound of Formulae (I) or (I') is of the formula:
(LW-RP13-4)
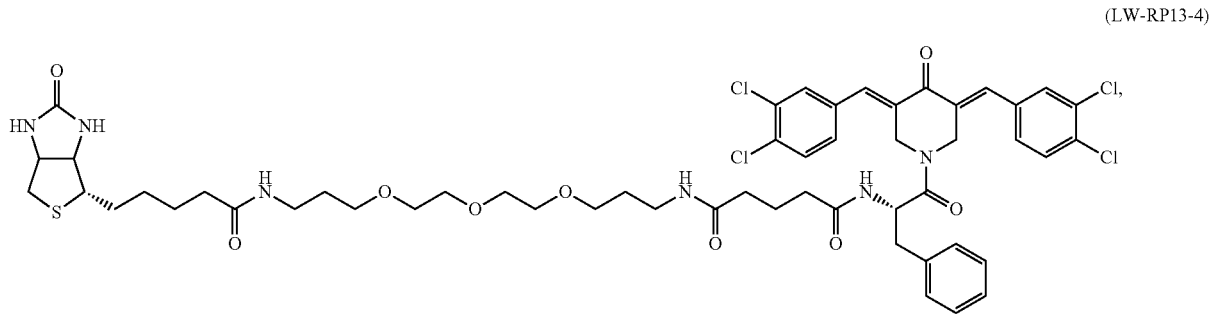
(LW-RPN13-1; WL-40)
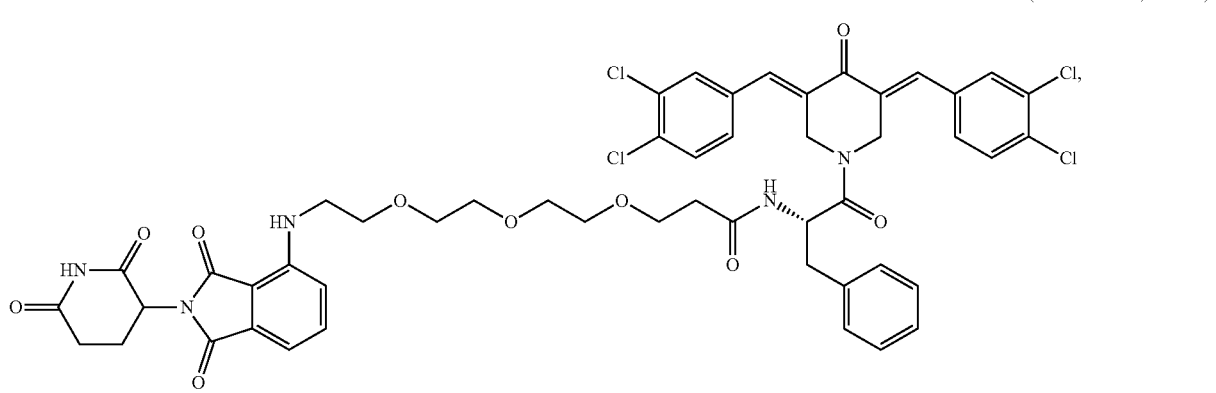
(LW-RPN13-2)
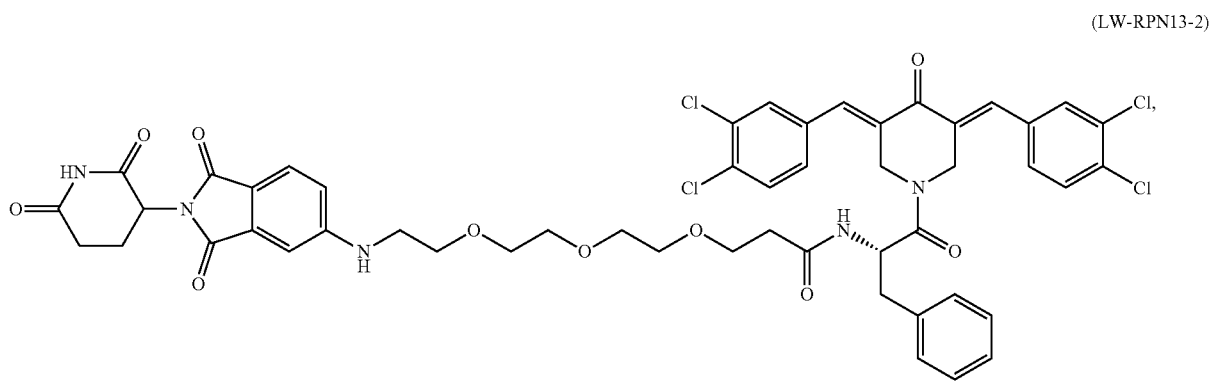
(dRPN13-3)
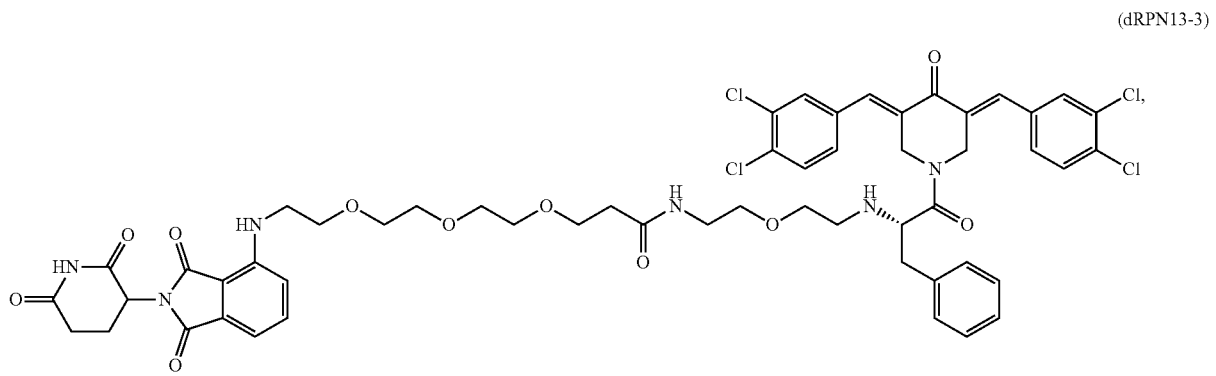

-continued
(WL44)
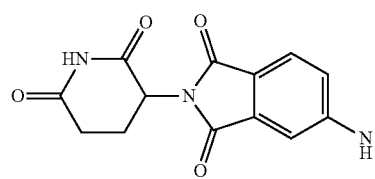 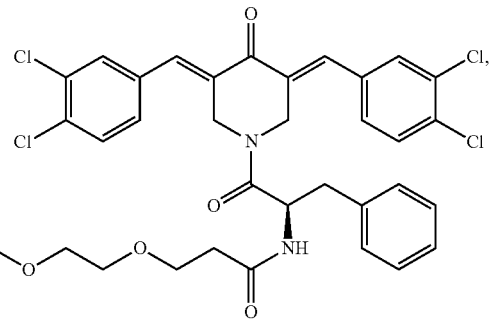
(WL4)
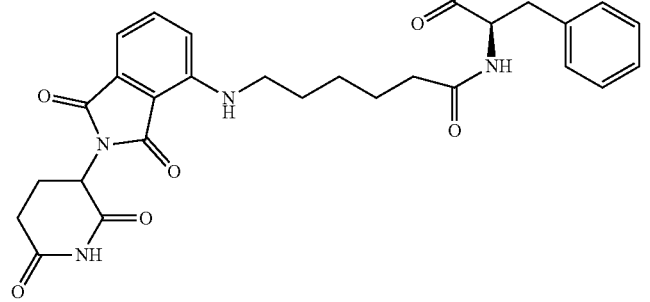
JQRA
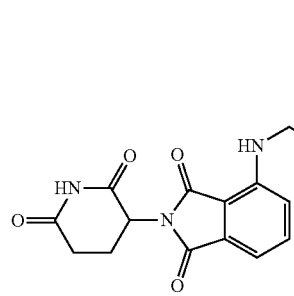 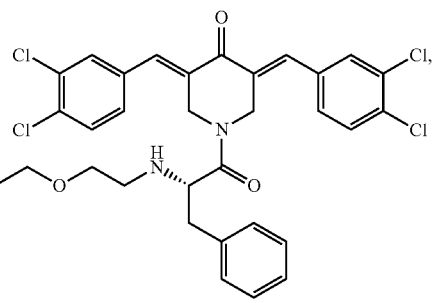
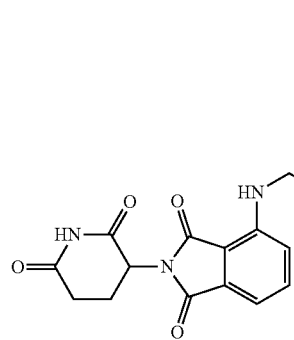 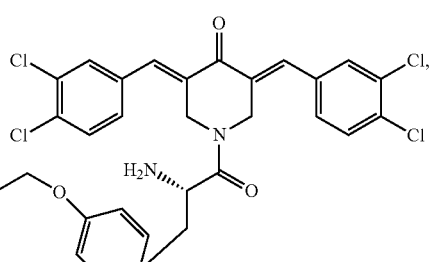

or a pharmaceutically acceptable salt, solvate, hydrate, tautomer, or stereoisomer thereof.

In certain embodiments, a compound of Formulae (I) or (I') is a final product compound depicted in Example 1. In certain embodiments, a compound of Formulae (I) or (I') is a product compound depicted in Example 2. In certain embodiments, a compound of Formulae (I) or (I') is a product compound depicted in Example 1 or Example 2. In certain embodiments, a compound of Formulae (I) or (I') is a product compound depicted in one of the Figures.

In some embodiments, the compound of Formulae (I) or (I') selectively binds ubiquitin receptor RPN13 over another protein. In some embodiments, the compound of Formulae (I) or (I') selectively binds ubiquitin receptor RPN13 over another ubiquitin receptor. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formulae (I) or (I') induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the ubiquitin receptor RPN13 at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formulae (I) or (I') increases the rate of degradation of the ubiquitin receptor RPN13 up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formulae (I) or (I'), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formulae (I) or (I'), or a pharmaceutically acceptable salt thereof, and a pharmaceutically acceptable excipient.

In certain embodiments, the compound of Formulae (I) or (I') is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for reducing the risk of developing a disease (e.g., proliferative disease or cancer) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inducing the degradation of at least about 10%, at least about 20%, at least about 30%, at least about 40%, at least about 50%, at least about 60%, at least about 70%, at least about 80%, at least about 90%, at least about 95%, at least about 98%, or at least about 99% of the ubiquitin receptor RPN13 in a cell. In certain embodiments, the effective amount is an amount effective for inducing the degradation of ubiquitin receptor RPN13 in a cell by a range between a percentage described in this paragraph and another percentage described in this paragraph, inclusive.

The present disclosure provides pharmaceutical compositions comprising a compound that interacts with a E3 ubiquitin ligase (e.g., cereblon) and the ubiquitin receptor RPN13 for use in treating a proliferative disease in a subject in need thereof. In certain embodiments, the composition is for use in treating a neurodegenerative disease. In certain embodiments, the composition is for use in treating cancer. In certain embodiments, the composition is for use in treating multiple myeloma, leukemia, lymphoma, or a cancer resistant to a proteasome inhibitor. In certain embodiments, the composition is for use in treating cancer resistant to bortezomib. In certain embodiments, the composition is for use in treating cancer resistant to carfilzomib. In certain embodiments, the composition is for use in treating multiple myeloma.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inducing the degradation of a target protein, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEG ACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-/trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for inducing the degradation of RPN13 in a subject, biological sample, tissue, or cell. In certain embodiments, the kits and instructions provide for inducing apoptosis in a cell. A kit described herein may include one or more additional pharmaceutical agents described herein as a separate composition.

Methods of Treatment and Uses

The compounds described herein are capable of binding (e.g., reversibly binding or irreversibly binding) an E3 ubiquitin ligase (e.g., Cereblon) and RPN13 and inducing the degradation of RPN13. The present disclosure thus also provides methods of inducing the degradation of RPN13 in a subject, biological sample, tissue, or cell. The present disclosure further provides methods for the treatment of a wide range of diseases, such as proliferative diseases, inflammatory diseases, autoimmune diseases, genetic diseases, hematological diseases, neurological diseases, painful conditions, psychiatric disorders, and metabolic disorders in a subject in need thereof.

In certain embodiments, the application provides a method of binding an ubiquitin receptor RPN13 and promoting the degradation of RPN13. In another aspect, the present disclosure provides methods of inducing the degradation of RPN13 in a subject in need thereof, the methods comprise administering to the subject an effective amount of a compound or pharmaceutical composition described herein. In another aspect, the present disclosure provides methods of inducing the degradation of RPN13 in a biological sample, tissue, or cell, the methods comprise contacting the biological sample, tissue, or cell with an effective amount of a compound or pharmaceutical composition described herein.

In certain embodiments, the application provides a method of binding an E3 ubiquitin ligase (e.g., Cereblon) and RPN13 and inducing the degradation of ubiquitin receptor RPN13. In certain embodiments, the ubiquitin receptor is RPN13. In certain embodiments, the ubiquitin receptor is RPN13. In certain embodiments, the binder of the ubiquitin receptor RPN13 is RA190 (below).

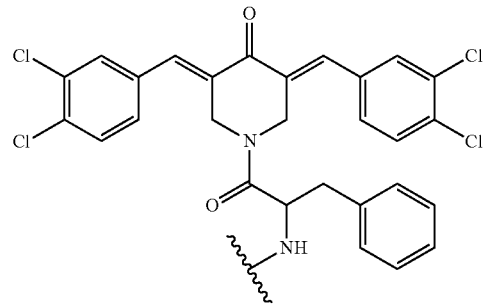

(RA190)

Use of a bifunctional compound that binds an E3 ubiquitin ligase (e.g., Cereblon) and a ubiquitin receptor RPN13 provides a strategy for treating diseases associated with RPN13 (e.g. proliferative diseases).

The present disclosure also provides a compound of Formulae (I) or (I'), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof.

The present disclosure also provides uses of a compound of Formulae (I) or (I'), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof.

In certain embodiments, the methods of the disclosure comprise administering to the subject an effective amount of a compound of Formulae (I) or (I'), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formulae (I) or (I'), or at different times than the compound of Formulae (I) or (I'). For example, the compound of Formulae (I) or (I') and any additional pharmaceutical agent(s) may be on the same dosing schedule or different dosing schedules. All or some doses of the compound of Formulae (I) or (I') may be administered before all or some doses of an additional pharmaceutical agent, after all or some does an additional pharmaceutical agent, within a dosing schedule of an additional pharmaceutical agent, or a combination thereof. The timing of administration of the compound of Formulae (I) or (I') and additional pharmaceutical agents may be different for different additional pharmaceutical agents.

In certain embodiments, the additional pharmaceutical agent comprises an agent useful in the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof. In certain embodiments, the additional pharmaceutical agent is useful in the treatment of a proliferative disease. In certain embodiments, the additional pharmaceutical agent is useful in the treatment of an inflammatory disease. In certain embodiments, the additional pharmaceutical agent is useful in the treatment of proliferative diseases, inflammatory diseases, autoimmune diseases, genetic diseases, hematological diseases, neurological diseases, painful conditions, psychiatric disorders, or metabolic disorders. In certain embodiments, the additional pharmaceutical agent is useful in the treatment of multiple myeloma. In certain embodiments, the additional pharmaceutical agent is useful in the treatment of leukemia. In certain embodiments, the additional pharmaceutical agent is useful in the treatment of lymphoma. In certain embodiments, the additional pharmaceutical agent is useful in the treatment of a non-Hodgkin's lymphoma. In certain embodiments, the additional pharmaceutical agent is useful in the treatment of cancer resistant to proteasome inhibitors (e.g., resistant to bortezomib or resistant to carfilzomib). In certain embodiments, the additional pharmaceutical agent is useful in the treatment of cancer resistant to bortezomib. In certain embodiments, the additional pharmaceutical agent is useful in the treatment of cancer resistant to carfilzomib.

In another aspect, the present disclosure provides methods for inducing the degradation of RPN13, the method comprising administering to the subject a compound of Formulae (I) or (I'), or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding an E3 ubiquitin ligase and promoting the degradation of a ubiquitin receptor RPN13, the method comprising administering to the subject a compound of Formulae (I) or (I'), or a pharmaceutically acceptable salt, co-crystal, tautomer, stereoisomer, solvate, hydrate, polymorph, isotopically enriched derivative, or prodrug, or composition thereof. In one aspect, the present disclosure provides methods for inducing the ubiquitination of RPN13. In one aspect, the present disclosure provides methods for inhibiting and/or blocking proteasome function in a subject. In one aspect, the present disclosure provides methods for inhibiting and/or blocking proteasome function in a cell.

In still another aspect, the present disclosure provides the pharmaceutical compositions described herein for use in binding an E3 ubiquitin ligase and RPN13 and promoting the degradation of a ubiquitin receptor RPN13; inducing the ubiquitination of RPN13 in a subject, biological sample, tissue, or cell; treating and/or preventing proliferative diseases, inflammatory diseases, autoimmune diseases, genetic diseases, hematological diseases, neurological diseases, painful conditions, psychiatric disorders, and metabolic disorders; and inhibiting and/or blocking proteasome function in a cell. The present disclosure provides methods of inducing apoptosis of a cell in a subject, the method comprising administering to the subject a therapeutically effective amount of a compound described herein.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using the following general methods and procedures or methods known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Compounds of Formulae (I) or (I') may be prepared using the synthetic schemes and procedures described in detail below.

Example 1. Experimental Procedures for Synthesis of RPN13 Compounds

Synthesis of LW-RPN13-4

In an exemplary synthesis, LW-RPN13-4 was synthesized using the steps shown in Scheme 1.

Scheme 1. Examplary synthesis of LW-RPN13-4

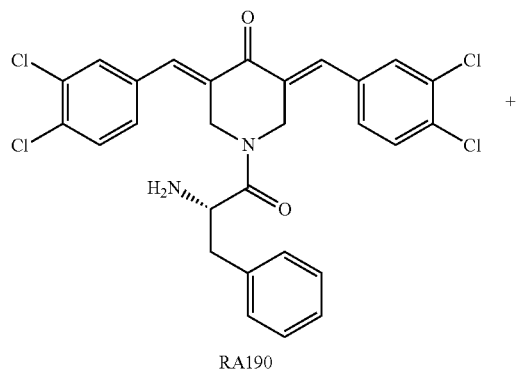

RA190

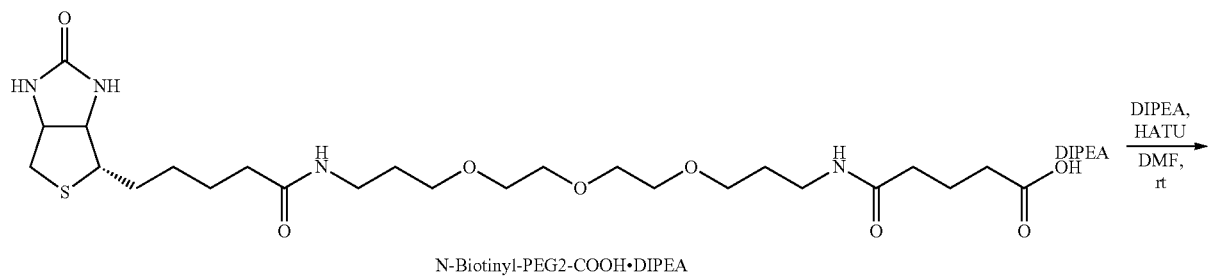

N-Biotinyl-PEG2-COOH•DIPEA

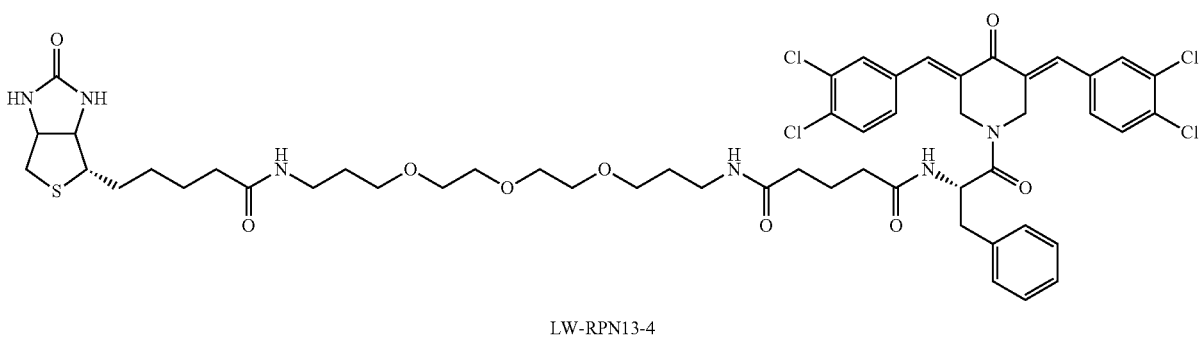

LW-RPN13-4

(1) A4-((S)-1-(3,5-bis((E)-3,4-dichlorobenzylidene)-4-oxopiperidin-1-yl)-1-oxo-3-phenylpropan-2-yl)-$N^5$-(15-oxo-19-((4S)-2-oxohexahydro-1H-thieno[3,4-d]imidazol-4-yl)-4,7,10-trioxa-14-azanonadecyl)glutaramide: To a solution of N-Biotinyl-(PEG)2-COOH.DIPEA (20 atoms) (5.37 mg, 0.0077 mmol), RA190 (4.46 mg, 0.0080 mmol) and HATU (4.36 mg, 0.0115 mmol) in DMF (0.2 mL) was added DIPEA (6 mg, 0.0400 mmol) at room temperature. The reaction mixture was stirred at room temperature for 15 minutes, and purified via HPLC (0.1% TFA/MeCN) to afford LW-RPN13-4 (6.79 mg). MS: m/z (M+1)$^+$: 1103.42.

Synthesis of LW-RPN13-1

In an exemplary synthesis, LW-RPN13-1 was synthesized using the steps shown in Scheme 2.

Scheme 2. Examplary synthesis of LW-RPN13-1

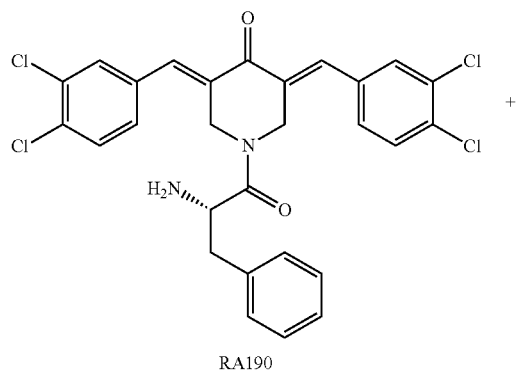
RA190

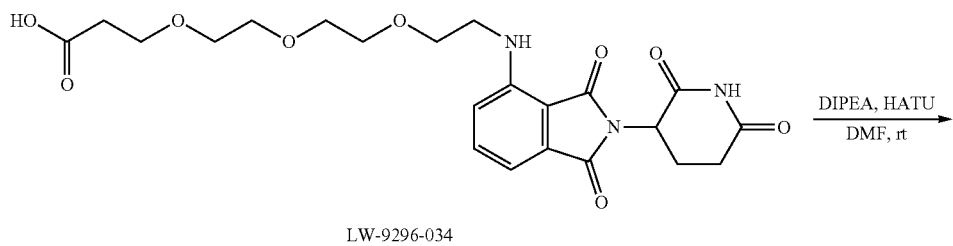
LW-9296-034

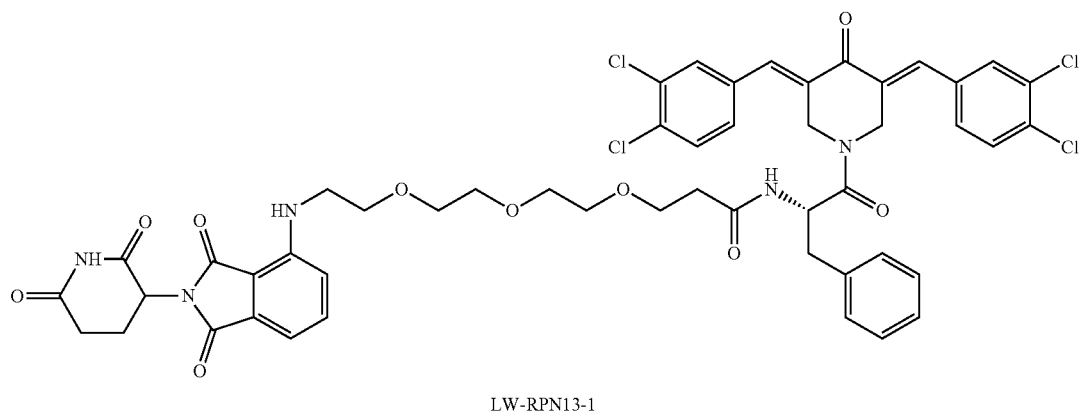
LW-RPN13-1

(2)N—((S)-1-(3,5-bis((E)-3,4-dichlorobenzylidene)-4-oxopiperidin-1-yl)-1-oxo-3-phenylpropan-2-yl)-3-(2-(2-(2-((2-(2,6-dioxopiperidin-3-yl)-1,3-dioxoisoindolin-4-yl)amino)ethoxy)ethoxy)ethoxy)propanamide: To a solution of LW-9296-034 (3.2 mg, 0.0067 mmol), RA190 (4 mg, 0.0070 mmol) and HATU (2.80 mg, 0.0074 mmol) in DMF (0.2 mL) was added DIPEA (8.6 mg, 0.067 mmol) at room temperature. The reaction mixture was stirred at room temperature for 15 minutes, and purified via HPLC (0.1% TFA/MeCN) to afford LW-RPN13-1 (4.32 mg). MS: m/z (M+1)$^+$: 1021.08.

Synthesis of LW-RPN13-2

In an exemplary synthesis, LW-RPN13-2 was synthesized using the steps shown in Scheme 3.

Scheme 3. Exemplary synthesis of LW-RPN13-2

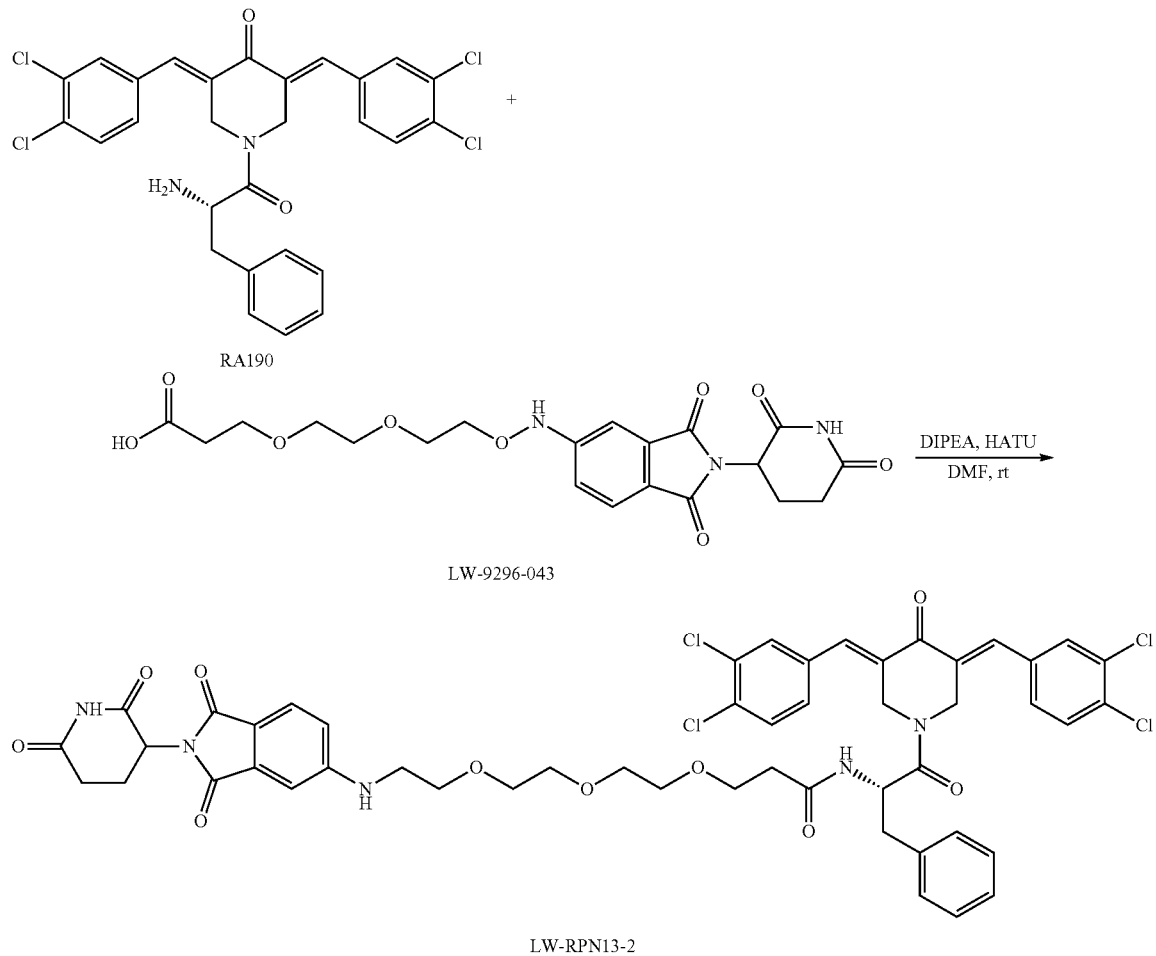

(3)N-((5)-1-(3,5-bis((E)-3,4-dichlorobenzylidene)-4-oxopiperidin-1-yl)-1-oxo-3-phenylpropan-2-yl)-3-(2-(2-(2-((2-(2,6-dioxopiperidin-3-yl)-1,3-dioxoisoindolin-5-yl)amino)ethoxy)ethoxy)ethoxy)propanamide: To a solution of LW-9296-043 (3.43 mg, 0.0072 mmol), RA190 (4.14 mg, 0.0074 mmol) and HATU (3.01 mg, 0.0080 mmol) in DMF (0.2 mL) was added DIPEA (9.3 mg, 0.072 mmol) at room temperature. The reaction mixture was stirred at room temperature for 15 minutes, and purified via HPLC (0.1% TFA/MeCN) to afford LW-RPN13-2 (2.13 mg). MS: m/z $(M+1)^+$: 1020.98.

Example 2. Exemplary RPN13 Degrader WL40

Proteasome inhibition is an effective treatment for multiple myeloma (MM); however, targeting different components of the Ubiquitin-Proteasome-System (UPS) remains elusive. RNA-interference studies described herein identified proteasome-associated ubiquitin-receptor Rpn13 as a mediator of MM cell growth and survival. Here, the exemplary degrader of Rpn13, WL40, was developed using a small-molecule-induced targeted protein degradation strategy to selectively degrade this component of the UPS. WL40 was synthesized by linking the Rpn13 covalent inhibitor RA190 with the Cereblon (CRBN) binding ligand thalidomide. WL40 binds to both Rpn13 and CRBN and triggers degradation of cellular Rpn13, and is therefore beneficial in exploiting a covalent inhibitor for the development of degraders. Biochemical and cellular studies show that WL40-induced Rpn13 degradation is both CRBN E3 ligase- and Rpn13-dependent. Importantly, WL40 decreases viability in MM cell lines and patient MM cells, even those resistant to bortezomib. Mechanistically, WL40 interrupts Rpn13 function and activates caspase apoptotic-cascade, ER stress response- and p53/p21-signaling. In animal model studies, WL40 inhibits xenografted human MM cell growth and prolongs survival. Overall, the data show the development of a UbR Rpn13 degrader with potent anti-MM activity.

Materials and Methods

Chemical Synthesis of WL40

All of the chemical reagents were purchased from Sigma-Aldrich with proper quality control. The compound WL40 was characterized using $^1$H NMR (see FIG. 25A), $^{13}$C NMR (see FIG. 25B), and MS. RA190 and WL40 were synthesized in the Qi laboratory and were characterized using $^1$H NMR, $^{13}$C NMR, and MS.

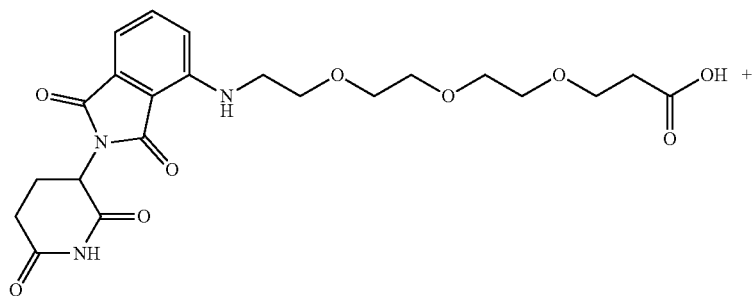

1

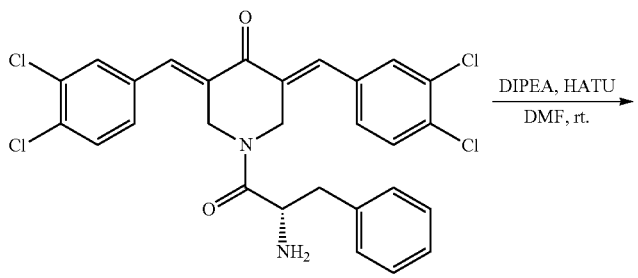

RA190

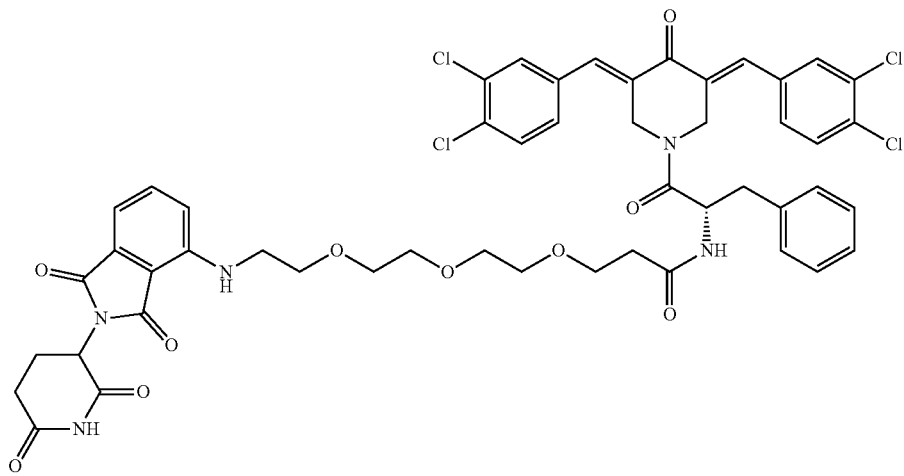 [SMILES: O=C1CCC(N2C(=O)c3cccc(NCCOCCOCCOCCC(=O)N[C@@H](Cc4ccccc4)C(=O)N4C/C(=C\c5ccc(Cl)c(Cl)c5)C(=O)/C(=C/c5ccc(Cl)c(Cl)c5)C4)c3C2=O)C(=O)N1]

Procedure for the Synthesis of Compound WL40

Compound 1 (221 mg, 0.463 mmol, 1 eq.) and HATU (184 mg, 0.467 mmol, 1.01 eq) were added to a 25 mL round-bottom flask. DMF (2 mL) was added to generate a colorless solution, and then DIPEA (400 μL, 5 eq) was added. The resulting mixture was stirred at room temperature for 15 minutes. RA190 (260 mg, 0.463 mmol, 1 eq) was added into the reaction flask, and the reaction was continued with continuous stirring at room temperature for 30 minutes. The reaction mixture was then purified directly via HPLC (0.1% TFA, water/MeCN) to give WL40 as yellow powder. 440 mg, yield: 93.2%.

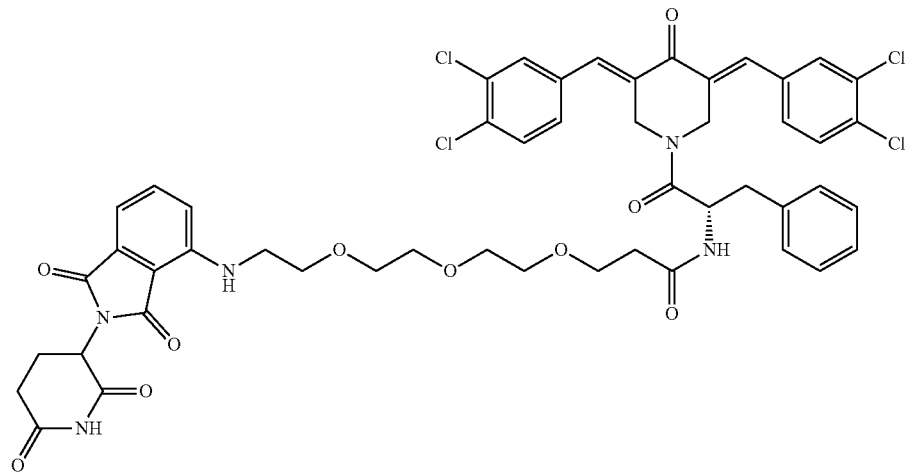

Compound WL40. 440 mg, yield: 93.2%; yellow powder. NMR characterization is shown in FIGS. 25A and 25B. $^1$H NMR (500 MHz, DMSO) δ 11.09 (s, 1H), 8.27 (d, J=8.3 Hz, 1H), 7.87 (d, J=1.6 Hz, 1H), 7.81 (d, J=1.6 Hz, 1H), 7.75 (dd, 7=11.3, 8.4 Hz, 2H), 7.65 (s, 1H), 7.61-7.54 (m, 3H), 7.48 (d, J=8.4 Hz, 1H), 7.14-7.11 (m, 3H), 7.03 (d, J=7.0 Hz, 1H), 6.90 (dd, 7=7.1, 2.3 Hz, 2H), 6.58 (s, 1H), 5.05 (dd, J=12.8, 5.4 Hz, 1H), 4.87-4.67 (m, 5H), 3.59 (t, J=5.4 Hz, 2H), 3.52 (dd, J=5.8, 3.2 Hz, 2H), 3.48 (dd, J=6.1, 3.6 Hz, 9H), 2.87 (ddd, J=17.0, 13.9, 5.4 Hz, 2H), 2.74 (dd, J=13.6, 5.8 Hz, 1H), 2.67-2.52 (m, 4H), 2.17 (t, J=6.6 Hz, 2H), 2.04-1.99 (m, 1H). $^{13}$C NMR (126 MHz, DMSO) δ 185.64, 173.28, 170.53, 170.30, 169.99, 169.39, 167.76, 146.85, 137.61, 136.67, 135.42, 135.08, 134.52, 134.39, 134.23, 133.96, 132.77, 132.61, 132.53, 132.49, 132.13, 131.39, 130.87, 130.71, 129.31, 128.45, 126.85, 117.88, 111.15, 109.69, 70.21, 70.15, 69.89, 69.33, 66.92, 50.16, 49.02, 46.37, 43.13, 42.15, 37.53, 36.01, 31.45, 22.62. MS (EI) calcd. for $C_{50}H_{47}Cl_4N_5O_{10}$: 1019.75, Found: 1020.58.

Procedures for Assays Described Herein

CRBN AlphaScreen

Assays were performed with minimal modifications from the manufacturer's protocol (PerkinElmer, USA). All reagents were diluted in 50 mM HEPES, 150 mM NaCl, 0.1% w/v BSA, 0.01% w/v Tween20, pH 7.5, and allowed to equilibrate to room temperature prior to addition to plates. After addition of Alpha beads to master solutions, all subsequent steps were performed under low light conditions. A 2× solution of components with final concentrations of CRBN-DDB1 at 50 nM, Ni-coated Acceptor Bead at 20 μg/ml, and 15 nM biotinylated-pomalidomide was added in 10 μL to 384-well plates (AlphaPlate-384, PerkinElmer, USA). Plates were spun down at 150×g, and 100 nL of compound in DMSO from stock plates were added by pin transfer using a Janus Workstation (PerkinElmer, USA). The streptavidin-coated donor beads (20 μg/ml final) were added as to the solution in a 2×, 10 μL volume. Following this addition, plates were sealed with foil to prevent light exposure and evaporation. The plates were spun down again at 150 g. Plates were incubated at room temperature for 1 hour, and then read on an Envision 2104 (PerkinElmer, USA), using the manufacturer's protocol.

RPN13 AlphaScreen

Assays were performed with minimal modifications from the manufacturer's protocol (PerkinElmer, USA). All reagents were diluted in 50 mM HEPES, 150 mM NaCl, 0.1% w/v BSA, 0.01% w/v Tween20, pH 7.5, and allowed to equilibrate to room temperature prior to addition to plates. After addition of Alpha beads to master solutions, all subsequent steps were performed under low light conditions. A 2× solution of components with final concentrations of RPN13 at 670 nM, Ni-coated Acceptor Bead at 20 μg/ml, and 5 nM biotinylated-poly-Ub K48-linked chains (UCB-230, BostonBiochem, USA) was added in 10 μL to 384-well plates (AlphaPlate-384, PerkinElmer, USA). Plates were spun down at 150×g, and 100 nL of compound in DMSO from stock plates were added by pin transfer using a Janus Workstation (PerkinElmer, USA). The streptavidin-coated donor beads (20 μg/ml final) were added, as with previous the solution, in a 2×, 10 μL volume. Following this addition, plates were sealed with foil to prevent light exposure and evaporation. The plates were spun down again at 150 g. Plates were incubated at room temperature for 1 hour, and then read on an Envision 2104 (PerkinElmer, USA), using the manufacturer's protocol.

Cell Culture and Reagents

Human MM cell lines MM.1S, MM.1R, RPMI-8226, ANBL6.WT, ANBL6.BR, DOX40, INA6, and normal PBMCs were cultured in RPMI1640 complete medium. Informed consent was obtained from ah patients in accordance with the Helsinki protocol. MM CD138-positive cells, bone marrow stromal cells (BMSCs), and plasmacytoid dendritic cells (pDCs) from MM patients were isolated and cultured as described previously.[32]

Immunoblotting

Cellular protein extracts were prepared using RIPA lysis buffer (50 mM Tris-HCl, 150 mM NaCl, 1% NP-40, 0.5% sodium deoxycholate, and 0.1% SDS). Protein lysates were subjected to immunoblotting using antibodies against poly ADP ribose polymerase (PARP, BD Bioscience Pharmingen, San Diego, Calif.), caspase 3, caspase 8, p53 (Santa Cruz Biotechnology), caspase 9, p-eIF2a (Abeam, Cambridge, Mass.), caspase 7, cyclin B1, CDC25C, $CDCl_2$, p21, Rpn13, PERK, BIP, Calnexin, GFP, LC3A/B, α-tubulin (Cell Signaling, Beverly, Mass.), polyubiquitin (Enzo Life Sciences, Inc., Farmingdale, N.Y.), or β-actin (Sigma-Aldrich, St. Louis, Mo.).

Proteasome Activity Assays

MM.1S cells were treated with WL40 (1 μM or 10 μM) or Bortezomib (1 μM) for 3 hours; cells were then harvested and lysed in lysis buffer, followed by removal of debris by centrifugation. Total protein (25 μg) was analyzed for proteasome activity using 20S proteasome Assay Kit (Calbiochem), as previously described.[33]

Cell Viability and Apoptosis Analysis

Cell viability was determined by WST-1/CellTiter-Glo Luminescent assays, as described previously.[34] Apoptosis was measured using Annexin/PI staining.[33] Caspase activity assay and cell cycle analysis were performed as described previously.[35]

Generation of CRISPR/Cas9-Knockout Cell Lines

CRISPR-Cas9 genome editing was performed to generate Rpn13-knockout (Rpn13-KO) HCT116 and MM.1S cell lines. Cells were transfected with Rpn13-CRISPR/Cas9-knockout (KO) plasmid (Santa Cruz Biotechnology, Inc., Santa Cruz, Calif., USA) using Lipofectamine 2000 (Thermo Fisher Scientific, Waltham, Mass., USA) or the cell line Nucleofector Kit V (Amaxa Biosystems, Cologne, Germany), respectively. After 48 h incubation, green fluorescent protein (GFP)-positive cells were sorted. Rpn13 KO was confirmed by both protein expression studies and DNA sequencing.

Human MM Xenograft Model

Animal model studies were performed as described previously.[32, 33, 36] Briefly, CB17 SCID mice were subcutaneously inoculated with $5.0 \times 10^6$ MM.1S cells. When tumors were measurable (100 mm$^3$) at approximately 3 weeks after MM-cell injection, mice (10 mice/group) were treated on a twice-weekly schedule with vehicle alone, WL40, or RA190. Mice were euthanized when tumor volume reached institutional limit (2000 mm$^3$). All animal experiments protocols were approved by and conformed to the relevant regulatory standards of the Institutional Animal Care and Use Committee at the Dana-Farber Cancer Institute.

Analysis of Mice Tumors

Tumors were harvested from WL40-treated and control animals. Tumor sections were fixed and paraffin embedded for immunostaining to detect growth inhibition (Ki67), apoptosis (cleaved caspase-3), poly-ubiquitination (PolyU), and angiogenesis (CD31), as described previously.[32, 34] Tumor protein lysates from control vehicle- and WL40-treated mice were analyzed for caspase-8, poly-Ubiquitin or β-actin level using immunoblot analyses.

Statistical Analysis

Statistical significance was derived using the two-tailed Student's t test. Survival of mice was analyzed by GraphPad Prism software.

Results and Discussion

Development of Rpn13 Degrader

The main principle underlying the synthetic design of degraders is that bivalent molecules can interact with targeted proteins and E3 ligases simultaneously to induce the ubiquitination of targeted proteins. Therefore, a small-molecule Rpn13 inhibitor, RA190, that covalently binds to Cys88 of the Rpn13 Pru domain, was enlisted. The covalent binding of RA190 to Rpn13 interrupts the recognition of polyubiquitinylated proteins that signals for subsequent degradation by the proteasome. The degradation strategy utilized the E3 ligase, CRBN, and its binding molecules, immunomodulatory drugs (IMiDs), one of which is thalidomide. These IMiDs bind to the E3 ubiquitin ligase complex (CUL4-RBX-DDB1 CRBN/CRL4$^{CRBN}$) and have also been used in the treatment of MM. More specifically, RA190 was linked with thalidomide via either an alkyl linker or a polyethylene glycol (PEG) linker to create a set of potential degraders. Amongst these compounds, WL40, created by linking RA190 to thalidomide with a short PEG linker, showed promising activity (FIG. 19A) as a potent degrader.[37]

Specificity and Functionality of WL40

Several experiments were performed to confirm the specificity of WL40. Firstly, WL40-CRBN binding activity was assessed using in vitro AlphaScreen assays, as previously described.[27] Biochemical CRBN binding analysis confirmed that WL40 interacts with the E3 ubiquitin receptor CRBN using thalidomide and lenalidomide as positive controls (FIG. 19B). As expected, the Rpn13 inhibitor RA190 alone did not show any binding to CRBN (FIG. 19B). It was then examined whether the bivalent molecule, WL40, can bind to Rpn13. A novel biochemical AlphaScreen assay was designed to measure compound binding to Rpn13 (FIG. 19C). Since Rpn13 recognizes polyubiquitin (polyUb), the GST-tagged Rpn13 and biotinylated polyUb are immobilized on the acceptor and donor beads of the AlphaScreen assay (obtained from PerkinElmer). Upon excitation, the donor bead releases a singlet of oxygen, which reaches the acceptor bead and creates an emission. The binding of RA190 and WL40 interrupts this recognition event and eliminates the signal. Using RA190 as a positive control, it was further confirmed that WL40 binds to Rpn13 and interrupts Rpn13's recognition of the biotinylated polyubiquitin tail. (FIG. 19D). Thus, it was confirmed that WL40 can bind both Rpn13 and CRBN complex.

Next, it was examined whether WL40 decreases cellular Rpn13 levels in MM cells. MM.1S cells were treated with various concentrations of WL40 (20 0 nM, 400 nM, or 800 nM) for 4 hours, 8 hours, and 16 hours; protein lysates were then analyzed for Rpn13 levels using immunoblot analysis. A marked decrease in Rpn13 levels was noted in WL40-treated cells in a time-dependent manner (FIG. 19E, upper panel). Decrease in Rpn13 levels was detectable as early as 8 hours after WL40 treatment and maximally (95%) reduced at 16 hours. Rpn13 protein level reduction was not observed with RA190 treatment (FIG. 19E, lower panel). There was no change in protein levels of tubulin, used as a loading control (FIG. 19E). To further corroborate the findings, MM.1S cells were treated with WL40, and then analyzed intracellular alterations in Rpn13 using flow cytometry. In concert with the data obtained using immunoblot analysis, a significant reduction in Rpn13 expression was noted in WL40-versus DMSO-, or RA190-treated cells (FIG. 19E).

To confirm that CRBN presence is a prerequisite for the function of WL40 in cells, CRBN-knockout (KO) MM.1S cells[27, 38] were utilized, and the effect of WL40 on Rpn13 degradation was examined. As shown in FIG. 19G, no decrease in Rpn13 levels was observed in WL40-versus DMSO control-treated CRBN-KO cells. These data demonstrate that WL40 degrades Rpn13 in a CRBN-dependent manner (FIG. 19G). Next, a Green Fluorescent Protein (GFP)u-1 reporter cell line expressing Ub-tagged GFP, which is marked for constitutive degradation by the proteasome, was utilized. GFPu-1 cells were treated with WL40, and GFP levels were then analyzed using immunoblotting. As shown in FIG. 19H, WL40 treatment increases GFP levels, indicating the blockade of proteasome-mediated GFP degradation. Similar results were observed in RA190-treated cells. These findings provide evidence for the requirement of Rpn13 engagement by WL40 for its activity. Thus, a novel degrader has been developed that can engage with both RPN13 and Cereblon (CRBN) simultaneously and induce targeted protein degradation.

To eliminate the potential impact of WL40 on proteasome function, the effect of WL40 on proteasome activities was assessed. Examination of both cellular extracts from WL-40-treated MM cells and purified recombinant 20S proteasome showed that WL40 does not inhibit 20S proteasomal activities (chymotrypsin-like, trypsin-like, or caspase-like activities) (FIGS. 20A and 20B). Pretreatment of MM.1S cells with the proteasome inhibitor, MG132, blocked WL40-mediated Rpn13 degradation, suggesting that Rpn13 degradation occurs through the proteasome and that proteasome function is required for WL40-induced RPN13 degradation, consistent with other reports of targeted protein degradation (FIG. 20C). Together, these biochemical and cellular findings demonstrate that WL40 binds to CRBN and Rpn13 within cells and promotes ubiquitination of Rpn13, followed by subsequent proteasomal degradation of Rpn13.

Next, the effect of WL40 on additional MM cell lines, including p53-mutated RPMI-8226 cells or bortezomib-resistant ANBL6.BR cells, was evaluated. WL40 (400 nM) treatment induced RPN13 degradation in both cell lines (FIGS. 20D and 20E). It was also examined whether WL40 triggers the accumulation of polyubiquitinated (PolyUb) protein, a hallmark event during proteasome inhibition, in these cell lines[39, 40] MM.1S and ANBL6.BR cells were treated with WL40, followed by analysis of ubiquitinated protein using immunoblotting. A marked increase in PolyUb proteins was detected in WL40-versus DMSO-treated cells (FIG. 20F). PolyUb increase was also observed in bortezomib- and RA190-treated cells, albeit to a lesser extent than observed in WL40-exposed cells (FIG. 20F). The finding that WL40 triggered a more rapid and higher molecular weight PolyUb versus bortezomib suggests a distinct mechanism of action (MOA) for these agents. Indeed, bortezomib only targets the 20S proteasomal activities and therefore leads to aggregation of lower molecular weight PolyUb proteins; whereas WL40 blocks the 19S proteasome and prevents deubiquitination of substrates, thereby resulting in higher molecular weight PolyUb proteins. Taken together, these data demonstrate that WL40 blocks proteasome-mediated protein degradation upstream of the 20S proteasome and promotes RPN13 degradation selectively, without inhibiting proteasomal activities.

Anti-MM Activity of WL40

In order to examine whether WL40-triggered Rpn13 degradation affects the viability of MM cells, a panel of MM cell lines sensitive or resistant to conventional (dexamethasone, alkylating agents, anthracyclines) or novel (bortezomib) therapies, including lines representing cytogenetically-distinct MM subtypes, was utilized. WL40 is more cytotoxic than the parental Rpn13 inhibitor RA190 against dexamethasone-sensitive MM.1S and resistant MM.1R isogenic MM cell lines (FIG. 21A), indicating potent anti-MM activity of WL40 versus RA190 due to its ability to degrade Rpn13. $IC_{50}$ values for both MM.1S and MM.1R cells correlate with the $DC_{50}$ for Rpn13. Importantly, WL40 overcomes bortezomib-resistance, evidenced by similar $IC_{50}$ values for both bortezomib-sensitive (ANBL6.WT) and -resistant (ANBL6.BR) cells (FIG. 21A, Table). In addition, cytotoxic activity of WL40 was observed even against p53-mutated RPMI-8226 cells and MM growth factor IL-6-dependent INA6 MM cells (FIG. 21A, Table). These data suggest that WL40 can overcome p53-mutation, a high-risk feature conferring drug resistance in MM, and triggers MM cell death even in the presence of pro-growth and -survival factor IL-6.

To further evaluate the clinical potential of the novel degrader, the effect of WL40 in MM patient cells was examined next. First, primary tumor (CD138+) cells from newly diagnosed (patient #4) and MM refractory to bortezomib/lenalidomide (patient #2-4) were analyzed (FIG. 21B). Treatment with WL40 decreased viability of all CD138+ patient cells ($IC_{50}$ range: 95 nM-170 nM) (FIG. 21B). Importantly, WL40 at the $IC_{50}$ for MM cells does not affect viability of normal PBMCs (FIG. 21C), suggesting a favorable therapeutic index.

Adhesion of MM cells to bone marrow stromal cells (BMSCs) induces MM-promoting growth factors and protects against cytotoxic activity of anti-MM drugs.[42, 43] Moreover, BM accessory cells such as plasmacytoid dendritic cells (pDCs), can also trigger MM cell proliferation, survival, and drug-resistance.[32] Therefore, the effect of WL40 was assessed next using the patient MM-BMSCs or MM-pDCs in vitro co-culture assays. Even in these co-cultures with BMSCs or pDCs, WL40 induced a dose-dependent decrease in the viability of MM cells. (FIGS. 21D and 21E). These data demonstrate that WL40 retains its anti-MM activity in the tumor-protective MM-host BM microenvironment.

Rpn13 Degradation-Induced Signal Transduction

Next, the downstream signaling triggered by WL40 during Rpn13 degradation was examined. WL40 treatment induces an increase in early- (Annexin V$^+$/PI$^-$) and late-stage (Annexin V$^+$/PI$^+$) apoptosis, associated with proteolytic cleavage of Poly (ADP) ribose polymerase (PARP) by immunoblotting, as well as activation of caspase-3, caspase-7, caspase-8 and caspase-9, assessed in caspase enzymatic activity assays (FIG. 22A and FIG. 22B, and FIG. 22C, respectively). Additionally, treatment of MM.1S and ANBL6.BR cells with WL40 triggers a reduction in the levels of cell-cycle regulatory proteins (cyclin-B1, CDC25C, and $CDCl_2$), indicating growth arrest in these cells (FIG. 22D). Examination of the p53/p21 apoptotic signaling axis showed an earlier induction of this pathway in WL40-versus Rpn13 inhibitor RA190-treated ANBL6.BR cells (FIG. 22E).

Elevated endoplasmic reticulum (ER)-associated protein degradation (ERAD) signaling is a hallmark of MM, which confers enhanced sensitivity to proteasome inhibitors. Since WL40, like botezomib, triggers PolyUb accumulation (FIG. 20F), it was next examined whether it increases ER stress and triggers associated unfolded protein response (UPR) signaling. Indeed, a rapid and robust induction of UPR proteins (BIP, PERK, phosphorylated eIF2α, or a lectin protein calnexin) was found in WL40-treated ANBL6.BR and MM.1S cells (FIG. 22E and FIG. 22F, respectively). Of note, Rpn13 inhibitor RA190 also triggered UPR signaling, but with delayed kinetics and to a lesser extent than Rpn13 degrader WL40. Prior studies have established that ER stress also induces an alternative lysosomal pathway (autophagy) for degradation of misfolded proteins.[40] Here, it was found that WL40 induces PERK, a key component in autophagic signaling. To further confirm the activation of autophagy by WL40, alterations in the autophagic molecule LC3/Atg8 were examined. During autophagy, LC3/Atg8 is processed and attached to the autophagosome membrane by conjugation with phosphatidylethanolamine. Immunoblot analysis showed a significant increase in LC3A/B in WL40-versus DMSO-treated ANBL6.BR or MM.1S cells (FIG. 22E and FIG. 22F, respectively). As for UPR signaling in ANBL6.BR cells, a more pronounced LC3 activation was noted after WL40 than RA190 treatment. Overall, these findings show that WL40-induced apoptosis is associated with activation of the caspase-cascade, p53/p21 signaling, ER stress response signaling, and autophagy. Importantly, it is shown that degradation of Rpn13 triggers more pronounced biologic sequelae in MM cells than domain-specific Rpn13 inhibition.

In Vivo Anti-MM Activity of WL40

To fully understand the therapeutic potential of the RPN13 degrader, the in vivo efficacy of WL40 was evaluated using the human plasmacytoma xenograft mouse model.[3, 34] This model has been useful in validating novel anti-MM therapies bortezomib, carfilzomib, ixazomib, lenalidomide, and pomalidomide, which have translated to clinical trials and FDA approval. Treatment of MM.1S-bearing mice with intraperitoneal (IP) injections of WL40 (14.7 µM/kg) inhibits MM growth and prolongs host survival (FIG. 23A). Rpn13 inhibitor RA190 (26.8 µM/kg) also attenuates MM tumor progression and extends mice survival (FIGS. 23A and 23B, respectively). Importantly, use of even half the equimolar dose of WL40 versus RA190 achieves similar extent of tumor growth inhibition and host survival. These findings suggest that Rpn13 degradation could be a more potent strategy in blocking tumor progression than Rpn13 inhibition. WL40 was well tolerated, with no significant weight loss in WL40-treated mice (data not shown). Analysis of tumors harvested from treated mice showed that WL40 induced increased accumulation of PolyUb proteins relative to tumors from control mice (FIGS. 23C and 23D). WL40 decreases proliferation, induces apoptosis, and blocks angiogenesis in harvested tumors, as assessed by Ki67, cleaved caspase-3, and CD31 staining, respectively (FIG. 23D). These data therefore show more potent in vivo anti-MM activity of exemplary compound WL40 versus RA190.

In summary, the development of a small-molecule degrader, WL40, targeting UbR Rpn13 is described herein, and its specificity and functionality is validated using both biochemical and genetic models. Importantly, the studies using both in vitro and in vivo preclinical models of MM show potent anti-MM activity of WL40. Novel findings include: 1) the development of the covalent inhibitor-based heterobifunctional degrader molecule of Rpn13 is demonstrated; 2) using both pharmacological assays and in vivo tumor efficacy models, it is shown that the Rpn13 degrader is cell permeable and triggers potent anti-MM activity, even in the presence of cytoprotective tumor BM microenvironment, overcomes bortezomib-resistance, and is active even in the context of mutated-p53; 3) Rpn13 degradation is a more efficient inducer of MM cell death than Rpn13 inhibition, evidenced by a more rapid and robust induction of ER stress response/UPR- and p53/p21 apoptotic signaling by WL40 than RA190; 4) the MM xenograft model study showed that significant tumor growth inhibition can be achieved using half the equimolar dose of WL40 versus Rpn13 inhibitor RA190; and 5) the study strongly suggests that degradation of tumor-promoting proteins within the UPS using the degronimid strategy is a plausible therapeutic approach, especially in cancers with elevated ER stress/UPR signaling such as MM.

Finally, the anti-MM activity of the IMiD, lenalidomide, occurs via CRBN complex-mediated degradation of Ikaros proteins, IKZF1 and IKZF3.[38] This finding supports the therapeutic potential of strategies to induce degradation of tumorigenic target proteins via chemically synthesized small-molecule degraders. Importantly, extensive preclinical research shows that degraders may: reduce the need to maintain high systemic inhibitor levels for target inhibition and efficacy in vivo; neutralize even high levels of target protein expression and function; as well as degrade substrates and thereby avoid resistance mechanisms such as gene mutation or copy number alterations. Overall, provided herein is an exemplary rationale for the development of UPS-based degrader therapies, which further indicates the potential clinical utility of novel therapeutics targeting UbR Rpn13 to improve patient outcome in MM.

REFERENCES

1. Kane R C, Bross P F, Farrell A T, Pazdur R. Velcade: U. S. FDA approval for the treatment of multiple myeloma progressing on prior therapy. *Oncologist* 2003; 8(6): 508-513.
2. Richardson P G, Barlogie B, Berenson J, Singhal S, Jagannath S, Irwin D, et al. A phase 2 study of bortezomib in relapsed, refractory myeloma. *The New England journal of medicine* 2003 Jun. 26; 348(26): 2609-2617.
3. Anderson K C. Therapeutic advances in relapsed or refractory multiple myeloma. *Journal of the National Comprehensive Cancer Network: JNCCN* 2013 May; 11(5 Suppl): 676-679.
4. Richardson P G, Zweegman S, O'Donnell E K, Laubach J P, Raje N, Voorhees P, el a1. Ixazomib for the treatment of multiple myeloma. *Expert Opin Pharmacother* 2018 December; 19(17): 1949-1968.
5. Lonial S, Waller E K, Richardson P G, Jagannath S, Orlowski R Z, Giver C R, et al. Risk factors and kinetics of thrombocytopenia associated with bortezomib for relapsed, refractory multiple myeloma. *Blood* 2005 Dec. 1; 106(12): 3777-3784.
6. Adams J. The proteasome: a suitable antineoplastic target. *Nature reviews Cancer* 2004 May; 4(5): 349-360.
7. Goldberg A L. Protein degradation and protection against misfolded or damaged proteins. *Nature* 2003 Dec. 18; 426(6968): 895-899.
8. Hershko A. The ubiquitin system for protein degradation and some of its roles in the control of the cell division cycle. *Cell Death Differ* 2005 September; 12(9): 1191-1197.
9. Chauhan D, Hideshima T, Anderson K C. Proteasome inhibition in multiple myeloma: therapeutic implication. *Annu Rev Pharmacol Toxicol* 2005; 45: 465-476.
10. Song Y, Ray A, Li S, Das D S, Tai Y T, Carrasco R D, et al. Targeting proteasome ubiquitin receptor Rpn13 in multiple myeloma. *Leukemia* 2016 September; 30(9): 1877-1886.
11. Anchoori R K, Karanam B, Peng S, Wang J W, Jiang R, Tanno T, et al. A bis-benzylidine piperidone targeting proteasome ubiquitin receptor RPN13/ADRM1 as a therapy for cancer. *Cancer cell* 2013 Dec. 9; 24(6): 791-805.
12. Chen W, Hu X T, Shi Q L, Zhang F B, He C. Knockdown of the novel proteasome subunit Adrm1 located on the 20q13 amplicon inhibits colorectal cancer cell migration, survival and tumorigenicity. *Oncology reports* 2009 February; 21(2): 531-537.
13. Trader D J, Simanski S, Kodadek T. A reversible and highly selective inhibitor of the proteasomal ubiquitin receptor rpn13 is toxic to multiple myeloma cells. *J Am Chem Soc* 2015 May 20; 137(19): 6312-6319.
14. Fejzo M S, Dering J, Ginther C, Anderson L, Ramos L, Walsh C, et al. Comprehensive analysis of 20q13 genes in ovarian cancer identifies ADRM1 as amplification target. *Genes, chromosomes &cancer* 2008 October; 47(10): 873-883.
15. Husnjak K, Dikic I. Ubiquitin-binding proteins: decoders of ubiquitin-mediated cellular functions. *Annual review of biochemistry* 2012; 81: 291-322.

16. Schreiner P, Chen X, Husnjak K, Randles L, Zhang N, Elsasser S, et al. Ubiquitin docking at the proteasome through a novel pleckstrin-homology domain interaction. *Nature* 2008 May 22; 453(7194): 548-552.
17. Lu X, Nowicka U, Sridharan V, Liu F, Randles L, Hymel D, et al. Structure of the Rpn13-Rpn2 complex provides insights for Rpn13 and Uch37 as anticancer targets. *Nature communications* 2017 Jun. 9; 8: 15540.
18. Fejzo M S, Anderson L, Chen H W, Anghel A, Zhuo J, Anchoori R, et al. ADRM1-amplified metastasis gene in gastric cancer. *Genes, chromosomes & cancer* 2015 August; 54(8): 506-515.
19. Carvalho B, Postma C, Mongera S, Hopmans E, Diskin S, van de Wiel M A, et al. Multiple putative oncogenes at the chromosome 20q amplicon contribute to colorectal adenoma to carcinoma progression. *Gut* 2009 January; 58(1): 79-89.
20. Chen X, Walters K J. Structural plasticity allows UCH37 to be primed by RPN13 or locked down by INO80G. *Molecular cell* 2015 Mar. 5; 57(5): 767-768.
21. Anchoori R K, Jiang R, Peng S, Soong R S, Algethami A, Rudek M A, et al. Covalent Rpn13-Binding Inhibitors for the Treatment of Ovarian Cancer. *ACS Omega* 2018 Sep. 30; 3(9): 11917-11929.
22. Cromm P M, Crews C M. Targeted Protein Degradation: from Chemical Biology to Drug Discovery. *Cell Chem Biol* 2017 Sep. 21; 24(9): 1181-1190.
23. Burslem G M, Smith B E, Lai A C, Jaime-Figueroa S, McQuaid D C, Bondeson D P, et al. The Advantages of Targeted Protein Degradation Over Inhibition: An RTK Case Study. *Cell Chem Biol* 2018 Jan. 18; 25(1): 67-77 e63.
24. Gustafson J L, Neklesa T K, Cox C S, Roth A G, Buckley D L, Tae H S, et al. Small-Molecule-Mediated Degradation of the Androgen Receptor through Hydrophobic Tagging. *Angew Chem Int Ed Engl* 2015 Aug. 10; 54(33): 9659-9662.
25. Lu J, Qian Y, Altieri M, Dong H, Wang J, Raina K, et al. Hijacking the E3 Ubiquitin Ligase Cereblon to Efficiently Target BRD4. *Chem Biol* 2015 Jun. 18; 22(6): 755-763.
26. Sakamoto K M, Kim K B, Kumagai A, Mercurio F, Crews C M, Deshaies R J. Protacs: chimeric molecules that target proteins to the Skp1-Cullin-F box complex for ubiquitination and degradation. *Proceedings of the National Academy of Sciences of the United States of America* 2001 Jul. 17; 98(15): 8554-8559.
27. Winter G E, Buckley D L, Paulk J, Roberts J M, Souza A, Dhe-Paganon S, et al. DRUG DEVELOPMENT. Phthalimide conjugation as a strategy for in vivo target protein degradation. *Science* 2015 Jun. 19; 348(6241): 1376-1381.
28. Fischer E S, Park E, Eck M J, Thoma N H. SPLINTS: small-molecule protein ligand interface stabilizers. *Curr Opin Struct Biol* 2016 April; 37: 115-122.
29. Raina K, Crews C M. Targeted protein knockdown using small molecule degraders. *Curr Opin Chem Biol* 2017 August; 39: 46-53.
30. Toure M, Crews C M. Small-Molecule PROTACS: New Approaches to Protein Degradation. *Angew Chem Int Ed Engl* 2016 Feb. 5; 55(6): 1966-1973.
31. Nowak R P, DeAngelo S L, Buckley D, He Z, Donovan K A, An J, et al. Plasticity in binding confers selectivity in ligand-induced protein degradation. *Nature chemical biology* 2018 July; 14(7): 706-714.
32. Chauhan D, Singh A V, Brahmandam M, Carrasco R, Bandi M, Hideshima T, et al. Functional interaction of plasmacytoid dendritic cells with multiple myeloma cells: a therapeutic target. *Cancer cell* 2009 Oct. 6; 16(4): 309-323.
33. Chauhan D, Catley L, Li G, Podar K, Hideshima T, Velankar M, et al. A novel orally active proteasome inhibitor induces apoptosis in multiple myeloma cells with mechanisms distinct from Bortezomib. *Cancer cell* 2005 November; 8(5): 407-419.
34. Chauhan D, Tian Z, Nicholson B, Kumar K G, Zhou B, Carrasco R, et al. A small molecule inhibitor of ubiquitin-specific protease-7 induces apoptosis in multiple myeloma cells and overcomes bortezomib resistance. *Cancer cell* 2012 Sep. 11; 22(3): 345-358.
35. Chauhan D, Ray A, Viktorsson K, Spira J, Paba-Prada C, Munshi N, et al. In vitro and in vivo antitumor activity of a novel alkylating agent, melphalan-flufenamide, against multiple myeloma cells. *Clin Cancer Res* 2013 Jun. 1; 19(11): 3019-3031.
36. Tian Z, Zhao J J, Tai Y T, Amin S B, Hu Y, Berger A J, et al. Investigational agent MLN9708/2238 targets tumor-suppressor miR33b in MM cells. *Blood* 2012 Nov. 8; 120(19): 3958-3967.
37. Ito T, Ando H, Suzuki T, Ogura T, Hotta K, Imamura Y, et al. Identification of a primary target of thalidomide teratogenicity. *Science* 2010 Mar. 12; 327(5971): 1345-1350.
38. Lu G, Middleton R E, Sun H, Naniong M, Ott C J, Mitsiades C S, et al. The myeloma drug lenalidomide promotes the cereblon-dependent destruction of Ikaros proteins. *Science* 2014 Jan. 17; 343(6168): 305-309.
39. Menendez-Benito V, Verhoef L G, Masucci M G, Dantuma N P. Endoplasmic reticulum stress compromises the ubiquitin-proteasome system. *Hum Mol Genet* 2005 Oct. 1; 14(19): 2787-2799.
40. Bravo R, Parra V, Gatica D, Rodriguez A E, Torrealba N, Paredes F, el al. Endoplasmic reticulum and the unfolded protein response: dynamics and metabolic integration. *Int Rev Cell Mol Biol* 2013; 301: 215-290.
41. Powell C E, Gao Y, Tan L, Donovan K A, Nowak R P, Loehr A, et al. Chemically Induced Degradation of Anaplastic Lymphoma Kinase (ALK). *Journal of medicinal chemistry* 2018 May 10; 61(9): 4249-4255.
42. Chauhan D, Hideshima T, Mitsiades C, Richardson P, Anderson K C. Proteasome inhibitor therapy in multiple myeloma. *Molecular cancer therapeutics* 2005 April; 4(4): 686-692.
43. Chauhan D, Uchiyama H, Akbarali Y, Urashima M, Yamamoto K, Libermann T A, et al. Multiple myeloma cell adhesion-induced interleukin-6 expression in bone marrow stromal cells involves activation of NF-kappa B. *Blood* 1996; 87(3): 1104-1112.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I) or Formula (I'):

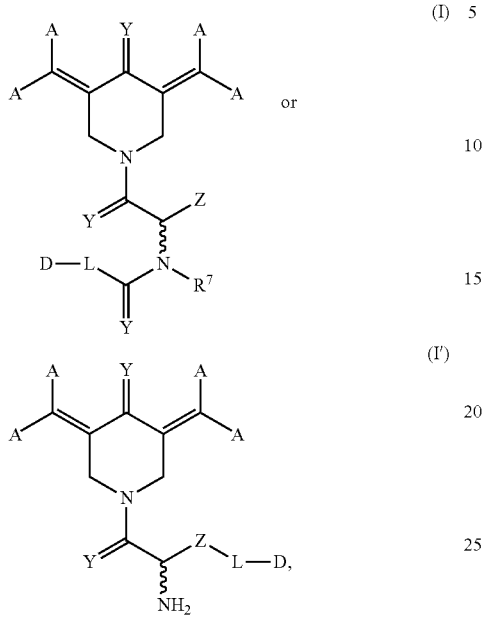

or a pharmaceutically acceptable salt, solvate, hydrate, tautomer, or stereoisomer thereof,
wherein:
  in each pair of A's, one A is hydrogen, and the other A is one of:
  (i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (iii) a 5-or 6-membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and
  (iv) an 8- to 10-membered bicyclic heteroaryl group containing 1-3 heteroatoms selected from the group consisting of O, N, and S; and the second ring is fused to the first ring using 2 carbon atoms, and the bicyclic heteroaryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  wherein Y is selected from the group consisting of O, S, $NR^1$ and $CR^1R^2$, and
  wherein $R^1$ and $R^2$ are selected from the group consisting of hydrogen, nitro, hydroxyl, carboxy, amino, halogen, cyano and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano;
  wherein $R^7$ is hydrogen, $C_{1-6}$ alkyl, or a nitrogen protecting group;
  wherein Z is selected from the group consisting of hydrogen; $C_1$ to $C_{14}$ linear, branched, or cyclic alkyl; phenyl; benzyl, 1-5 substituted benzyl, $C_1$ to $C_3$ alkyl-phenyl, wherein the alkyl moiety is optionally substituted with halogen up to perhalo; $C_1$ to $C_{14}$ linear or branched alkyl, wherein the alkyl moiety is optionally substituted with halogen up to perhalo; —$(CH_2)_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, and wherein the variable q is an integer ranging from 0 to 4, provided that when the compound is of Formula (I'), Z is not hydrogen, and provided that when A is substituted with $S(O)_qR^1$, q is an integer ranging from 0 to 2;
  L is a linker; and
  D is an E3 ubiquitin ligase binding moiety,
wherein D is of the formula IA or IB:

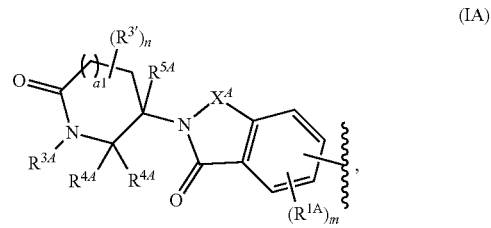

wherein:
  $X^A$ is C(O) or $C(R^{3A})_2$;
  each $R^{1A}$ is independently halogen, OH, $C_1$-$C_6$ alkyl, or $C_1$-$C_6$ alkoxy;
  each $R^{3A}$ is independently H or $C_1$-$C_3$ alkyl;
  each $R^{3'}$ is independently $C_1$-$C_3$ alkyl;
  each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
  $R^{5A}$ is H, $C_1$-$C_3$ alkyl, or halogen;
  m is 0, 1, 2 or 3;
  n is 0, 1, or 2; and
  a1 is 0 or 1; or

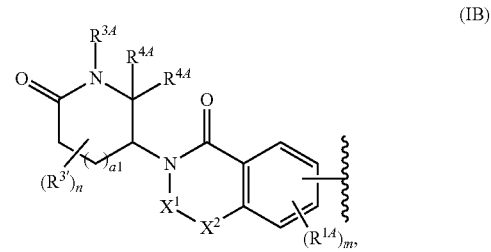

wherein:
—X$^1$—X$^2$— is C(R$^{3A}$)=N or C(R$_{3A}$)$_2$—C(R$^{3A}$)$_2$;
each R$^{1A}$ is independently halogen, OH, C$_1$-C$_6$ alkyl, or C$_1$-C$_6$ alkoxy;
R$^{3A}$ is H or C$_1$-C$_3$ alkyl;
each R$^{3'}$ is independently C$_1$-C$_3$ alkyl;
each R$^{4A}$ is independently H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O;
R$^{5A}$ is H, C$_1$-C$_3$ alkyl, or halogen;
m is 0, 1, 2, or 3;
n is 0, 1, or 2; and
a1 is 0 or 1.

2. The compound of claim 1, wherein D is of the formula:

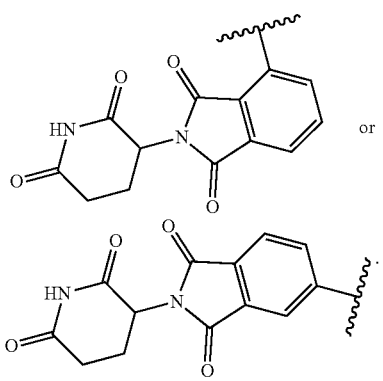 or

3. The compound of claim 1, wherein D is of the formula:

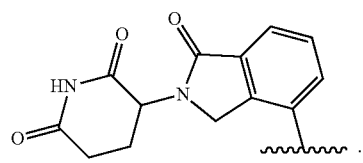 [SMILES: *c1cccc2c1CN(C1CCC(=O)NC1=O)C2=O].

4. The compound of claim 1, wherein the compound is of formula:

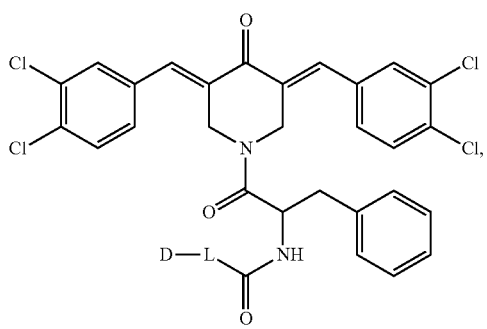

or a pharmaceutically acceptable salt thereof.

5. The compound of claim 1, wherein the compound is of formula:

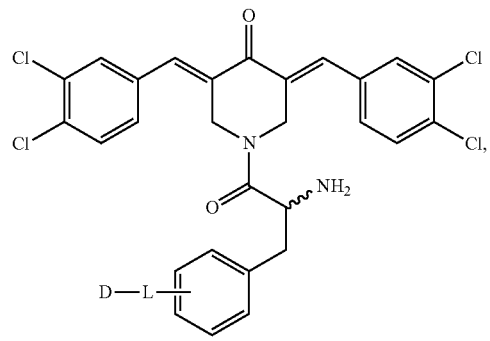

or a pharmaceutically acceptable salt thereof.

6. The compound of claim 1, or a pharmaceutically acceptable salt, solvate, hydrate, tautomer, or stereoisomer thereof, wherein L is a bond, a substituted or unsubstituted C$_{1-12}$ hydrocarbon chain, optionally wherein one or more chain atoms of the hydrocarbon chain are independently replaced with —C(=O)—, —O, S, NR$^b$, N=, or =N—, substituted or unsubstituted carbocyclylene, substituted or unsubstituted heterocyclylene, substituted or unsubstituted arylene, substituted or unsubstituted heteroarylene, or substituted or unsubstituted heteroalkylene, wherein
each instance of R$^b$ is independently hydrogen, substituted or unsubstituted C$_{1-6}$ alkyl, or a nitrogen protecting group, or optionally two instances of R$^b$ are taken together with their intervening atoms to form a substituted or unsubstituted heterocyclic or substituted or unsubstituted heteroaryl ring.

7. The compound of claim 1, wherein in each pair of A's, one A is hydrogen and the other A is phenyl optionally substituted with R$^1$.

8. The compound of claim 7, wherein in each pair of A's, one A is hydrogen and the other A is phenyl substituted with halogen.

9. The compound of claim 1, wherein both instances of Y are O.

10. The compound of claim 1, wherein one instance of Y is O and the other instance of Y is —CH$_2$.

11. The compound of claim 1, wherein Z is benzyl.

12. The compound of claim 6, wherein L is an unsubstituted C$_{1-12}$ hydrocarbon chain, optionally wherein one or more chain atoms of the hydrocarbon chain are independently replaced with —C(=O)—, —O—, or —NR$^b$—.

13. The compound of claim 1, wherein L is of the formula:

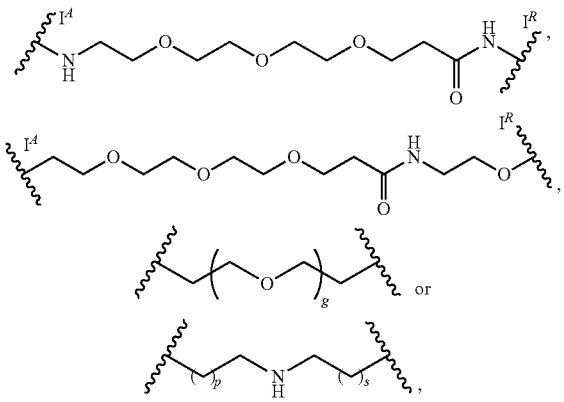

wherein:
g is 1-5;
p is 2-5; and
s is 1-5;
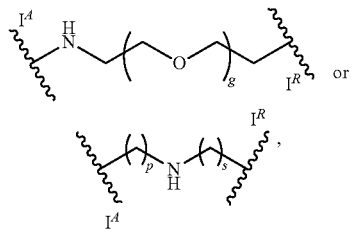
wherein:
g is 2, 3, or 4;
p is 0, 1, 2, 3, 4, or 5; and
s is 1, 2, 3, 4, 5, or 6;
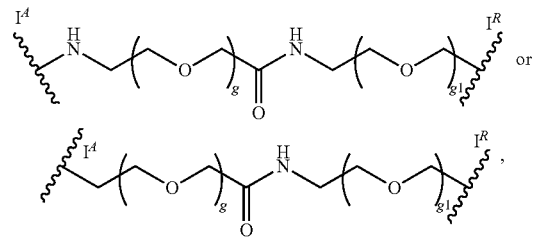
wherein:
g is 1-5; and
g1 is 1-5;
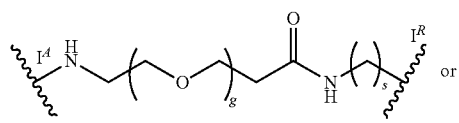
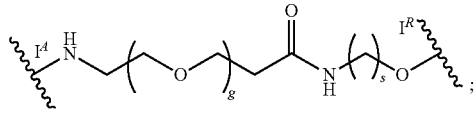
wherein:
g is 1-5; and
s is 2-4: or
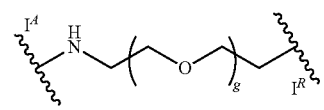
wherein:
g is 2, 3, or 4;
wherein $I^A$ indicates the point of attachment to D, and $I^R$ indicates the point of attachment to
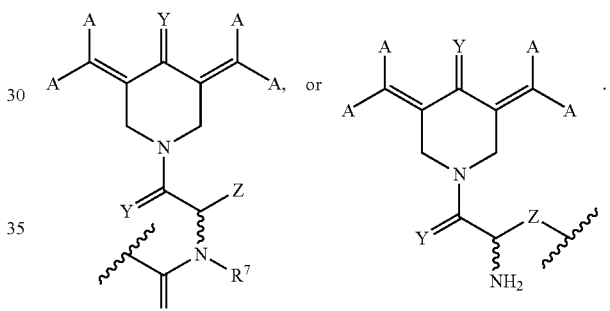
14. The compound of claim 1, wherein:
L is of the formula:
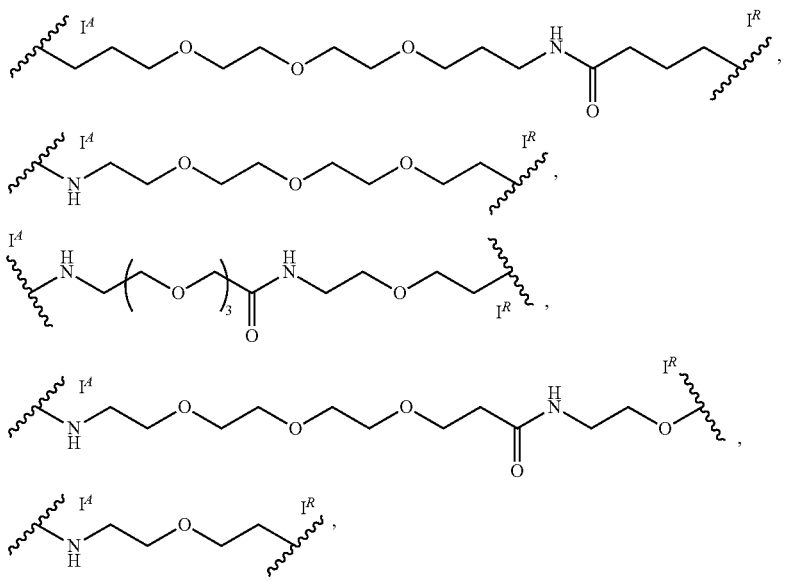

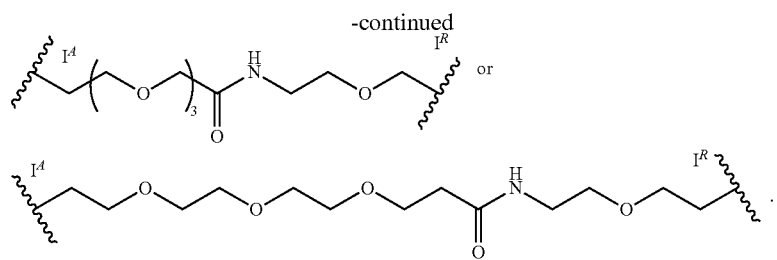
wherein $I^A$ indicates the point of attachment to D, and $I^R$ indicates the point of attachment to
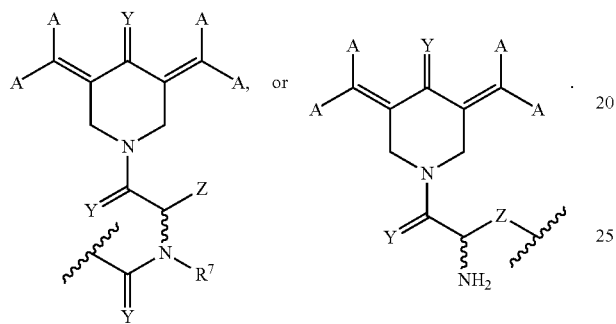
15. The compound of claim 1, wherein the compound is of the formula:
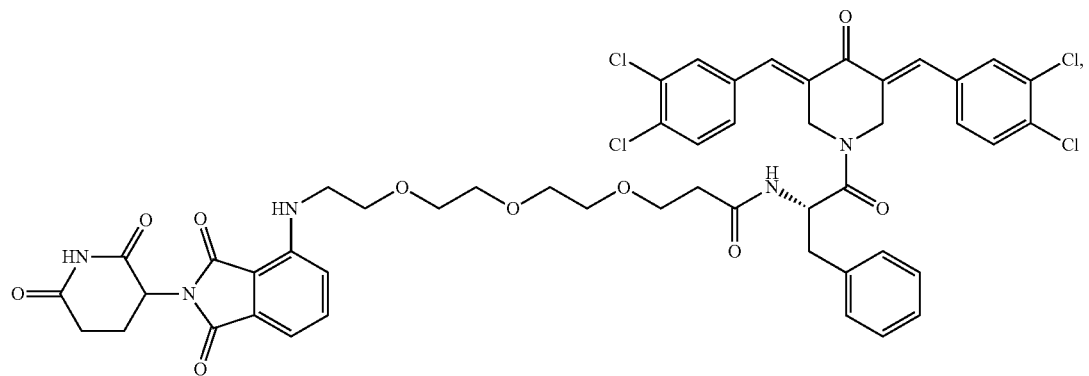
(LW-RPN13-1; WL-40)
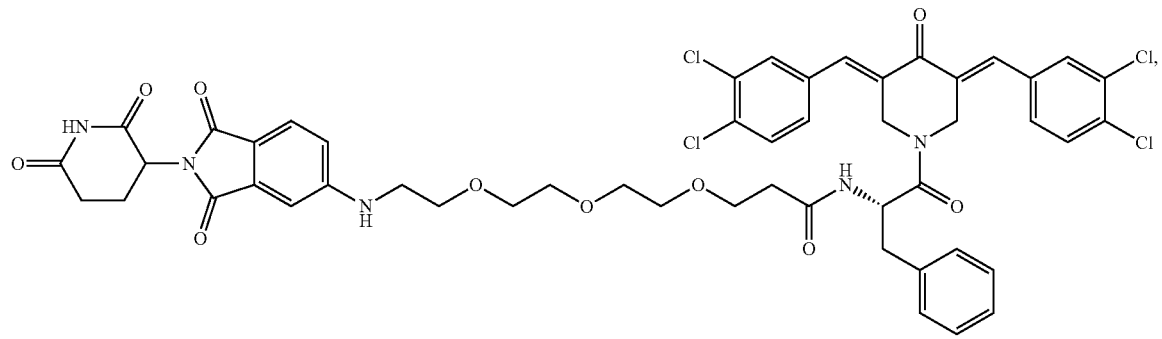
(LW-RPN13-2)

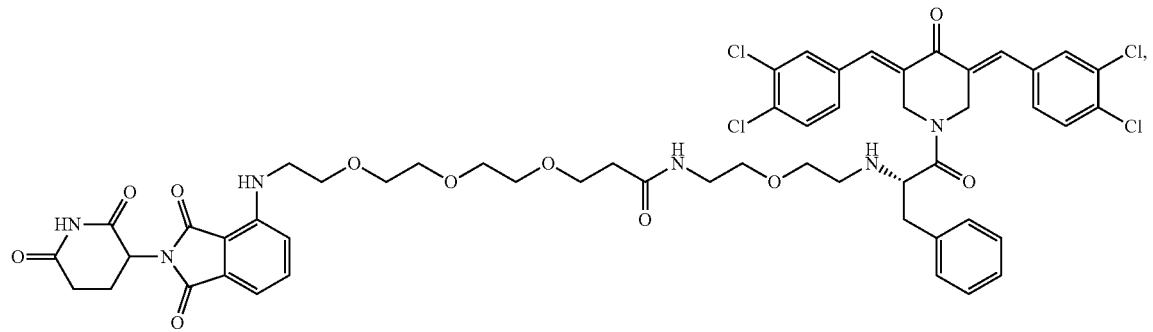
(dRPN13-3)
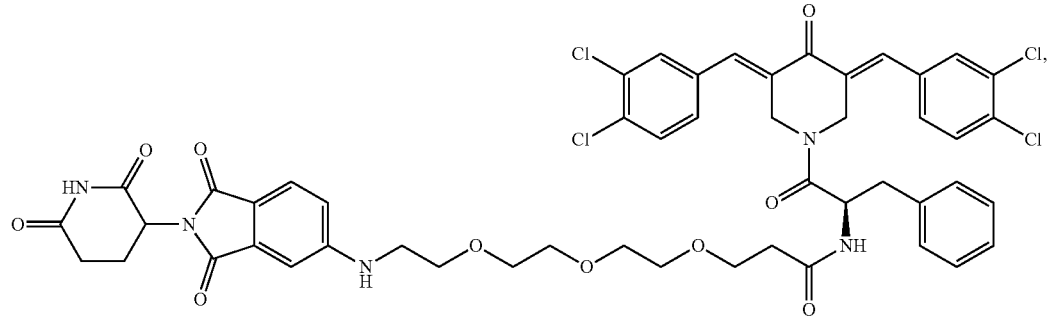
(WL44)
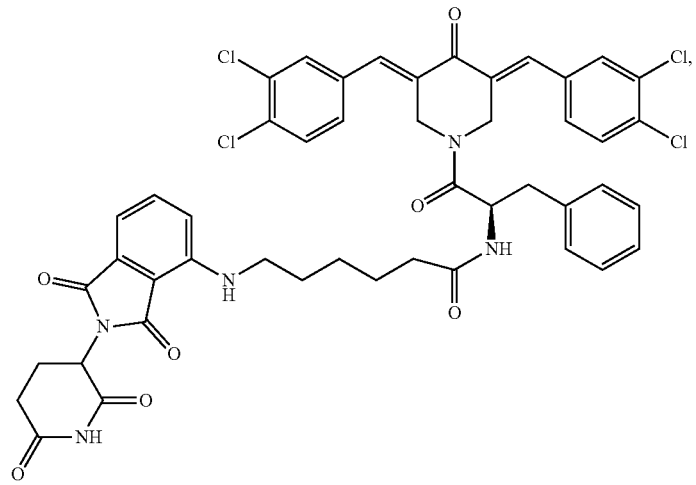
JQRA
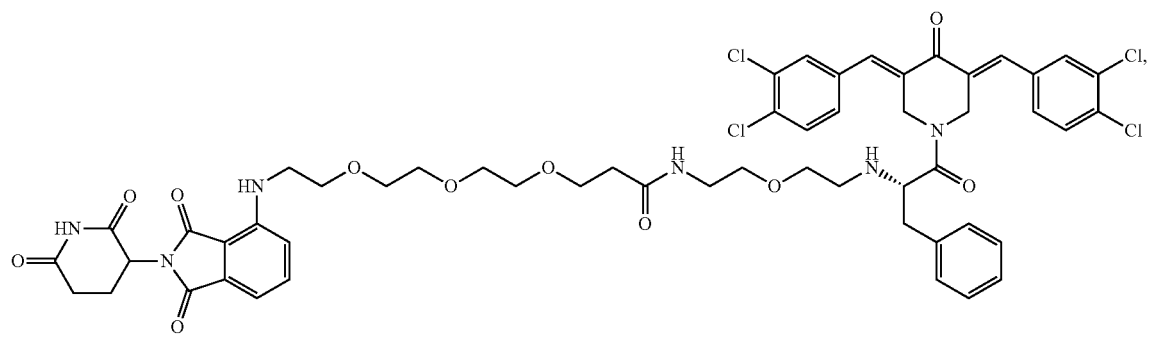
(WL4)

-continued

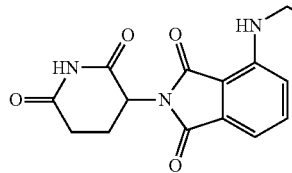

or a pharmaceutically acceptable salt, solvate, hydrate, tautomer, or stereoisomer thereof.

16. A pharmaceutical composition comprising a therapeutically effective amount of the compound of claim 1, or a pharmaceutically acceptable salt, solvate, hydrate, tautomer, or stereoisomer thereof, and optionally a pharmaceutically acceptable excipient.

17. The compound of claim 1, or a pharmaceutically acceptable salt, solvate, hydrate, tautomer, or stereoisomer thereof, wherein $R^{34}$ is H.

18. A method of treating a proliferative disease in a subject in need thereof, the method comprising administering to the subject a therapeutically effective amount of the compound of claim 17, or a pharmaceutically acceptable salt, solvate, hydrate, tautomer, or stereoisomer thereof.

19. The method of claim 18, wherein the proliferative disease is cancer.

20. The method of claim 19, wherein the cancer is multiple myeloma, leukemia, or lymphoma.

* * * * *

SEQUENCE LISTING

```
<160> NUMBER OF SEQ ID NOS: 6

<210> SEQ ID NO 1
<211> LENGTH: 352
<212> TYPE: PRT
<213> ORGANISM: Homo sapiens

<400> SEQUENCE: 1

Met Glu Ser Gly Gly Arg Pro Ser Leu Cys Gln Phe Ile Leu Leu Gly
 1               5                  10                  15

Thr Thr Ser Val Val Thr Ala Ala Leu Tyr Ser Val Tyr Arg Gln Lys
            20                  25                  30

Ala Arg Val Ser Gln Glu Leu Lys Gly Ala Lys Lys Val His Leu Gly
        35                  40                  45

Glu Asp Leu Lys Ser Ile Leu Ser Glu Ala Pro Gly Lys Cys Val Pro
    50                  55                  60

Tyr Ala Val Ile Glu Gly Ala Val Arg Ser Val Lys Glu Thr Leu Asn
65                  70                  75                  80

Ser Gln Phe Val Glu Asn Cys Lys Gly Val Ile Gln Arg Leu Thr Leu
                85                  90                  95

Gln Glu His Lys Met Val Trp Asn Arg Thr Thr His Leu Trp Asn Asp
            100                 105                 110

Cys Ser Lys Ile Ile His Gln Arg Thr Asn Thr Val Pro Phe Asp Leu
        115                 120                 125

Val Pro His Glu Asp Gly Val Asp Val Ala Val Arg Val Leu Lys Pro
    130                 135                 140

Leu Asp Ser Val Asp Leu Gly Leu Glu Thr Val Tyr Glu Lys Phe His
145                 150                 155                 160

Pro Ser Ile Gln Ser Phe Thr Asp Val Ile Gly His Tyr Ile Ser Gly
                165                 170                 175

Glu Arg Pro Lys Gly Ile Gln Glu Thr Glu Met Leu Lys Val Gly
            180                 185                 190
```

```
Ala Thr Leu Thr Gly Val Gly Glu Leu Val Leu Asp Asn Asn Ser Val
            195                 200                 205

Arg Leu Gln Pro Pro Lys Gln Gly Met Gln Tyr Tyr Leu Ser Ser Gln
    210                 215                 220

Asp Phe Asp Ser Leu Leu Gln Arg Gln Glu Ser Ser Val Arg Leu Trp
225                 230                 235                 240

Lys Val Leu Ala Leu Val Phe Gly Phe Ala Thr Cys Ala Thr Leu Phe
                245                 250                 255

Phe Ile Leu Arg Lys Gln Tyr Leu Gln Arg Gln Glu Arg Leu Arg Leu
                260                 265                 270

Lys Gln Met Gln Glu Glu Phe Gln Glu His Glu Ala Gln Leu Leu Ser
            275                 280                 285

Arg Ala Lys Pro Glu Asp Arg Glu Ser Leu Lys Ser Ala Cys Val Val
    290                 295                 300

Cys Leu Ser Ser Phe Lys Ser Cys Val Phe Leu Glu Cys Gly His Val
305                 310                 315                 320

Cys Ser Cys Thr Glu Cys Tyr Arg Ala Leu Pro Glu Pro Lys Lys Cys
                325                 330                 335

Pro Ile Cys Arg Gln Ala Ile Thr Arg Val Ile Pro Pro Tyr Asn Ser
                340                 345                 350

<210> SEQ ID NO 2
<211> LENGTH: 923
<212> TYPE: PRT
<213> ORGANISM: Homo sapiens

<400> SEQUENCE: 2

Met Glu Glu Gly Asn Asn Asn Glu Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45

Pro Ala Pro Gln Gln His Glu Glu Glu Asp Leu Asp Asp Asp Val Ile
    50                  55                  60

Leu Thr Glu Thr Asn Lys Pro Gln Arg Ser Arg Pro Asn Leu Ile Lys
65                  70                  75                  80

Pro Ala Ala Gln Trp Gln Asp Leu Lys Arg Leu Gly Glu Glu Arg Pro
                85                  90                  95

Lys Lys Ser Arg Ala Ala Phe Glu Ser Asp Lys Ser Ser Tyr Phe Ser
                100                 105                 110

Val Cys Asn Asn Pro Leu Phe Asp Ser Gly Ala Gln Asp Asp Ser Glu
            115                 120                 125

Asp Asp Tyr Gly Glu Phe Leu Asp Leu Gly Pro Gly Ile Ser Glu
    130                 135                 140

Phe Thr Lys Pro Ser Gly Gln Thr Glu Arg Glu Pro Lys Pro Gly Pro
145                 150                 155                 160

Ser His Asn Gln Ala Ala Asn Asp Ile Val Asn Pro Arg Ser Glu Gln
                165                 170                 175

Lys Val Ile Ile Leu Glu Glu Gly Ser Leu Leu Tyr Thr Glu Ser Asp
                180                 185                 190

Pro Leu Glu Thr Gln Asn Gln Ser Ser Glu Asp Ser Glu Thr Glu Leu
            195                 200                 205

Leu Ser Asn Leu Gly Glu Ser Ala Ala Leu Ala Asp Asp Gln Ala Ile
            210                 215                 220
```

```
Glu Glu Asp Cys Trp Leu Asp His Pro Tyr Phe Gln Ser Leu Asn Gln
225                 230                 235                 240

Gln Pro Arg Glu Ile Thr Asn Gln Val Val Pro Gln Glu Arg Gln Pro
                245                 250                 255

Glu Ala Glu Leu Gly Arg Leu Leu Phe Gln His Glu Phe Pro Gly Pro
            260                 265                 270

Ala Phe Pro Arg Pro Glu Pro Gln Gln Gly Gly Ile Ser Gly Pro Ser
            275                 280                 285

Ser Pro Gln Pro Ala His Pro Leu Gly Glu Phe Glu Asp Gln Gln Leu
        290                 295                 300

Ala Ser Asp Asp Glu Pro Gly Pro Ala Phe Pro Met Gln Glu Ser
305                 310                 315                 320

Gln Glu Pro Asn Leu Glu Asn Ile Trp Gly Gln Glu Ala Ala Glu Val
                325                 330                 335

Asp Gln Glu Leu Val Glu Leu Leu Val Lys Glu Thr Glu Ala Arg Phe
                340                 345                 350

Pro Asp Val Ala Asn Gly Phe Ile Glu Glu Ile Ile His Phe Lys Asn
            355                 360                 365

Tyr Tyr Asp Leu Asn Val Leu Cys Asn Phe Leu Leu Glu Asn Pro Asp
370                 375                 380

Tyr Pro Lys Arg Glu Asp Arg Ile Ile Ile Asn Pro Ser Ser Ser Leu
385                 390                 395                 400

Leu Ala Ser Gln Asp Glu Thr Lys Leu Pro Lys Ile Asp Phe Phe Asp
                405                 410                 415

Tyr Ser Lys Leu Thr Pro Leu Asp Gln Arg Cys Phe Ile Gln Ala Ala
            420                 425                 430

Asp Leu Leu Met Ala Asp Phe Lys Val Leu Ser Ser Gln Asp Ile Lys
            435                 440                 445

Trp Ala Leu His Glu Leu Lys Gly His Tyr Ala Ile Thr Arg Lys Ala
450                 455                 460

Leu Ser Asp Ala Ile Lys Lys Trp Gln Glu Leu Ser Pro Glu Thr Ser
465                 470                 475                 480

Gly Lys Arg Lys Arg Lys Gln Met Asn Gln Tyr Ser Tyr Ile Asp
                485                 490                 495

Phe Lys Phe Glu Gln Gly Asp Ile Lys Ile Glu Lys Arg Met Phe Phe
            500                 505                 510

Leu Glu Asn Lys Arg Arg His Cys Arg Ser Tyr Asp Arg Arg Ala Leu
                515                 520                 525

Leu Pro Ala Val Gln Gln Gln Glu Phe Tyr Glu Gln Lys Ile Lys
            530                 535                 540

Glu Met Ala Glu His Glu Asp Phe Leu Leu Ala Leu Gln Met Asn Glu
545                 550                 555                 560

Glu Gln Tyr Gln Lys Asp Gly Gln Leu Ile Glu Cys Arg Cys Tyr
                565                 570                 575

Gly Glu Phe Pro Phe Glu Glu Leu Thr Gln Cys Ala Asp Ala His Leu
            580                 585                 590

Phe Cys Lys Glu Cys Leu Ile Arg Tyr Ala Gln Glu Ala Val Phe Gly
        595                 600                 605

Ser Gly Lys Leu Glu Leu Ser Cys Met Glu Gly Ser Cys Thr Cys Ser
        610                 615                 620

Phe Pro Thr Ser Glu Leu Glu Lys Val Leu Pro Gln Thr Ile Leu Tyr
625                 630                 635                 640
```

-continued

Lys Tyr Tyr Glu Arg Lys Ala Glu Glu Val Ala Ala Tyr Ala
                645                 650                 655

Asp Glu Leu Val Arg Cys Pro Ser Cys Ser Phe Pro Ala Leu Leu Asp
            660                 665                 670

Ser Asp Val Lys Arg Phe Ser Cys Pro Asn Pro His Cys Arg Lys Glu
            675                 680                 685

Thr Cys Arg Lys Cys Gln Gly Leu Trp Lys Glu His Asn Gly Leu Thr
        690                 695                 700

Cys Glu Glu Leu Ala Glu Lys Asp Asp Ile Lys Tyr Arg Thr Ser Ile
705                 710                 715                 720

Glu Glu Lys Met Thr Ala Ala Arg Ile Arg Lys Cys His Lys Cys Gly
                725                 730                 735

Thr Gly Leu Ile Lys Ser Glu Gly Cys Asn Arg Met Ser Cys Arg Cys
            740                 745                 750

Gly Ala Gln Met Cys Tyr Leu Cys Arg Val Ser Ile Asn Gly Tyr Asp
            755                 760                 765

His Phe Cys Gln His Pro Arg Ser Pro Gly Ala Pro Cys Gln Glu Cys
        770                 775                 780

Ser Arg Cys Ser Leu Trp Thr Asp Pro Thr Glu Asp Glu Lys Leu
785                 790                 795                 800

Ile Glu Glu Ile Gln Lys Glu Ala Glu Glu Gln Lys Arg Lys Asn
                805                 810                 815

Gly Glu Asn Thr Phe Lys Arg Ile Gly Pro Pro Leu Glu Lys Pro Val
            820                 825                 830

Glu Lys Val Gln Arg Val Glu Ala Leu Pro Arg Pro Val Pro Gln Asn
                835                 840                 845

Leu Pro Gln Pro Gln Met Pro Pro Tyr Ala Phe Ala His Pro Pro Phe
    850                 855                 860

Pro Leu Pro Pro Val Arg Pro Val Phe Asn Asn Phe Pro Leu Asn Met
865                 870                 875                 880

Gly Pro Ile Pro Ala Pro Tyr Val Pro Leu Pro Asn Val Arg Val
            885                 890                 895

Asn Tyr Asp Phe Gly Pro Ile His Met Pro Leu Glu His Asn Leu Pro
            900                 905                 910

Met His Phe Gly Pro Gln Pro Arg His Arg Phe
        915                 920

<210> SEQ ID NO 3
<211> LENGTH: 866
<212> TYPE: PRT
<213> ORGANISM: Homo sapiens

<400> SEQUENCE: 3

Met Glu Glu Gly Asn Asn Asn Glu Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45

Pro Ala Pro Gln Gln His Glu Glu Glu Asp Leu Asp Asp Val Ile
        50                  55                  60

Leu Thr Glu Asp Asp Ser Glu Asp Asp Tyr Gly Glu Phe Leu Asp Leu
65                  70                  75                  80

Gly Pro Pro Gly Ile Ser Glu Phe Thr Lys Pro Ser Gly Gln Thr Glu
                85                  90                  95

```
Arg Glu Pro Lys Pro Gly Pro Ser His Asn Gln Ala Ala Asn Asp Ile
            100                 105                 110

Val Asn Pro Arg Ser Glu Gln Lys Val Ile Ile Leu Glu Glu Gly Ser
        115                 120                 125

Leu Leu Tyr Thr Glu Ser Asp Pro Leu Glu Thr Gln Asn Gln Ser Ser
    130                 135                 140

Glu Asp Ser Glu Thr Glu Leu Leu Ser Asn Leu Gly Glu Ser Ala Ala
145                 150                 155                 160

Leu Ala Asp Asp Gln Ala Ile Glu Glu Asp Cys Trp Leu Asp His Pro
                165                 170                 175

Tyr Phe Gln Ser Leu Asn Gln Gln Pro Arg Glu Ile Thr Asn Gln Val
            180                 185                 190

Val Pro Gln Glu Arg Gln Pro Glu Ala Glu Leu Gly Arg Leu Leu Phe
        195                 200                 205

Gln His Glu Phe Pro Gly Pro Ala Phe Pro Arg Pro Glu Pro Gln Gln
    210                 215                 220

Gly Gly Ile Ser Gly Pro Ser Ser Pro Gln Pro Ala His Pro Leu Gly
225                 230                 235                 240

Glu Phe Glu Asp Gln Gln Leu Ala Ser Asp Asp Glu Gly Pro Gly Pro
                245                 250                 255

Ala Phe Pro Met Gln Glu Ser Gln Glu Pro Asn Leu Gly Asn Ile Trp
            260                 265                 270

Gly Gln Glu Ala Ala Glu Val Asp Gln Glu Leu Val Glu Leu Leu Val
        275                 280                 285

Lys Glu Thr Glu Ala Arg Phe Pro Asp Val Ala Asn Gly Phe Ile Glu
    290                 295                 300

Glu Ile Ile His Phe Lys Asn Tyr Tyr Asp Leu Asn Val Leu Cys Asn
305                 310                 315                 320

Phe Leu Leu Glu Asn Pro Asp Tyr Pro Lys Arg Glu Asp Arg Ile Ile
                325                 330                 335

Ile Asn Pro Ser Ser Ser Leu Leu Ala Ser Gln Asp Glu Thr Lys Leu
            340                 345                 350

Pro Lys Ile Asp Phe Phe Asp Tyr Ser Lys Leu Thr Pro Leu Asp Gln
        355                 360                 365

Arg Cys Phe Ile Gln Ala Ala Asp Leu Leu Met Ala Asp Phe Lys Val
    370                 375                 380

Leu Ser Ser Gln Asp Ile Lys Trp Ala Leu His Glu Leu Lys Gly His
385                 390                 395                 400

Tyr Ala Ile Thr Arg Lys Ala Leu Ser Asp Ala Ile Lys Lys Trp Gln
                405                 410                 415

Glu Leu Ser Pro Glu Thr Ser Gly Lys Arg Lys Lys Arg Lys Gln Met
            420                 425                 430

Asn Gln Tyr Ser Tyr Ile Asp Phe Lys Phe Glu Gln Gly Asp Ile Lys
        435                 440                 445

Ile Glu Lys Arg Met Phe Phe Leu Glu Asn Lys Arg His Cys Arg
    450                 455                 460

Ser Tyr Asp Arg Arg Ala Leu Leu Pro Ala Val Gln Gln Gln Glu
465                 470                 475                 480

Phe Tyr Glu Gln Lys Ile Lys Glu Met Ala Glu His Glu Asp Phe Leu
                485                 490                 495

Leu Ala Leu Gln Met Asn Glu Glu Gln Tyr Gln Lys Asp Gly Gln Leu
            500                 505                 510
```

```
Ile Glu Cys Arg Cys Cys Tyr Gly Glu Phe Pro Phe Glu Leu Thr
        515                 520                 525

Gln Cys Ala Asp Ala His Leu Phe Cys Lys Glu Cys Leu Ile Arg Tyr
530                 535                 540

Ala Gln Glu Ala Val Phe Gly Ser Gly Lys Leu Glu Leu Ser Cys Met
545                 550                 555                 560

Glu Gly Ser Cys Thr Cys Ser Phe Pro Thr Ser Glu Leu Glu Lys Val
                565                 570                 575

Leu Pro Gln Thr Ile Leu Tyr Lys Tyr Tyr Glu Arg Lys Ala Glu Glu
            580                 585                 590

Glu Val Ala Ala Ala Tyr Ala Asp Glu Leu Val Arg Cys Pro Ser Cys
        595                 600                 605

Ser Phe Pro Ala Leu Leu Asp Ser Asp Val Lys Arg Phe Ser Cys Pro
    610                 615                 620

Asn Pro His Cys Arg Lys Glu Thr Cys Arg Lys Cys Gln Gly Leu Trp
625                 630                 635                 640

Lys Glu His Asn Gly Leu Thr Cys Glu Glu Leu Ala Glu Lys Asp Asp
                645                 650                 655

Ile Lys Tyr Arg Thr Ser Ile Glu Glu Lys Met Thr Ala Ala Arg Ile
            660                 665                 670

Arg Lys Cys His Lys Cys Gly Thr Gly Leu Ile Lys Ser Glu Gly Cys
        675                 680                 685

Asn Arg Met Ser Cys Arg Cys Gly Ala Gln Met Cys Tyr Leu Cys Arg
    690                 695                 700

Val Ser Ile Asn Gly Tyr Asp His Phe Cys Gln His Pro Arg Ser Pro
705                 710                 715                 720

Gly Ala Pro Cys Gln Glu Cys Ser Arg Cys Ser Leu Trp Thr Asp Pro
                725                 730                 735

Thr Glu Asp Asp Glu Lys Leu Ile Glu Glu Ile Gln Lys Glu Ala Glu
            740                 745                 750

Glu Glu Gln Lys Arg Lys Asn Gly Glu Asn Thr Phe Lys Arg Ile Gly
        755                 760                 765

Pro Pro Leu Glu Lys Pro Val Glu Lys Val Gln Arg Val Glu Ala Leu
    770                 775                 780

Pro Arg Pro Val Pro Gln Asn Leu Pro Gln Pro Gln Met Pro Pro Tyr
785                 790                 795                 800

Ala Phe Ala His Pro Pro Phe Pro Leu Pro Pro Val Arg Pro Val Phe
                805                 810                 815

Asn Asn Phe Pro Leu Asn Met Gly Pro Ile Pro Ala Pro Tyr Val Pro
            820                 825                 830

Pro Leu Pro Asn Val Arg Val Asn Tyr Asp Phe Gly Pro Ile His Met
        835                 840                 845

Pro Leu Glu His Asn Leu Pro Met His Phe Gly Pro Gln Pro Arg His
    850                 855                 860

Arg Phe
865

<210> SEQ ID NO 4
<211> LENGTH: 407
<212> TYPE: PRT
<213> ORGANISM: Homo sapiens

<400> SEQUENCE: 4

Met Thr Thr Ser Gly Ala Leu Phe Pro Ser Leu Val Pro Gly Ser Arg
1               5                   10                  15
```

Gly Ala Ser Asn Lys Tyr Leu Val Glu Phe Arg Ala Gly Lys Met Ser
            20                  25                  30

Leu Lys Gly Thr Thr Val Thr Pro Asp Lys Arg Lys Gly Leu Val Tyr
        35                  40                  45

Ile Gln Gln Thr Asp Asp Ser Leu Ile His Phe Cys Trp Lys Asp Arg
 50                  55                  60

Thr Ser Gly Asn Val Glu Asp Asp Leu Ile Ile Phe Pro Asp Asp Cys
 65                  70                  75                  80

Glu Phe Lys Arg Val Pro Gln Cys Pro Ser Gly Arg Val Tyr Val Leu
                85                  90                  95

Lys Phe Lys Ala Gly Ser Lys Arg Leu Phe Phe Trp Met Gln Glu Pro
            100                 105                 110

Lys Thr Asp Gln Asp Glu Glu His Cys Arg Lys Val Asn Glu Tyr Leu
        115                 120                 125

Asn Asn Pro Pro Met Pro Gly Ala Leu Gly Ala Ser Gly Ser Ser Gly
    130                 135                 140

His Glu Leu Ser Ala Leu Gly Gly Glu Gly Gly Leu Gln Ser Leu Leu
145                 150                 155                 160

Gly Asn Met Ser His Ser Gln Leu Met Gln Leu Ile Gly Pro Ala Gly
                165                 170                 175

Leu Gly Gly Leu Gly Gly Leu Gly Ala Leu Thr Gly Pro Gly Leu Ala
            180                 185                 190

Ser Leu Leu Gly Ser Ser Gly Pro Pro Gly Ser Ser Ser Ser Ser Ser
        195                 200                 205

Ser Arg Ser Gln Ser Ala Ala Val Thr Pro Ser Ser Thr Thr Ser Ser
210                 215                 220

Thr Arg Ala Thr Pro Ala Pro Ser Ala Pro Ala Ala Ser Ala Thr
225                 230                 235                 240

Ser Pro Ser Pro Ala Pro Ser Ser Gly Asn Gly Ala Ser Thr Ala Ala
                245                 250                 255

Ser Pro Thr Gln Pro Ile Gln Leu Ser Asp Leu Gln Ser Ile Leu Ala
            260                 265                 270

Thr Met Asn Val Pro Ala Gly Pro Ala Gly Gln Gln Val Asp Leu
        275                 280                 285

Ala Ser Val Leu Thr Pro Glu Ile Met Ala Pro Ile Leu Ala Asn Ala
290                 295                 300

Asp Val Gln Glu Arg Leu Leu Pro Tyr Leu Pro Ser Gly Glu Ser Leu
305                 310                 315                 320

Pro Gln Thr Ala Asp Glu Ile Gln Asn Thr Leu Thr Ser Pro Gln Phe
                325                 330                 335

Gln Gln Ala Leu Gly Met Phe Ser Ala Ala Leu Ala Ser Gly Gln Leu
            340                 345                 350

Gly Pro Leu Met Cys Gln Phe Gly Leu Pro Ala Glu Ala Val Glu Ala
        355                 360                 365

Ala Asn Lys Gly Asp Val Glu Ala Phe Ala Lys Ala Met Gln Asn Asn
    370                 375                 380

Ala Lys Pro Glu Gln Lys Glu Gly Asp Thr Lys Asp Lys Lys Asp Glu
385                 390                 395                 400

Glu Glu Asp Met Ser Leu Asp
                405

<210> SEQ ID NO 5
<211> LENGTH: 368

```
<212> TYPE: PRT
<213> ORGANISM: Homo sapiens

<400> SEQUENCE: 5

Met Thr Thr Ser Gly Ala Leu Phe Pro Ser Leu Val Pro Gly Ser Arg
1               5                   10                  15

Gly Ala Ser Asn Lys Tyr Leu Val Glu Phe Arg Ala Gly Lys Met Ser
                20                  25                  30

Leu Lys Gly Thr Thr Val Thr Pro Asp Lys Arg Lys Gly Leu Val Tyr
            35                  40                  45

Ile Gln Gln Thr Asp Asp Ser Leu Ile His Phe Cys Trp Lys Asp Arg
50                  55                  60

Thr Ser Gly Asn Val Glu Asp Glu Pro Lys Thr Asp Gln Asp Glu Glu
65                  70                  75                  80

His Cys Arg Lys Val Asn Glu Tyr Leu Asn Asn Pro Pro Met Pro Gly
                85                  90                  95

Ala Leu Gly Ala Ser Gly Ser Ser Gly His Glu Leu Ser Ala Leu Gly
                100                 105                 110

Gly Glu Gly Gly Leu Gln Ser Leu Leu Gly Asn Met Ser His Ser Gln
            115                 120                 125

Leu Met Gln Leu Ile Gly Pro Ala Gly Leu Gly Leu Gly Leu
130                 135                 140

Gly Ala Leu Thr Gly Pro Gly Leu Ala Ser Leu Leu Gly Ser Ser Gly
145                 150                 155                 160

Pro Pro Gly Ser Ser Ser Ser Ser Ser Arg Ser Gln Ser Ala Ala
                165                 170                 175

Val Thr Pro Ser Ser Thr Ser Ser Thr Arg Ala Thr Pro Ala Pro
                180                 185                 190

Ser Ala Pro Ala Ala Ser Ala Thr Ser Pro Ser Pro Ala Pro Ser
                195                 200                 205

Ser Gly Asn Gly Ala Ser Thr Ala Ala Ser Pro Thr Gln Pro Ile Gln
                210                 215                 220

Leu Ser Asp Leu Gln Ser Ile Leu Ala Thr Met Asn Val Pro Ala Gly
225                 230                 235                 240

Pro Ala Gly Gly Gln Gln Val Asp Leu Ala Ser Val Leu Thr Pro Glu
                245                 250                 255

Ile Met Ala Pro Ile Leu Ala Asn Ala Asp Val Gln Glu Arg Leu Leu
                260                 265                 270

Pro Tyr Leu Pro Ser Gly Glu Ser Leu Pro Gln Thr Ala Asp Glu Ile
                275                 280                 285

Gln Asn Thr Leu Thr Ser Pro Gln Phe Gln Gln Ala Leu Gly Met Phe
                290                 295                 300

Ser Ala Ala Leu Ala Ser Gly Gln Leu Gly Pro Leu Met Cys Gln Phe
305                 310                 315                 320

Gly Leu Pro Ala Glu Ala Val Glu Ala Ala Asn Lys Gly Asp Val Glu
                325                 330                 335

Ala Phe Ala Lys Ala Met Gln Asn Asn Ala Lys Pro Glu Gln Lys Glu
                340                 345                 350

Gly Asp Thr Lys Asp Lys Lys Asp Glu Glu Glu Asp Met Ser Leu Asp
                355                 360                 365

<210> SEQ ID NO 6
<211> LENGTH: 389
<212> TYPE: PRT
<213> ORGANISM: Homo sapiens
```

<400> SEQUENCE: 6

```
Met Ala Asp Pro Arg Asp Lys Ala Leu Gln Asp Tyr Arg Lys Lys Leu
1               5                   10                  15

Leu Glu His Lys Glu Ile Asp Gly Arg Leu Lys Glu Leu Arg Glu Gln
            20                  25                  30

Leu Lys Glu Leu Thr Lys Gln Tyr Glu Lys Ser Glu Asn Asp Leu Lys
        35                  40                  45

Ala Leu Gln Ser Val Gly Gln Ile Val Gly Glu Val Leu Lys Gln Leu
    50                  55                  60

Thr Glu Glu Lys Phe Ile Val Lys Ala Thr Asn Gly Pro Arg Tyr Val
65                  70                  75                  80

Val Gly Cys Arg Arg Gln Leu Asp Lys Ser Lys Leu Lys Pro Gly Thr
                85                  90                  95

Arg Val Ala Leu Asp Met Thr Thr Leu Thr Ile Met Arg Tyr Leu Pro
                100                 105                 110

Arg Glu Val Asp Pro Leu Val Tyr Asn Met Ser His Glu Asp Pro Gly
            115                 120                 125

Asn Val Ser Tyr Ser Glu Ile Gly Gly Leu Ser Glu Gln Ile Arg Glu
130                 135                 140

Leu Arg Glu Val Ile Glu Leu Pro Leu Thr Asn Pro Glu Leu Phe Gln
145                 150                 155                 160

Arg Val Gly Ile Ile Pro Pro Lys Gly Cys Leu Leu Tyr Gly Pro Pro
                165                 170                 175

Gly Thr Gly Lys Thr Leu Leu Ala Arg Ala Val Ala Ser Gln Leu Asp
                180                 185                 190

Cys Asn Phe Leu Lys Val Val Ser Ser Ile Val Asp Lys Tyr Ile
                195                 200                 205

Gly Glu Ser Ala Arg Leu Ile Arg Glu Met Phe Asn Tyr Ala Arg Asp
            210                 215                 220

His Gln Pro Cys Ile Ile Phe Met Asp Glu Ile Asp Ala Ile Gly Gly
225                 230                 235                 240

Arg Arg Phe Ser Glu Gly Thr Ser Ala Asp Arg Glu Ile Gln Arg Thr
                245                 250                 255

Leu Met Glu Leu Leu Asn Gln Met Asp Gly Phe Asp Thr Leu His Arg
            260                 265                 270

Val Lys Met Ile Met Ala Thr Asn Arg Pro Asp Thr Leu Asp Pro Ala
            275                 280                 285

Leu Leu Arg Pro Gly Arg Leu Asp Arg Lys Ile His Ile Asp Leu Pro
            290                 295                 300

Asn Glu Gln Ala Arg Leu Asp Ile Leu Lys Ile His Ala Gly Pro Ile
305                 310                 315                 320

Thr Lys His Gly Glu Ile Asp Tyr Glu Ala Ile Val Lys Leu Ser Asp
                325                 330                 335

Gly Phe Asn Gly Ala Asp Leu Arg Asn Val Cys Thr Glu Ala Gly Met
            340                 345                 350

Phe Ala Ile Arg Ala Asp His Asp Phe Val Val Gln Glu Asp Phe Met
            355                 360                 365

Lys Ala Val Arg Lys Val Ala Asp Ser Lys Lys Leu Glu Ser Lys Leu
            370                 375                 380

Asp Tyr Lys Pro Val
385
```